United States Patent
Klessig et al.

(10) Patent No.: US 11,019,776 B2
(45) Date of Patent: *Jun. 1, 2021

(54) COMPOSITIONS AND METHODS FOR MODULATING IMMUNITY IN PLANTS

(71) Applicant: Boyce Thompson Institute for Plant Research, Inc., Ithaca, NY (US)

(72) Inventors: Daniel Klessig, Dryden, NY (US); Frank Schroeder, Ithaca, NY (US); Patricia Manosalva, Ithaca, NY (US)

(73) Assignee: BOYCE THOMPSON INSTITUTE FOR PLANT RESEARCH, INC., Ithaca, NY (US)

( * ) Notice: Subject to any disclaimer, the term of this patent is extended or adjusted under 35 U.S.C. 154(b) by 26 days.

This patent is subject to a terminal disclaimer.

(21) Appl. No.: 16/161,252

(22) Filed: Oct. 16, 2018

(65) Prior Publication Data

US 2019/0053451 A1    Feb. 21, 2019

Related U.S. Application Data

(63) Continuation of application No. 14/854,363, filed on Sep. 15, 2015, now Pat. No. 10,136,595, which is a continuation-in-part of application No. PCT/US2014/030136, filed on Mar. 17, 2014.

(60) Provisional application No. 61/789,445, filed on Mar. 15, 2013, provisional application No. 62/079,242, filed on Nov. 13, 2014, provisional application No. 62/152,570, filed on Apr. 24, 2015.

(51) Int. Cl.
*A01H 3/04* (2006.01)
*C12N 15/82* (2006.01)
*A01N 43/16* (2006.01)
*A01N 43/38* (2006.01)
*A01N 63/10* (2020.01)

(52) U.S. Cl.
CPC ............ *A01H 3/04* (2013.01); *A01N 43/16* (2013.01); *A01N 43/38* (2013.01); *A01N 63/10* (2020.01); *C12N 15/8281* (2013.01); *C12N 15/8282* (2013.01); *C12N 15/8283* (2013.01); *C12N 15/8285* (2013.01)

(58) Field of Classification Search
CPC ..................... C12N 15/8282; C12N 15/8281
See application file for complete search history.

(56) References Cited

U.S. PATENT DOCUMENTS 8,318,146 B1    11/2012 Teal et al.

FOREIGN PATENT DOCUMENTS

| WO | 2010/009241 A2 | 1/2010 |
| WO | 2010/146062 A2 | 12/2010 |
| WO | 2012/084858 A2 | 6/2012 |
| WO | 2013/022985 A2 | 2/2013 |
| WO | 2013/022997 A2 | 2/2013 |

(Continued)

OTHER PUBLICATIONS

Hsueh, Y.-P. et al 2013. Nematode-trapping fungi eavesdrop on nematode pheromones. Current Biology, 23(1), pp. 83-86 (Year: 2013).*

(Continued)

*Primary Examiner* — Weihua Fan
(74) *Attorney, Agent, or Firm* — Robert C. Netter, Jr.; Dann, Dorfman, Herrell & Skillman

(57) ABSTRACT

Compositions and methods for enhancing disease resistance in plants are disclosed.

39 Claims, 25 Drawing Sheets

Specification includes a Sequence Listing.

(56) References Cited

FOREIGN PATENT DOCUMENTS

| WO | WO-2013/022997 | * | 2/2013 | ............ A01N 43/16 |
| WO | WO-2013022997 A2 | * | 2/2013 | ............ A61P 25/00 |

OTHER PUBLICATIONS

Ludewig, Andreas H., and Frank C. Schroeder. "Ascaroside signaling in C. elegans." WormBook: the online review of C. elegans biology (2013): 1-22 (Year: 2013).*

Manosalva, P. Manohar, M., Von Reuss, S.H., Chen, S., Koch, A., Kaplan, F., Choe, A., Micikas, R.J., Wang, X., Kogel, K.H. and Sternberg, P.W., 2015. Conserved nematode signalling molecules elicit plant defenses and pathogen resistance. Nature communications, 6. (Year: 2015).* von Reuss, Stephan H., and Frank C. Schroeder. "Combinatorial chemistry in nematodes: modular assembly of primary metabolism-derived building blocks." Natural product reports 32.7 (2015): 994-1006. (Year: 2015).*

Daudi, Arsalan, et al. "The apoplastic oxidative burst peroxidase in *Arabidopsis* is a major component of pattern-triggered immunity." The Plant Cell 24.1 (2012): 275-287 (Year: 2012).*

McConn, Michele, et al. "Jasmonate is essential for insect defense in *Arabidopsis*." Proceedings of the National Academy of Sciences 94.10 (1997): 5473-5477 (Year: 1997).*

Durrant, W.E., and Dong, X., 2004, Annual Review of Phytopathology vol. 42:1-464 (Year: 2004).*

Choe, Andrea, et al. "Ascaroside signaling is widely conserved among nematodes." Current Biology 22.9 (2012): 772-780. (Year: 2012).*

Jagdale, G. B., S. Kamoun, and P. S. Grewal. "Entomopathogenic nematodes induce components of systemic resistance in plants: biochemical and molecular evidence." Biological Control 51.1 (2009): 102-109. (Year: 2009).*

Noguez et al., A novel ascaroside controls the parasitic life cycle of the entomopathogenic nematode Heterorhabditis bacteriophora, ACS Chem. Biol. 2012, 961-966, 7(6).

Srinivasan et al., A Modular Library of Small Molecule Signals Regulates Social Behaviors in Caenorhabditis elegans, PLOS Biology, 2012, e10012371, 10(1).

Srinivasan et al., A blend of small molecules regulates both mating and development in Caenorhabditis elegans, Nature, 2008, 1115-1118, 454(7208).

Hseuh et al., Nematode-trapping fungi eavesdrop on nematode pheromones, Current Biology, 2013, 83-86, 23.

Bose et al., Complex small-molecule architectures regulate phenotypic plasticity in a nematode, Angew Chem Int Ed Engl., 2012, 12438-12443, 51(50).

Von Reuss et al., Comparative metabolomics reveals biogenesis of Ascarosides, a modular library of small-molecule signals in C. elegans, J Am Chem Soc., 2012, 1817-1824, 134(3).

Choe et al., Ascaroside signaling is widely conserved among nematodes, Curr Biol., 2012, 772-780, 22.

Manosalva et al., Conserved nematode signalling molecules elicit plant defenses and pathogen resistance, Nature Communications, 2014, 6:7795.

Ludewig AH. and Schroeder FC, Ascaroside signaling in C. elegans (2013), WormBook, ed. The C. elegans Research Community, doi/10.1895/wormbook.1.1551, http://wormbook.org.

Kaplan, Fatma et al., "Interspecific Nematode Signals Regulate Dispersal Behavior", PLoS ONE (2012) 7(6): e38735.

Extended European Search Report and Written Opinion, dated Oct. 13, 2016, in corresponding European Patent Application No. 14764747. 3, filed Mar. 17, 2014.

Jagdale, G.B., et al., "Entomopathogenic nematodes induce components of systemic resistance in plants: Biochemical and molecular evidence" Biological Control (2009) 51:102-109.

Vonreuss, S.H., et al., "Combinatorial chemistry in nematodes: modular assembly of primary metabolism-derived building blocks" Nat. Prod. Rep. (2015) 32(7):994-1006.

Daudi, A., et al., "The apoplastic oxidative burst peroxidase in *Arabidopsis* is a major component of pattern-triggered immunity" Plant Cell (2012) 24(1):275-87.

McConn, M., et al., "Jasmonate is essential for insect defense in *Arabidopsis*" Proc. Natl. Acad. Sci., 94(10):5473-7.

Durrant, W.E, et al., "Systemic acquired resistance" Annu. Rev. Phytopathol. (2004) 42:185-209.

* cited by examiner

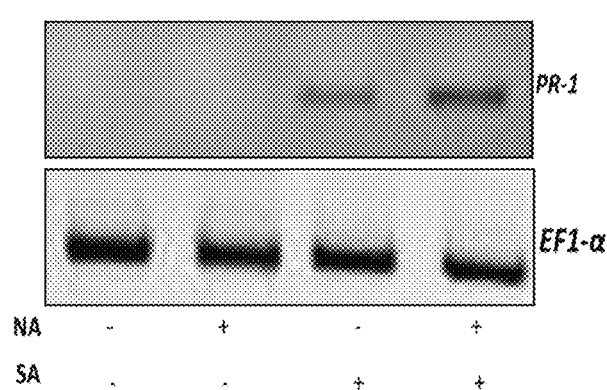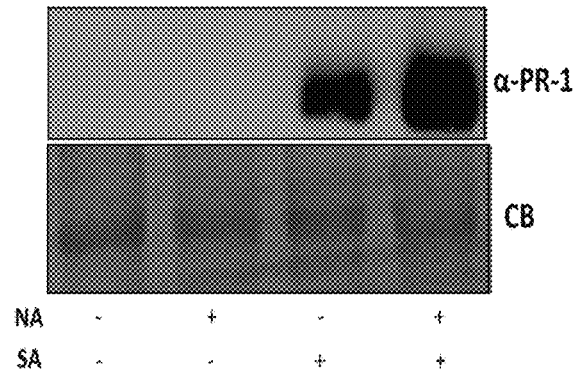
FIG. 3A                     FIG. 3B
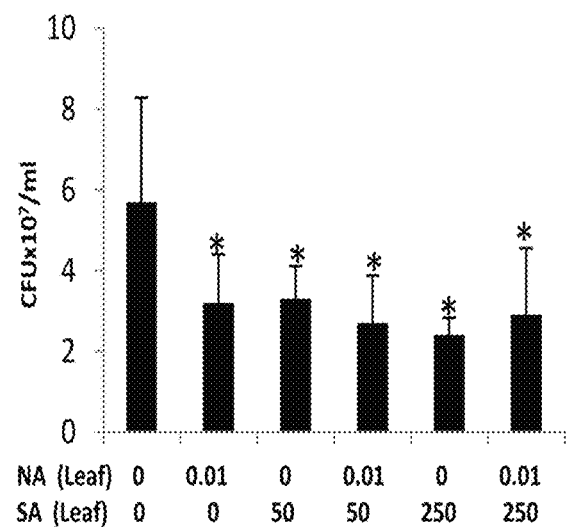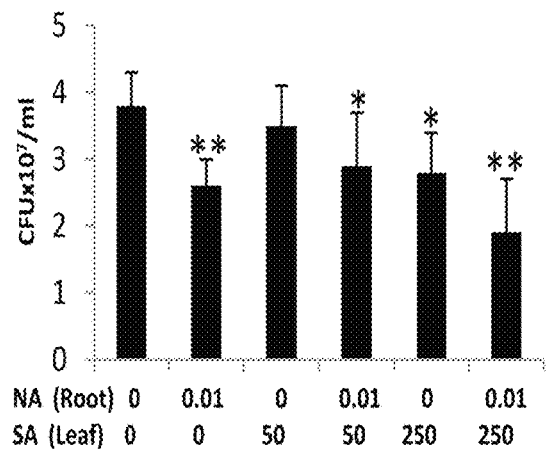
FIG. 4A                     FIG. 4B

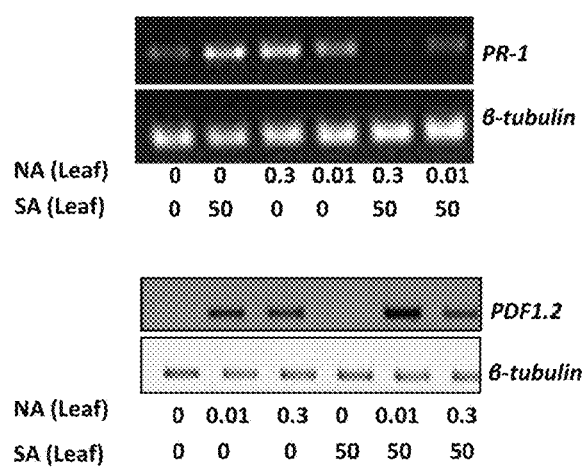
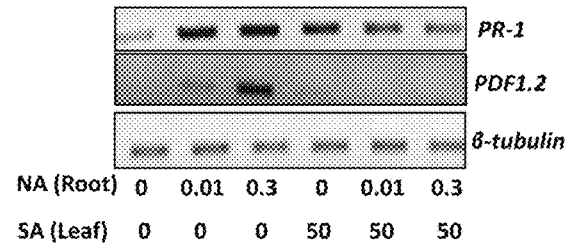
FIG. 5A    FIG. 5B
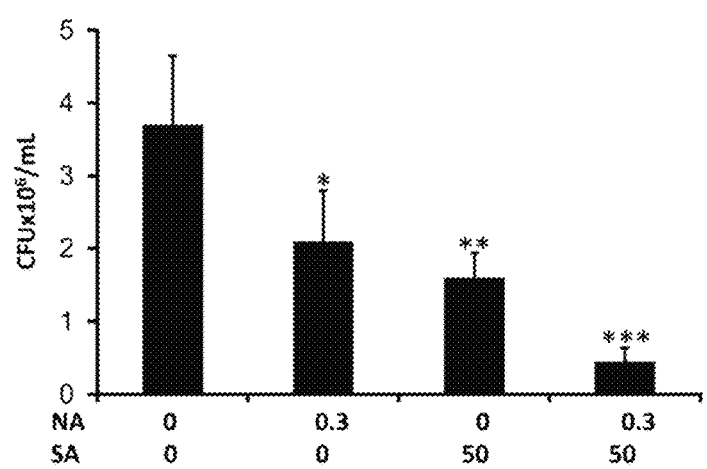
FIG. 6

COMPOSITIONS AND METHODS FOR MODULATING IMMUNITY IN PLANTS

This application is a continuation application of U.S. patent application Ser. No. 14/854,363, filed Sep. 15, 2015, which is a continuation-in-part of PCT/US2014/030136, filed on Mar. 17, 2014, which claims priority under 35 U.S.C. § 119(e) to U.S. Provisional Patent Application No. 61/789,445, filed Mar. 15, 2013. U.S. patent application Ser. No. 14/854,363 also claims priority under 35 U.S.C. § 119(e) to U.S. Provisional Patent Application No. 62/152,570, filed Apr. 24, 2015 and U.S. Provisional Patent Application No. 62/079,242, filed Nov. 13, 2014. The foregoing applications are incorporated by reference herein.

This invention was made with government support under Grant No. NIFA 2011-68004-30154 awarded by the United States Department of Agriculture. The government has certain rights in the invention.

FIELD OF THE INVENTION

This invention relates to the fields of agriculture, small molecule pesticides and plant disease resistance. More specifically, the invention provides a collection of small molecules called ascarosides and methods of use thereof for modulation of pathogens or resistance to pathogens in a variety of plant species.

BACKGROUND OF THE INVENTION

Several publications and patent documents are cited throughout the specification in order to describe the state of the art to which this invention pertains. Each of these citations is incorporated herein by reference as though set forth in full.

Over the past two decades, the recognition of specific molecular patterns has been shown to play a central role in the immune responses of plants and animals (Boller and Felix (2009) Annu Rev Plant Biol., 60:379-406; Ronald and Beutler (2010) Science 330:1061-1064; Pieterse et al. (2012) Annu Rev Cell Dev Biol., 28:489-521). Plants and animals have been shown to possess pattern recognition receptors that serve to detect several different molecular signatures associated with specific classes of microbes. For example, Arabidopsis recognize bacteria using specific pattern recognition receptors (PRRs) for flagellin, lipopolysaccharide, peptidoglycan, and other pathogen-associated molecular patterns (PAMPs). Because not only pathogenic microbes are recognized in this manner, these molecular signatures are also referred to by the more general term, Microbe-Associated Molecular Patterns (MAMPs; (Bittel and Robatzek (2007) Curr. Opin. Plant Biol., 10:335-341). MAMPs include carbohydrates, (glyco)-proteins, lipids, peptides, and sterols (Boller, T. (1995) Annu Rev Plant Phys., 46:189-214; Ebel and Mithofer (1998) Planta 206: 335-348; Nurnberger et al. (2004) Immunol Rev., 198:249-266). MAMPs/PAMPs are perceived at low concentrations and act as inducers of defense responses (Boller, T. (1995) Annu Rev Plant Phys., 46:189-214; Ebel and Mithofer (1998) Planta 206:335-348). Additionally, PAMP perception can lead to long-term sensitization of plants, resulting in more rapid and/or more intense activation of future defense responses, which can lead to enhanced resistance to both biotic and abiotic stresses (Conrath et al. (2006) Molecular Plant-Microbe Interactions 19:1062-1071).

Similar defense responses can be triggered by molecular species originating from the plant itself, so-called damage-associated molecular patterns (DAMPs; Bianchi, M. E. (2007) J. Leukocyte Biol., 81:1-5), which, for example, would result from herbivory by insects. In contrast, there are no known conserved insect- or nematode-associated molecular patterns that are recognized by plants, although a few species- or genus-specific families of lipid-derived small molecules from insect oral secretions have been shown to trigger plant defense responses (Schmelz et al. (2009) PNAS 106:653-657; Schroder, F. (1998) Angewandte Chemie-Intl. Ed., 37:1213-1216). In addition, oral secretions (OS) from feeding insects contain Herbivore-Associated Elicitors (HAE), which are also called Herbivore-Associated Molecular Patterns (HAMPs). This latter term covers all the herbivore-derived signaling compounds that might come into contact with a particular host plant and elicit defense responses (Bonaventure et al. (2011) Trends Plant Sci., 16, 294-299; Mithofer and Boland (2008) Plant Physiol., 146:825-831). Host perception of MAMPs, DAMPS, and HAMPs has been shown to involve shared signal transduction mechanisms, including activation of MAPKs, generation of reactive oxygen species (ROS), and activation of salicylic acid (SA)- and jasmonic acid (JA)-signaling pathways (Bonaventure et al. (2011) Trends Plant Sci., 16, 294-299; Kallenbach et al. (2010) Plant Physiol., 152:96-106; Asai et al. (2002) Nature 415:977-983; Pieterse et al. (2012) Annu. Rev. Cell Dev. Biol., 28:489-521; Robert-Seilaniantz et al. (2011) Annu. Rev. Phytopathol., 49:317-343).

Nematodes are arguably the most numerous animals on earth. They are ubiquitous in soil and parasitize most plants and animals, and as a result cause agricultural damage of more than $100 B annually worldwide (Blumenthal and Davis (2004) Nat Genet., 36:1246-1247; Mitkowski et al. (2003) Nematology 5:77-83). Plants perceive the presence of nematodes and respond by activating defense pathways. For example, root knot nematodes and rhizobial Nod factors elicit common signal transduction events in Lotus japonicus (Weerasinghe et al. (2005) Proc Natl Acad Sci., 102:3147-3152), and prior inoculation with avirulent (host-incompatible) Meloidogyne incognita in a tomato split-root assay reduced susceptibility to virulent (host-compatible) M. hapla (Ogallo et al. (1995) J Nematol., 27:441-447). Antagonistic effects of entomopathogenic nematodes on plant-parasitic nematodes (Molina et al. (2007) J Nematol., 39:338-342) also may be due to induction of plant defenses, such as expression of pathogenesis-related protein-1 (PR-1) and increased catalase and peroxidase activity, not only in the roots, but also in the leaves (Jagdale et al. (2009) J. Nematology 41:341-341; Jagdale et al. (2009) Biol Control 51:102-109). However, the nature of the nematode-derived signal(s) and the subsequent signaling pathway(s) leading to defense responses have remained unclear.

Ascarosides represent an evolutionarily conserved family of nematode-derived small molecules that serve essential functions in regulating development and social behaviors (Choe et al. (2012) Curr Biol., 22:772-780; Pungaliya et al. (2009) Proc Natl Acad Sci., 106:7708-7713; Srinivasan et al. (2008) Nature 454:1115-1118; Srinivasan et al. (2012) PLoS Biol 10:e1001237; von Reuss et al. (2012) J Am Chem Soc., 134:1817-1824; Butcher et al. (2007) Nat. Chem. Biol., 3:420-422; Golden et al. (1982) Science 218:578-580; Jeong et al. (2005) Nature 433:541-545; Kaplan et al. (2012) PLoS ONE 7:e38735; Ludewig et al. (2013) WormBook, 1-22; Noguez, Jet al. (2012) ACS Chem Biol 7:961-966). Ascarosides are glycosides of the dideoxysugar ascarylose that carry a fatty acid-derived lipophilic side chain and have been identified exclusively from nematodes. For example, in the model organisms *Caenorhabditis elegans*, and *Pristionchus pacificus* as well as in the insect parasitic nematode *Heterorhabditis bacteriophora*, ascarosides regulate entry into stress resistant dispersal or infective larval stages (Bose et al. (2012) Angew Chem Int Ed Engl., 51:12438-12443; Noguez et al. (2012) ACS Chem Biol., 7:961-966; Pungaliya et al. (2009) Proc Natl Acad Sci., 106:7708-7713). Whereas some nematode ascarosides (NAs) are broadly produced among different nematode species, other NAs are highly species-specific or are associated primarily with a specific ecology. For example, the NA ascr#9 is particularly common among entomopathogenic (insect-parasitic) nematodes (Choe et al. (2012) Curr Biol., 22:772-780), whereas the longer-chained ascr#18 is produced by several species of the plant-parasitic genus *Meloidogyne*. Different structural variants are often associated with starkly different activity profiles, and biological activity is frequently observed at very low concentrations (Bose et al. (2012) Angew Chem Int Ed Engl., 51:12438-12443; Pungaliya et al. (2009) Proc Natl Acad Sci., 106:7708-7713; von Reuss et al. (2012) J Am Chem Soc., 134:1817-1824; Izrayelit et al. (2012) ACS Chem Biol., 7:1321-1325).

More than 200 different NA structures from over 20 different nematode species have been identified, demonstrating that NAs are widely distributed in the nematode phylum, including both human-parasitic and plant-parasitic nematodes (Choe et al. (2012) Curr Biol., 22:772-780; von Reuss et al. (2012) J Am Chem Soc., 134:1817-1824; Bose et al. (2012) Angew Chem Int Ed Engl., 51:12438-12443). These results indicated that NAs represent a highly conserved molecular signature of nematodes. Based on these results, it seemed possible that NAs are also perceived by the organisms that nematodes interact with, including their plant and animal hosts as well as nematode-associated microorganisms.

SUMMARY OF THE INVENTION

In accordance with the present invention, a method for modulating disease resistance in plants is provided. An exemplary method comprises contacting a plant or plant part with an effective amount of at least one isolated ascaroside, the ascaroside being effective to increase plant resistance to one or more pathogens, and/or inducing one or more plant defense responses, thereby inhibiting pathogen growth and/or infestation, the method may further comprise measuring at least one plant disease response parameter. In a particular embodiment, the ascaroside is ascr#3, ascr#9, or ascr#18. In a particular embodiment the plant defense response is a basal or innate immune response and is selected from the group consisting of at least one of activation of the systemic acquired resistance, salicylic acid, jasmonate, ethylene, and nitric oxide disease response pathways. In a particular embodiment, the plant disease response parameter is selected from the group consisting of alteration of expression of defense-associated genes (e.g., PR-1, PDF1.2, FRK1, PR4, AOS, PHIL and/or GSTF6), callose deposition, reactive oxygen species production, $Ca^{2+}$ influx, and activation of a MAP kinase (e.g., MPK3, MPK4, and/or MPK6 or their orthologs). In certain instances, at least one ascaroside is effective to prime or induce a plant defense response. In another embodiment, the plant is contacted with two or more ascarosides and/or with salicylic acid which act additively or synergistically to increase plant pathogen resistance and/or inhibit pathogen growth. The resistance induced may be systemic or localized. Disease response parameters to be assessed in accordance with the method described herein include, but are not limited to: alteration of expression of defense-associated genes, callose deposition, reactive oxygen species production, $Ca^{2+}$ influx, and activation of MAP kinase.

A variety of plants may be treated using the methods disclosed herein. Such plants include, without limitation, tobacco, *Arabidopsis*, tomato, barley, potato, sweet potato, yam, cotton, soybean, strawberry, sugar beet, corn, rice, wheat, rye, oat, sorghum, millet, bean, pea, apple, banana, pear, cherry, peach, plum, apricot, almond, grape, kiwi, mango, melon, *papaya*, walnut, hazelnut, pistachio, raspberry, blackberry, loganberry, blueberry, cranberry, orange, lemon, grapefruit, tangerine, lettuce, carrots, onions, broccoli, cabbage, avocado, cocoa, cassava, cotton, and flax. In certain embodiments, the plant is selected from the group consisting of tobacco, *Arabidopsis*, potato, barley, and tomato. In certain embodiments, the pathogen is selected from the group consisting of *Pseudomonas syringae* pv. *tabaci, Pseudomonas syringae* pv. tomato, *Phytophthora infestans, Blumeria graminis* f. sp. *hordei*, the cyst nematode *Heterodera schachtii, Meloidogyne incognita, Meloidogyne hapla*, and turnip crinkle virus. Specific combinations of pathogen and plant (particularly when the ascaroside is asr18) include, without limitation: *Pseudomonas syringae* pv. *tabaci* and tobacco; *Pseudomonas syringae* pv. tomato and *Arabidopsis*; *Phytophthora infestans* and potato or tomato; turnip crinkle virus and *Arabidopsis*; *Blumeria graminis* f. sp. *hordei* and barley; *Heterodera schachtii* or *Meloidogyne incognita* and *Arabidopsis*; and *Meloidogyne hapla* and tomato.

In accordance with another aspect of the instant invention, methods for synthesizing ascr#18 are provided. In a particular embodiment, the method comprises: a) reacting 7-bromoheptene with (R)-propylene oxide to yield (9R)-hydroxy-dec-1-ene; b) reacting the product of step a) with 2,4-di-O-benzoyl-ascarylose-1-(2,2,2-trichloroacetimide) to yield (9R)-(3'R,5'R-dibenzoyloxy-6'S-methyl-(2H)-tetrahydro-pyran-2-yloxy)-dec-1-ene; c) reacting the product of step b) with an alkyl propenoate to yield alkyl (10R)-(3'R,5'R-dibenzoyloxy-6'S-methyl-(2H)-tetrahydropyran-2-yloxy)-undec-2-enoate; d) reacting the product of step c) with a hydroxide to yield ascr#17; and e) hydrogenating ascr#17 to yield ascr#18.

BRIEF DESCRIPTION OF THE DRAWINGS

FIGS. 3A and 3B. Treatment of tobacco roots with ascr#18 enhanced induction by SA of PR-1 transcript (FIG. 3A) and protein (FIG. 3B) in the SA-treated leaves. Roots were treated with NA (0.01 µM) via immersion while the test leaves were simultaneously treated via syringe infiltration with SA (250 µM). PR-1 expression was analyzed 48 hp SA treatment. EF1-α internal control and Coomassie Blue (CB) loading control indicated that all the samples were equally loaded.

FIGS. 4A and 4B. ascr#18-enhanced resistance in tobacco to virulent *Pseudomonas syringae* pv. *tabaci* (Pt). (FIG. 4A) Leaves were treated by syringe infiltration with ascr#18 (0.01 µM) and/or varying concentrations of SA (50 µM or 250 µM) 24 hours before inoculation with P.t. (FIG. 4B) Alternatively, roots were treated via immersion with NA (0.01 µM) while the test leaves were simultaneously treated via syringe infiltration with varying concentrations of SA (50 µM or 250 µM). 24 hours after SA treatment leaves were inoculated with P.t. Bacterial growth was determined 48 hpi. *P<0.05, **P<0.005 (t-test).

FIGS. 5A and 5B. ascr#18 altered PR-1 and PDF1.2 expression in *Arabidopsis*. (FIG. 5A) Leaves of four-weeks old *Arabidopsis* ecotype Col-0 were syringe infiltrated with buffer, SA (50 µM), ascr#18 (0.01 or 0.3 µM) or a mixture of SA (50 µM) and ascr#18. PR-1 and PDF1.2 expression were detected by semi-quantitative PCR. β-tubulin was used as a internal control, which indicated that all the samples were loaded equally. (FIG. 5B) Alternatively, ascr#18 was applied to *Arabidopsis* roots by immersion while the test leaves were simultaneously treated with buffer or SA. Leaves were harvested for RNA 24 hours after treatment.

FIG. 6. ascr#18-enhanced resistance in *Arabidopsis* to virulent *Pseudomonas syringae* pv. tomato DC3000 (Pst). *Arabidopsis* ecotype Col-0 leaves were treated by syringe infiltration with ascr#18 (0.3 µM) and/or SA (50 µM) 24 hours prior to inoculation with Pst. Bacterial growth was assayed 72 hpi. *P<0.05, P<0.006, *P<0.006 (t-test).

FIG. 10A: Photographs of potato inoculated leaflets 5 dpi. Inoculated area is circled. FIG. 10B: Size of lesion caused by *P. infestans* at 5 dpi. *P<0.05 (t-test).

FIG. 11A. Photographs of tomato inoculated leaflets 6 dpi. FIG. 11B. Size of lesion caused by *P. infestans* at 4 dpi and 5 dpi in the two tomato varieties. FIG. 11C. Sporangia number per ml counted at 6 dpi. *P<0.0005 (t-test).

FIG. 12A: Various methods of treatment with ascr#18 enhanced resistance in tobacco to *P. syringae* pv *tobaci*. Tobacco leaves were treated by syringe infiltration with ascr#18 (0.01 µM; NA). Salicylic acid (50 µM; SA) was syringe infiltrated in leaves 24 hours after treatment with ascr#18. Inoculations of *P. syringae* pv *tabaci* was done 48 hours after ascr#18 and bacterial growth was determined at 2 days post inoculation. *P<0.05 (t-test). FIG. 12B: Tobacco plants were sprayed with ascr#18 (0.01 µM) 24 hours (a) or 48 hours (b) before inoculation with *P. syringae* pv *tabaci*. *P<0.05 (t-test). FIG. 12C: Roots of tobacco plants were immersed in a solution of ascr#18 (0.01 µM or 0.03 µM), SA (250 µM), BTH/actigard (0.075 g/L), or a combination thereof at the indicated times prior to inoculation with *P. syringae* pv *tabaci*. *P<0.05 (t-test).

FIG. 13A: Root treatment with ascr#18 enhanced resistance in *Arabidopsis* to *P. syringae* pv tomato. Roots of *arabidopsis* plants were immersed in a solution of ascr#18 (0.3 µM, 1 µM, or 5 µM) 24 hours prior to inoculation with *P. syringae* pv tomato. *P<0.05, ***P<0.0005 (t-test). FIG. 13B: Shows the induction of PR-1 and FRK1 in ascr#18 treated *Arabidopsis* roots. FIG. 13C: Shows ascr#18 enhances resistance of Arabidposis to the cyst nematode *Heterodera schachtii*. *P<0.02 (t-test). FIG. 13D: Treatment with ascr#18 enhanced resistance in *Arabidopsis* to *P. syringae* pv tomato. *Arabidopsis* leaves were treated by syringe infiltration with ascr#18 (0.3 µM), easc#18 (0.3 µM) and/or SA (50 µM) 24 hours prior to inoculation with *P. syringae* pv tomato. Bacterial growth was assayed 3 dpi. *P<0.01, P<0.001, *P<0.0001, ****P<0.00005 (t-test). FIG. 13E: Shows ascr#3 altered PR-1 and PDF1.2 expression in *Arabidopsis*. 50 µM SA was applied with or without ascr#3. Tubulin was used as an internal control. FIG. 13F: Shows ascr#9 altered PR-1 and PDF1.2 expression in *Arabidopsis*. 50 µM SA was applied with or without ascr#9. Tubulin was used as an internal control. FIG. 13G: Treatment with ascr#3 enhanced resistance to *P. syringae* pv tomato. *Arabidopsis* leaves were treated by syringe infiltration with ascr#3 (0.3 µM) and/or SA (50 µM) 24 hours prior to inoculation with *P. syringae* pv. tomato. Bacterial growth was assayed 3 dpi. *P<0.05, **P<0.001 (t-test). FIG. 13H: Shows ascr#10 altered PR-1 and PDF1.2 expression in *Arabidopsis*. Tubulin was used as an internal control. FIG. 13I: Shows oscr#9 altered PR-1 and PDF1.2 expression in *Arabidopsis*. Tubulin was used as an internal control.

FIG. 14A: Shows the change in pH of tomato suspension cells treated for 90 minutes with ethanol, Flg22 peptide (positive control), or with the indicated concentrations (µM) of ascr#18. FIG. 14B: Treatment with easc#18 enhanced resistance in tomato to *Botrytis cinerea*. Tomato plants were treated via root immersion with water (−) or with 0.01 µM ascr#18 or 0.01 µM easc#18 48 hours before inoculation with the virulent B05.01 strain of *B. cinerea* using a detached leaflet assay. The size of the lesion caused by *B. cinerea* was determined at 3 dpi. FIG. 14C: Provides photographs of the *B. cinerea* lesions at 3 dpi. FIG. 14D: Treatment with either ascr#18 or easc#18 enhanced resistance in tomato to *P. infestans*. Tomato cv. Rio Grande plants were treated via root immersion with water (−) or with 0.01 µM of ascr#18 or easc#18, or a combination of both 48 hours before inoculation with *P. infestans* using a detached leaflet assay. Size of lesion caused by *P. infestans* was determined at 5 dpi. ***P<0.0009 (t-test). FIG. 14E: Sporangia number of *P. infestans* was determined at 6 dpi. *P<0.0009, P<0.001, *P<0.01 (t-test). FIG. 14F: Tomato suspension cells were treated with either ethanol (ETOH) or ascarosides at the concentration indicated and the increase of the pH in the media was monitored for 120 minutes after adding the ascarosides. FIG. 14G: Tomato cv. M82 plants were treated via root immersion with water (−) or with 1 µM ascr#9 48 hours before inoculation with virulent US22 strain of *Phy-*

*tophthora infestans* using a detached leaflet assay. Size of lesion caused by *P. infestans* was determined at 7 dpi. *P<0.0005 (t-test).

Figure 15A:
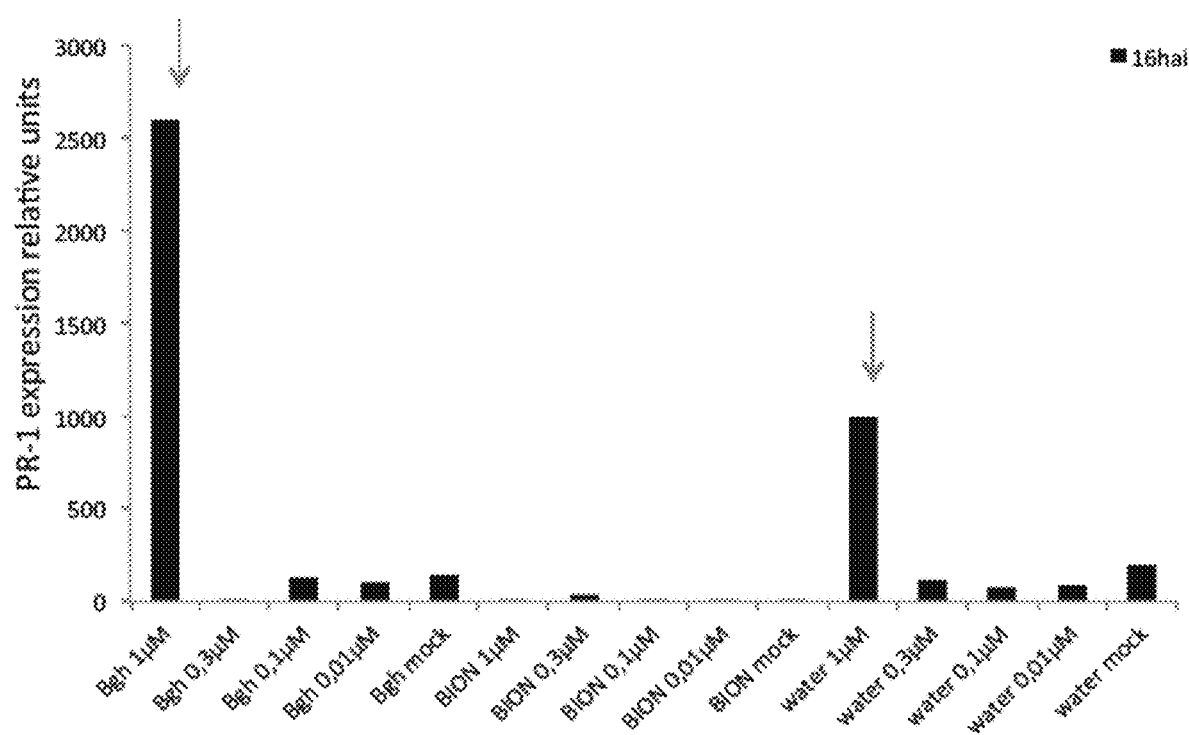
Figure 15B:
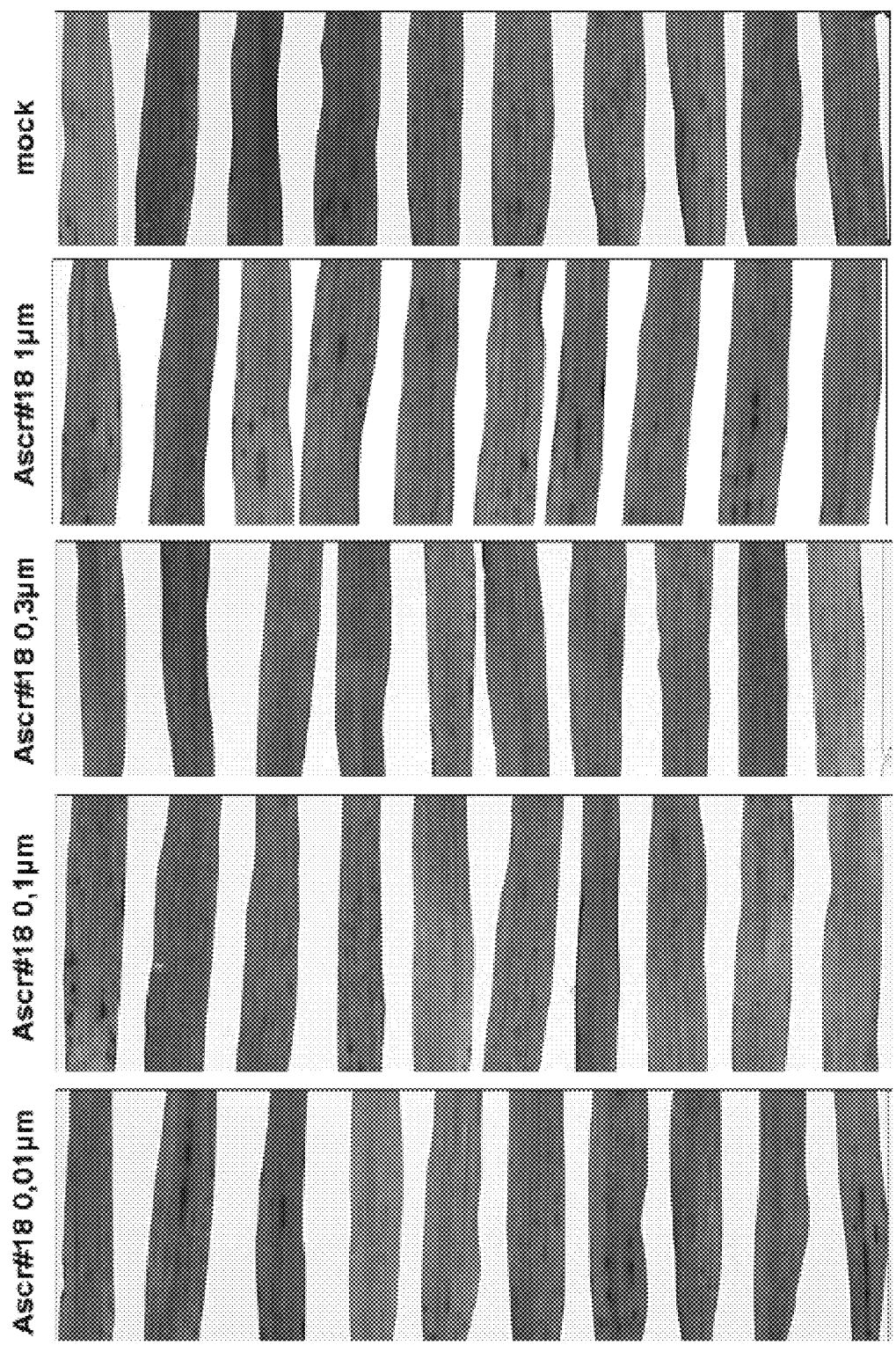
Figure 15C:
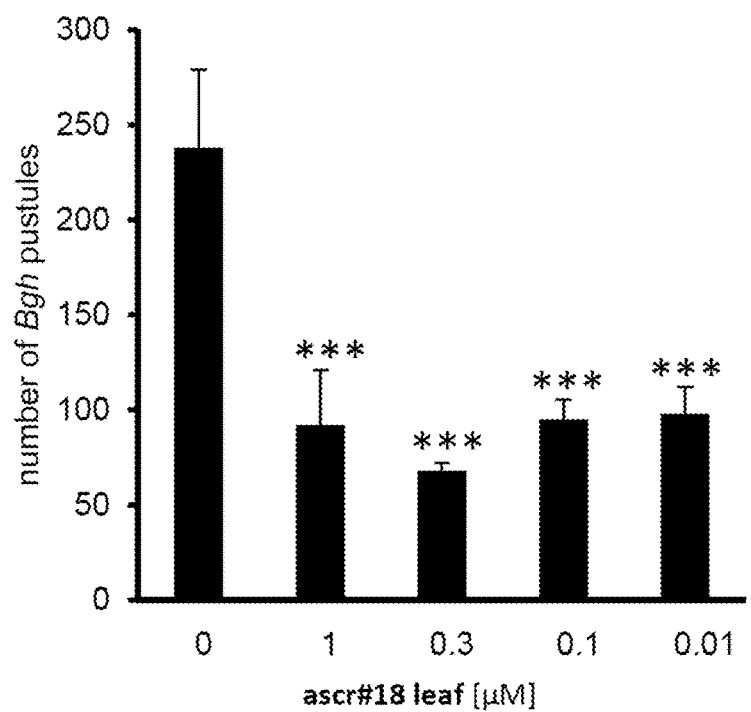
Figure 15D:
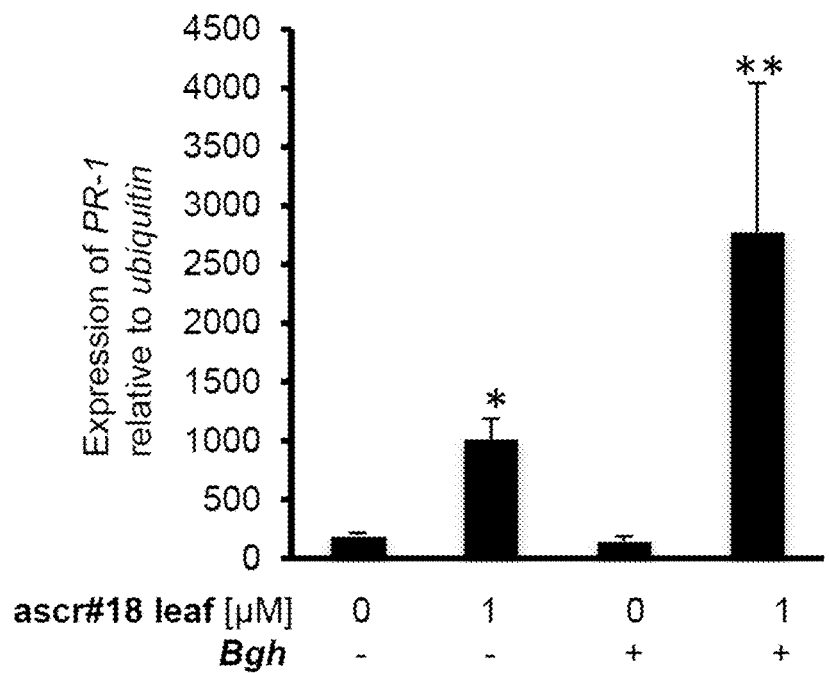

FIGS. 15A, 15B, 15C, and 15D. FIG. 15A: Shows the induction of PR-1 gene in barley leaves 48 hours after treatment with 1 μM ascr#18. FIG. 15B: Treatment with ascr#18 of barley leaves enhanced resistance to Blumeria *graminis* f. sp. *hordei* (Bgh). Barley leaves were sprayed with the indicated concentrations of ascr#18 48 hours before inoculation with Blumeria *graminis* f. sp. *hordei* (Bgh). Photograph of barley leave segments infected with Bgh were taken at 7 days post inoculation (dpi). FIG. 15C: Provides the number of Bgh pustules counted at 7 dpi. FIG. 15D: shows ascr#18 increased PR-1 gene expression and resistance in barley. Leaves of barley plants were sprayed with water or ascr#18 (1 μM). Plants were inoculated with Bgh 48 hours post treatment. Leaves were collected at 16 hpi and used to extract RNA for qRT-PCR analysis. Data are average±SD (n=3, where n denotes the number of independent samples). (*P≤0.05; P≤0.005; *P≤0.0005, two-tailed t-test).

Figure 16A:
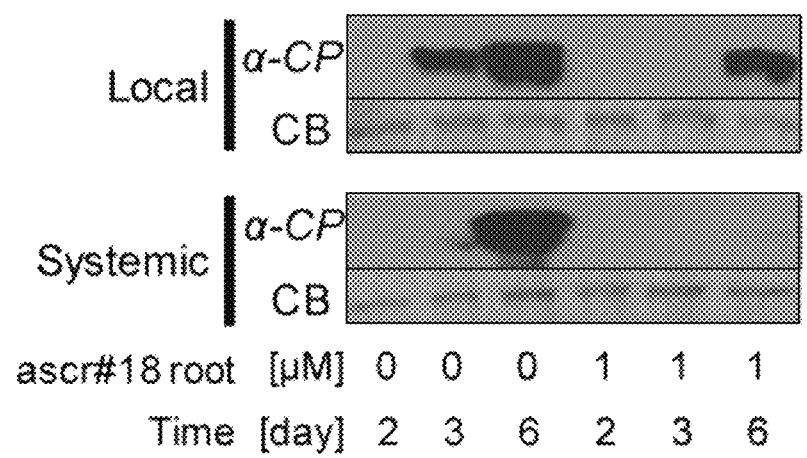
Figure 16B:
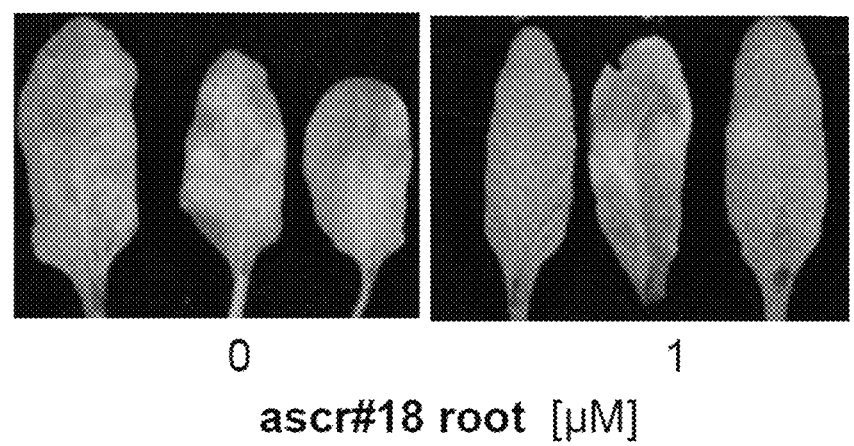
Figure 16C:
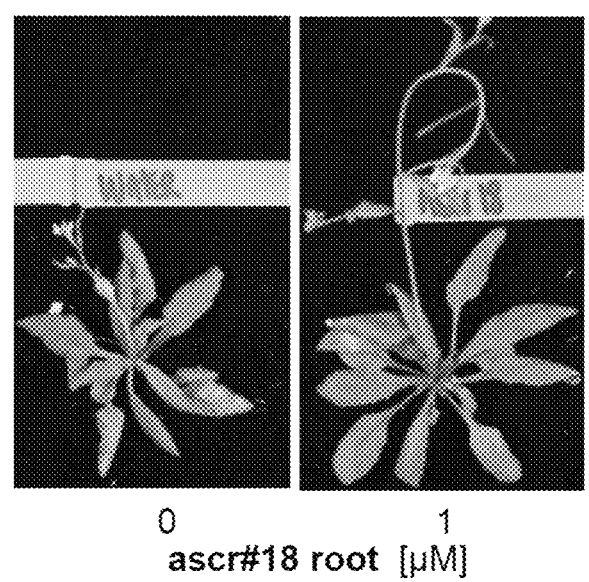
Figure 16D:
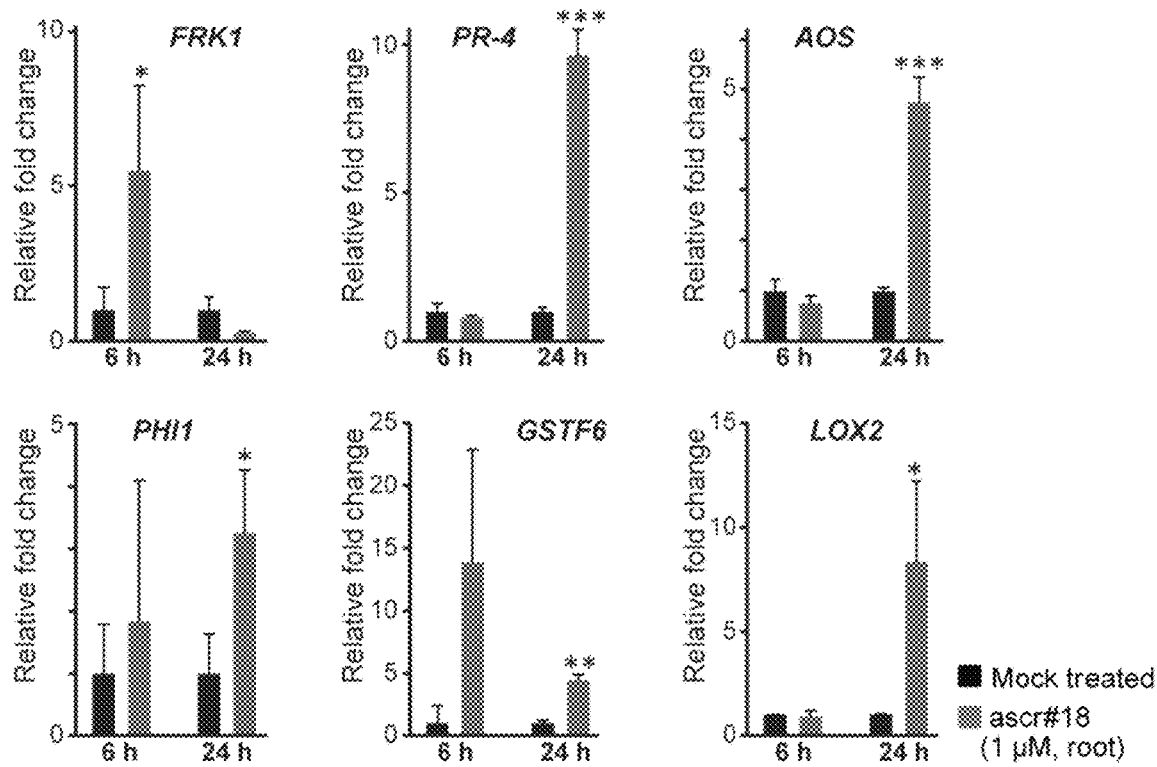
Figure 16E:
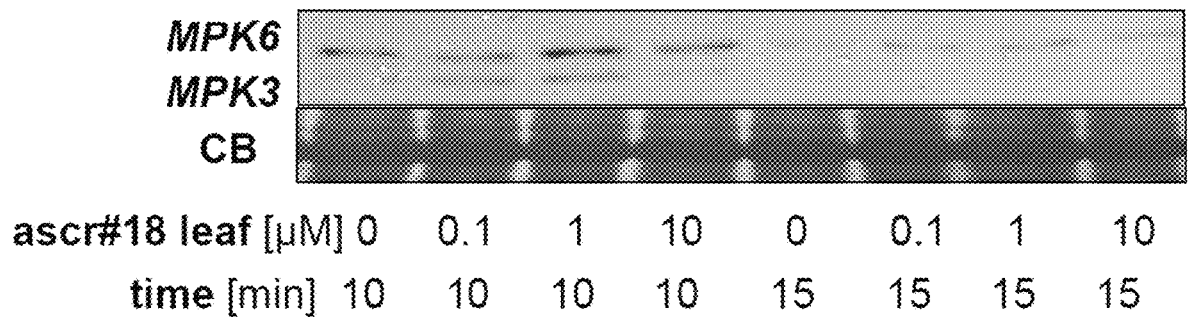
Figure 16F:
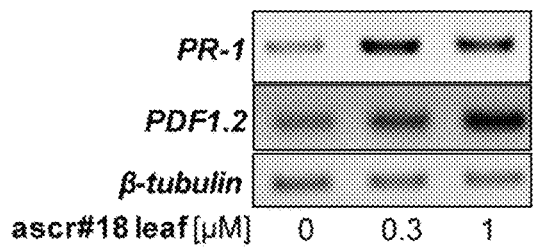
Figure 16G:
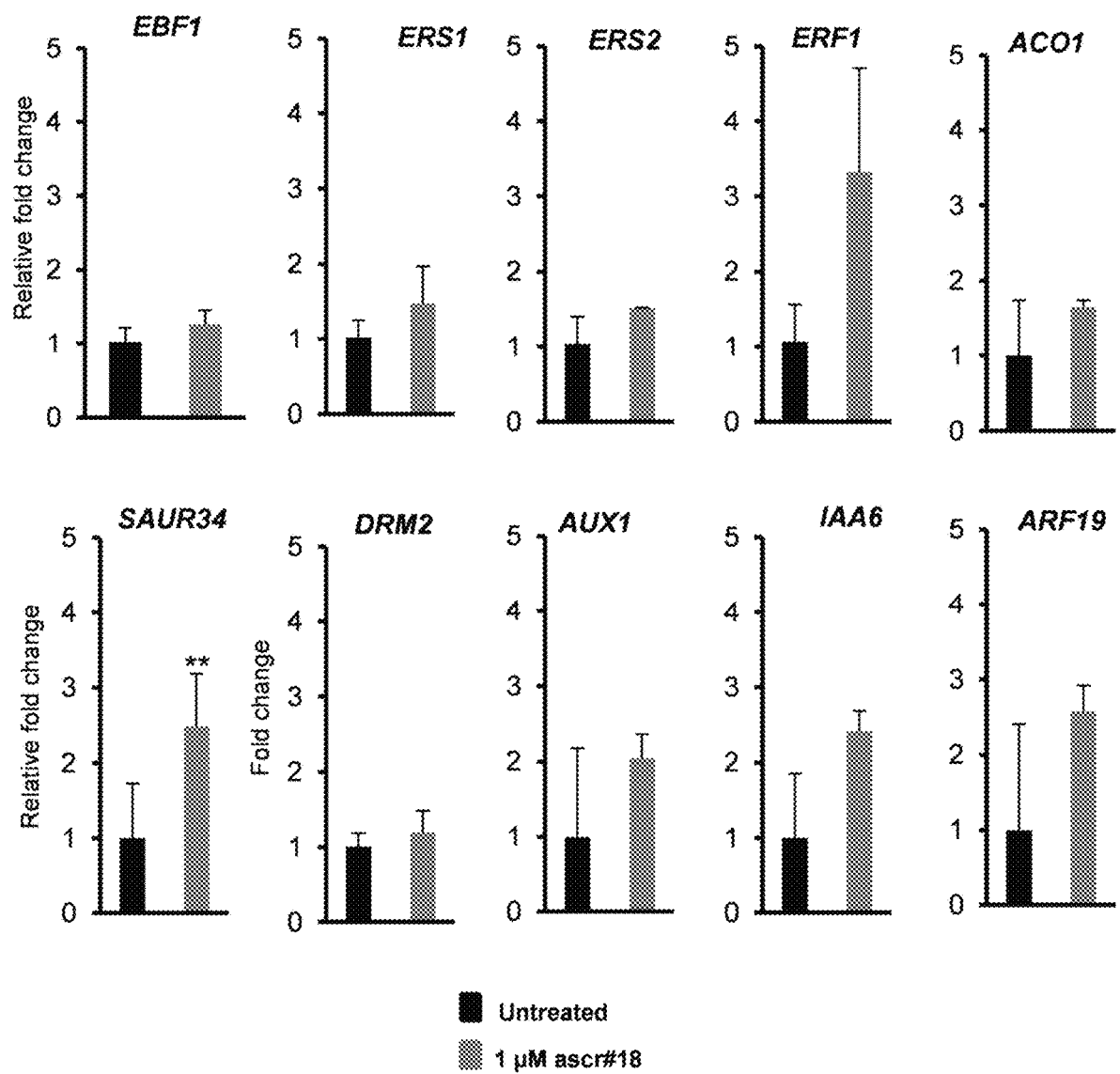
Figure 16H:
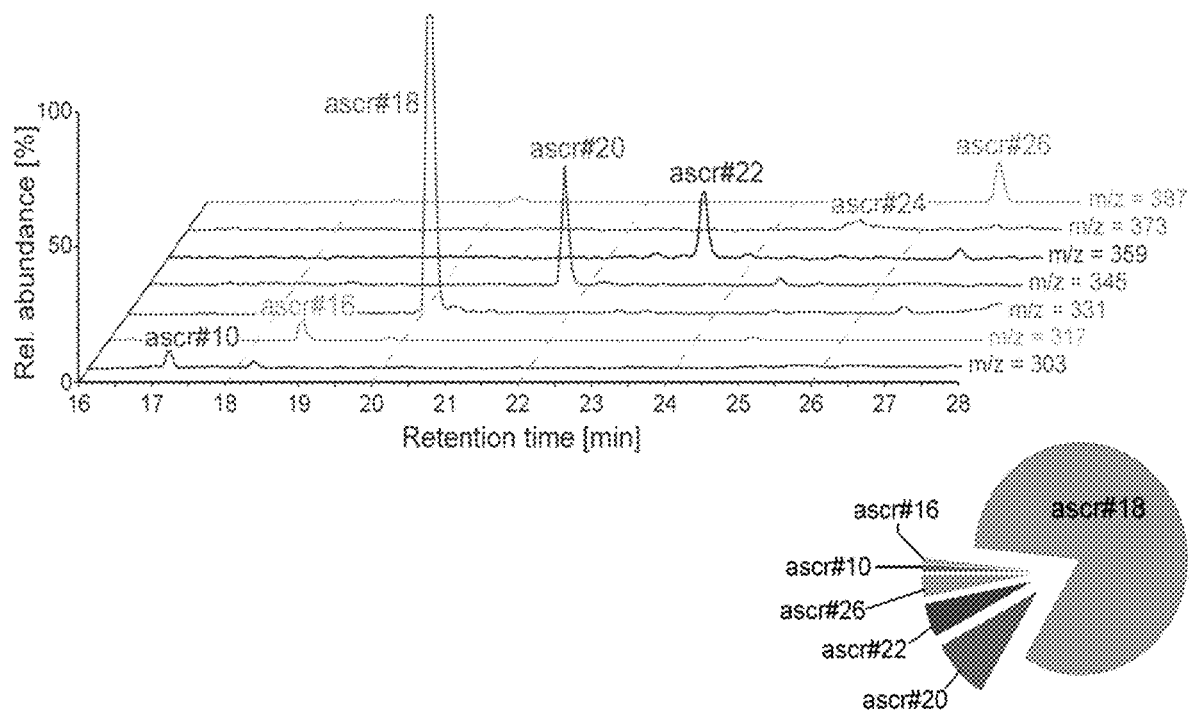
Figure 16I:
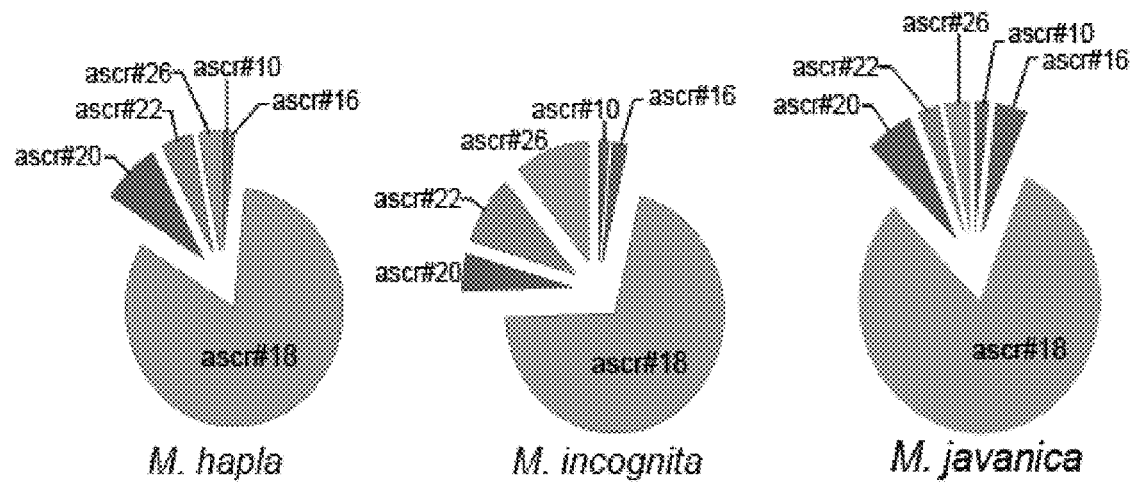

FIGS. 16A, 16B, 16C, 16D, 16E, 16F, 16G, 16H, and 16I. FIGS. 16A, 16B, 16C: Root treatment with 1 μM ascr#18 solution enhanced basal resistance to Turnip Crinkle Virus (TCV). Three biological samples per time point were used and this analysis was done two times with similar results. (FIG. 16A) Quantification of TCV coat protein (CP) was performed with 20-fold dilution of the total protein extracts of the inoculated (local) and uninoculated (systemic) leaves at 2, 3, and 6 days post inoculation (dpi) using immunoblot analysis with the aCP antibody. Coomassie blue staining (CB) was performed for loading control of the samples. Inoculated (local) leaves corresponding to three plants untreated (0) and treated (1) with ascr#18 were excised and photographed at 6 dpi (FIG. 16B). TCV symptoms in the entire plants were photographed at 6 dpi (FIG. 16C). FIG. 16D: Transcript levels as measured by semi-quantitative RT-PCR (qRT-PCR) of defense gene markers in leaves from plants root-pretreated with ascr#18 (1 μM). Gene transcript levels of FRK1 were determined at 6 hpt and PHI1, PR-4, AOS, GSTF6, and LOX2 transcripts levels at 24 hpt. Data are average±SD (n=3). FIG. 16E: Activation of MAPKs MPK3 and MPK6 in *Arabidopsis* after leaf treatment with ascr#18. *Arabidopsis* plants were infiltrated via syringe with buffer or various concentrations of ascr#18 (0.1, 1, and 10 μM). MAPK activation was detected at 10 and 15 minutes after treatment by immunoblot analyses using anti-phospho-p44/42-MAPK antibody. Coomassie Blue (CB) stained membrane served as a loading control. FIG. 16F: Induction of SA and JA marker genes PR-1 and PDF1.2 after syringe infiltration of leaves with ascr#18, as measured by qRT-PCR. β-tubulin was used as internal control. *P≤0.05; P≤0.005; *P≤0.0005, two-tailed t-test. FIG. 16G: Transcript levels as measured by qRT-PCR of ethylene- and auxin-responsive gene markers in leaves from plants root-pretreated with ascr#18 (1 μM). Gene transcript levels of EBF1, ERS1, ERS2, ERF1, ACO1, SAUR34, DRM2, AUX1, IAA6 and ARF19 were determined at 24 hours post pretreatment (hpt). **P≤0.005, two-tailed t-test. FIG. 16H: HPLC-MS analysis of *M. hapla* exo-metabolome samples, showing ion chromatograms scaled to 100% of the ascaroside peak corresponding to m/z=[M-H]⁻ for seven detected ascarosides. Relative quantitative distribution as determined by HPLC-MS is also shown. FIG. 16I: Relative abundances of identified ascarosides, as determined from integration of HPLC-MS ion chromatograms, in the exo-metabolomes of three *Meloidogyne* species. In addition, all three species also produce trace amounts of ascr#24.

Figure 17A:
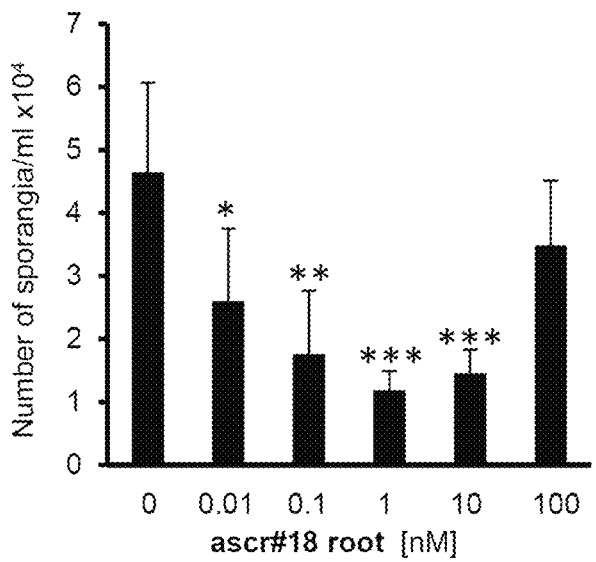
Figure 17B:
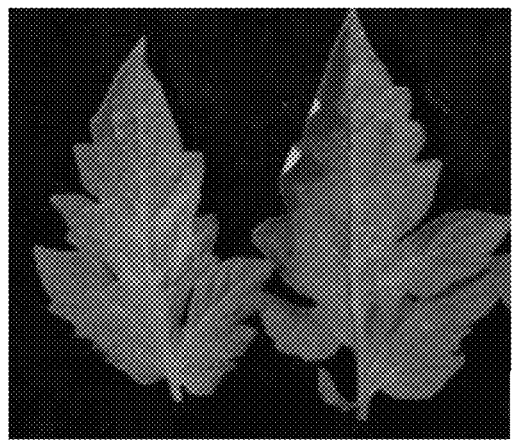
Figure 17C:
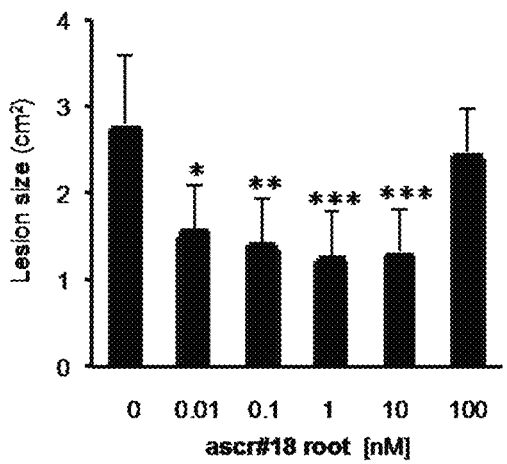
Figure 17D:
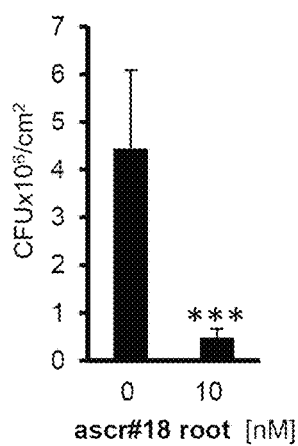

FIGS. 17A, 17B, 17C, 17D, 17E, and 17F. Ascr#18 activated defense responses and enhanced resistance in Solanaceous crops. FIG. 17A: Determination of effective concentrations of ascr#18 for enhanced disease resistance. Tomato cv. M82 plants were treated via root immersion with water (0) or different concentrations of ascr#18 (0.01, 0.1, 1, 10, 100 nM) 48 hours before inoculation with *P. infestans* (US22) (4000 sporangia/ml) using a detached leaflet assay. Four plants were used per time point and 4 leaves per plant were detached for the inoculation assay. (FIG. 17A) Sporangia numbers were count at 6 dpi to assess disease symptoms. Data are average±SD (n=16, where n denotes the number of independent samples. Pictures of the blighted area in M82 leaves were taken at 6 dpi (FIG. 17B). FIG. 17C: Lesion size was determined at 5 dpi. to assess disease symptoms. Data are average±SD (n=16, where n denotes the number of independent samples). FIG. 17D: Effect of ascr#18 on resistance to Pst in tomato cv. M82. Tomato plants were treated via root immersion with water (0) or with 10 nM of ascr#18 48 hours before vacuum infiltration with Pst DC3000. Bacterial growth was assayed at 4 dpi. Data are average±SD (n=6, where n denotes the number of independent samples).

Figure 17E:
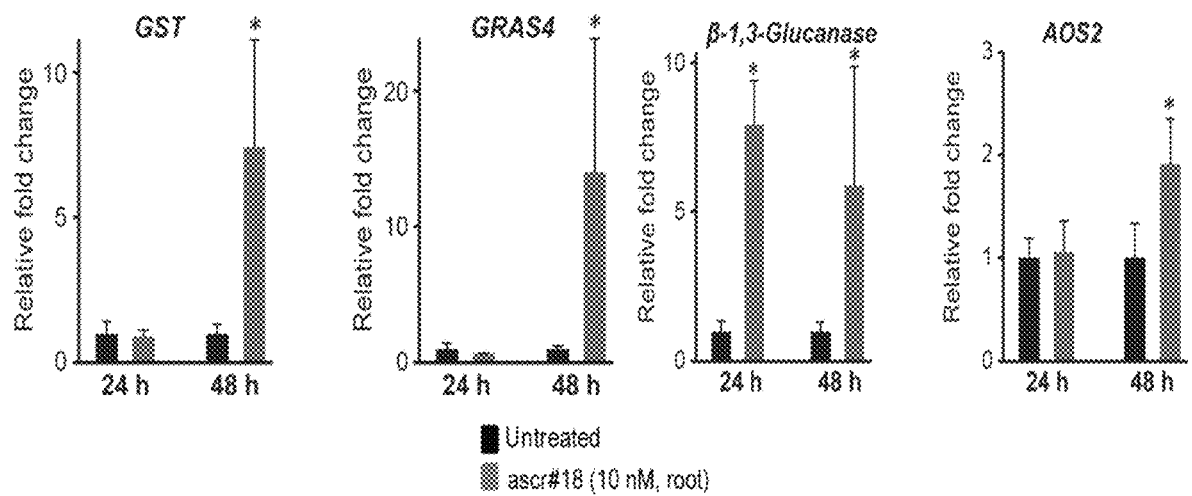
Figure 17F:
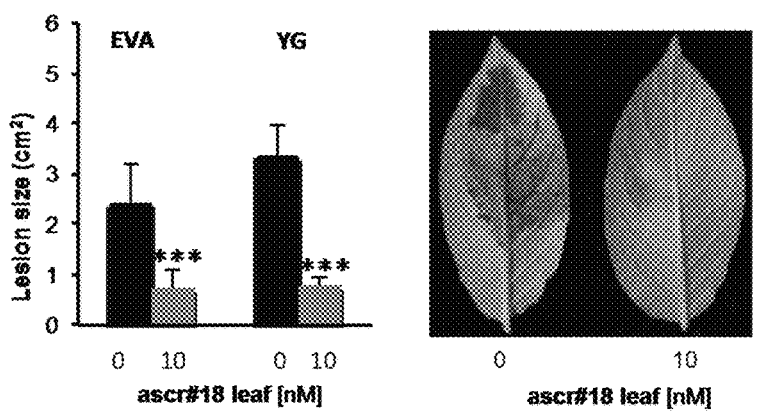

FIG. 17E: Induction of defense response genes in tomato leaves 24 and 48 hours after root-pretreatment with ascr#18. Data are average±SD (n=3). *P≤0.05; P≤0.005; *P≤0.0005, two-tailed t-test. FIG. 17F: ascr #18 treatment of potato protects against *P. infestans*-induced late blight. Lesion size was determined at 5 dpi to assess disease symptoms and pictures of the blighted area in potato cultivar Yukon Gold were taken at 6 dpi with *P. infestans*. Data are average±SD (n=10, where n denotes the number of independent samples). *P≤0.05; P≤0.005; *P≤0.0005, two-tailed t-test.

Figure 18A:
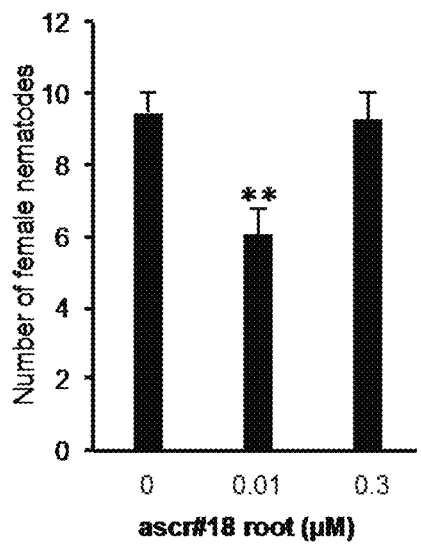
Figure 18B:
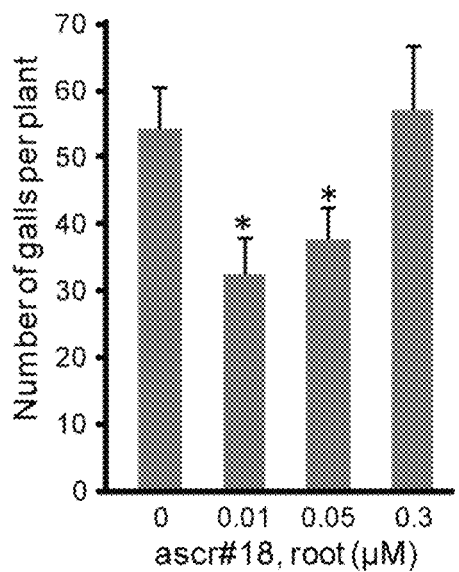
Figure 18C:
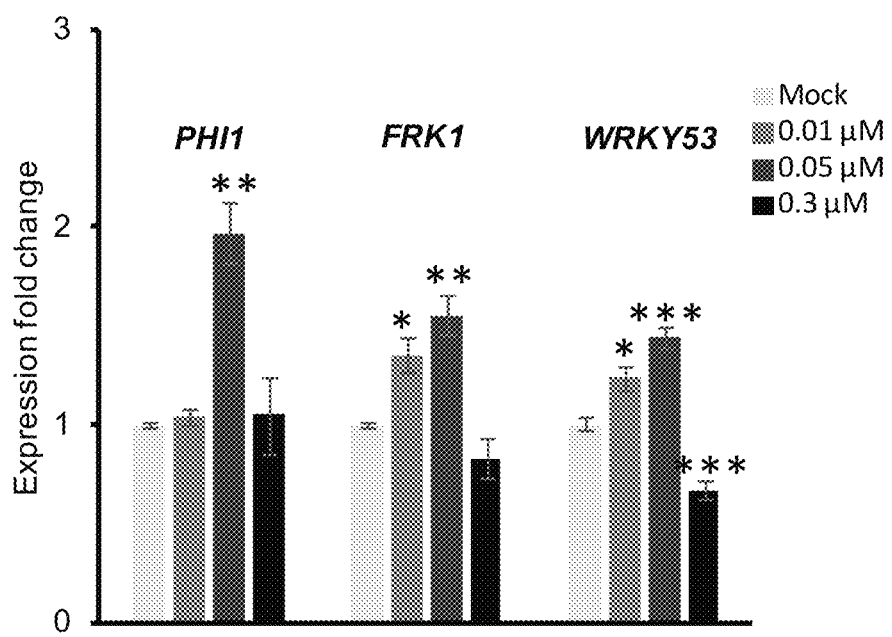

FIGS. 18A, 18B, and 18C: Effect of Ascr#18 on *Arabidopsis* to cyst nematode *Heteroderas schachtii*. FIG. 18A: Ten days old *Arabidopsis* seedlings were pretreated with buffer or 0.01 and 0.3 μM of ascr#18 for 48 hours before inoculation with about 200 freshly hatched and surface-sterilized juveniles per seedlings. The numbers of females were counted four weeks after inoculation. FIG. 18B: Effect of ascr#18 on *Arabidopsis* susceptibility to root knot nematode (*M. incognita*). Ten day-old *Arabidopsis* seedlings were pretreated with the indicated ascr#18 concentrations for 48 hours before inoculation with approximately 300 freshly hatched and surface-sterilized juveniles per seedlings. The numbers of galls were counted under microscope six weeks after inoculation. FIG. 18C: Eight days old *Arabidopsis* seedlings were treated by root bathing using the indicated concentrations of ascr#18. Root samples were collected 6 hours after treatment for RNA extraction. Transcript levels of PHI1, FRK1 and WRKY53 were determined by qRT-PCR and normalized to endogenous UFP (AT4G01000). *P≤0.05; P≤0.005; *P≤0.0005, two-tailed t-test.

DETAILED DESCRIPTION OF THE INVENTION

Nematode ascarosides (NAs), a highly conserved family of nematode-derived small signaling molecules, act as immunosuppressors in mice and induce morphological changes in fungi that prey on nematodes. The results presented herein indicate that NAs also alter plant defense responses to microbial pathogens. Since nematodes are ubiquitous in soil, they contact virtually all plants via the roots. Identifying the mechanisms by which NAs alter defense responses provides novel insights into plant immunity and facilitates the development of strategies to enhance plant protection against nematodes and other pathogens. Thus, the present invention will also lead to enhanced food security and reduced pesticide use, thereby improving economic and environmental sustainability of agriculture.

A selection of naturally-occurring NA variants as well as additional synthetic variants and derivatives can be synthesized and tested for defense response-modulating activity in tobacco, *Arabidopsis*, tomato, potato, and other crop plant species, with the most active selected for further development. To further characterize the molecular mechanism(s) by which NAs modulate plant defense responses, several avenues will be explored. Since NA activates salicylic acid (SA)-mediated and jasmonic acid (JA)-mediated defenses and enhances resistance to biotrophic pathogens, NA's signaling mechanism(s) will be investigated using SA-, JA-, and/or ethylene (ET)-defective mutants and global transcriptome analyses. NA's ability to enhance resistance to necrotrophic and biotrophic pathogens, mediated via JA/ET- or SA-dependent pathways, respectively, can be determined, as well as its effect on resistance gene-mediated immunity to microbes and resistance to cyst and root-knot nematodes. To determine whether NAs induce systemic resistance via NA translocation, radiotracer studies can be performed. NA's applicability to multiple crops can be further tested by analyzing defense gene expression and disease resistance.

The following definitions are provided to facilitate an understanding of the present invention.

The term "ascaroside" refers to any of a group of glycolipids, containing the sugar ascarylose, found in most nematode worms.

The term "pathogen" refers to any bacterium, fungus, oomecyte, virus, nematode (e.g., cyst or root knot nematode), or insect, with pathogenic effects on the plant.

The term "pathogen-inoculated" refers to the inoculation of a plant with a pathogen.

The term "disease defense response" refers to a change in metabolism, biosynthetic activity or gene expression that enhances a plant's ability to suppress the replication and spread of a pathogen (i.e., to resist the pathogen). Examples of plant disease defense responses include, but are not limited to, production of low molecular weight compounds with antimicrobial activity (referred to as phytoalexins) and induction of expression of defense (or defense-related) genes, whose products include, for example, peroxidases, cell wall proteins, proteinase inhibitors, hydrolytic enzymes, pathogenesis-related (PR) proteins and phytoalexin biosynthetic enzymes, such as phenylalanine ammonia lyase and chalcone synthase (Dempsey and Klessig, 1995; Dempsey et al., 1999). Such defense responses appear to be induced in plants by several signal transduction pathways involving secondary defense signaling molecules produced in plants. Certain of these defense response pathways are SA dependent, while others are partially SA dependent and still others are SA independent. Agents that are known to induce disease defense responses in plants include, but are not limited to: (1) microbial pathogens, such as fungi, oomycetes, bacteria and viruses and (2) microbial components and other defense response elicitors, such as proteins and protein fragments, small peptides, β-glucans, elicitins, harpins and oligosaccharides. Defense signaling is mediated through several plant hormones, such as SA, ethylene, and jasmonates.

The terms "defense-related genes" and "defense-related proteins" refer to genes or their encoded proteins whose expression or synthesis is associated with or induced after infection with a pathogen.

Treatment of the plants and soil with the ascarosides described herein may be carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

Depending on the plant species or plant cultivars, their location and growth conditions (soils, climate, vegetation period, diet), the treatment according to the invention may also result in super-additive ("synergistic") effects. Thus, for example, reduced application rates and/or a widening of the activity spectrum and/or an increase in the activity of the substances and compositions to be used, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products that exceed the effects which were actually to be expected may occur.

The ascarosides described herein may be used in unchanged form or together with an agronomically acceptable carrier. The term "agronomically acceptable carrier" includes any carrier suitable for administration to a plant or soil, for example, customary excipients in formulation techniques, such as solutions (e.g., directly sprayable or dilutable solutions), emulsions, (e.g., emulsion concentrates and diluted emulsions), wettable powders, suspensions, soluble powders, powders, dusts, pastes, soluble powders, granules, suspension-emulsion concentrates, encapsulation into polymeric materials, coatable pastes, natural and synthetic materials impregnated with active compound and microencapsulations in polymeric substances. These formulations are produced in a known manner, for example by mixing the compounds with agronomically acceptable carrier, such as liquid solvents or solid carriers, optionally with the use of surfactants, including emulsifiers, dispersants, and/foamformers.

If the agronomically acceptable carrier is water, it may also possible to employ, for example, organic solvents as auxiliary solvents. Suitable liquid solvents include, for example, aromatics (e.g., xylene, toluene and alkylnaphthalenes); chlorinated aromatics or chlorinated aliphatic hydrocarbons (e.g., chlorobenzenes, chloroethylenes and methylene chloride); aliphatic hydrocarbons (e.g., cyclohexane); paraffins (e.g., petroleum fractions, mineral and vegetable oils); alcohols (e.g., butanol or glycol and also their ethers and esters); ketones (e.g., acetone, methyl ethyl ketone, methyl isobutyl ketone and cyclohexanone) and strongly polar solvents (e.g., dimethylformamide and dimethyl sulphoxide). It is preferred that non toxic carriers be used in the methods of the present invention.

Suitable solid agronomically acceptable carriers include, for example, ammonium salts and ground natural minerals (e.g., kaolins, clays, talc, chalk, quartz, attapulgite, montmorillonite and diatomaceous earth); ground synthetic minerals (e.g., highly disperse silica, alumina and silicates); crushed and fractionated natural rocks (e.g., calcite, marble, pumice, sepiolite and dolomite); synthetic granules of inorganic and organic meals; granules of organic material (e.g., sawdust, coconut shells, maize cobs and tobacco stalks).

Suitable emulsifiers and foam-formers include, for example, nonionic and anionic emulsifiers (e.g., polyoxyethylene fatty acid esters, polyoxyethylene fatty alcohol ethers, for example, alkylaryl polyglycol ethers, alkylsulphonates, alkyl sulphates and arylsulphonates) protein hydrolysates.

Suitable dispersants include, for example, lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives may include, for example, mineral and vegetable oils.

Colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc may also be included in the agronomically acceptable carrier.

The plant defense inducing compositions may be administered to the plant or soil by any techniques known in the art, including, for example, spraying, atomizing, dusting, scattering, coating or pouring. One of skill in the art would be able to determine the appropriate technique for administration without undue experimentation according the specific pest to be combated, the specific chemical composition and formulation of the compound being employed, the method of applying the compound/formulation, and the locus of treatment.

In one embodiment, the inducers of plant defense responses may be administered by foliar application. In another embodiment, the compositions may also reach the plants through the root system via the soil (systemic action) by drenching the locus of the plant with a liquid preparation or by incorporating the substances into the soil in solid form, e.g., in the form of granules (soil application). In rice cultivations, these granules may be dispensed over the flooded paddy field. The compositions of the invention may also be applied to tubers or seed grain, for example, by soaking, spraying or drenching the seed grain or tubers in a liquid ascaroside containing composition or by coating the tubers or seed grain with a solid ascaroside composition.

The compositions disclosed herein generally comprise between 0.1 and 95% by weight of active compound, preferably between 0.5 and 90%. Favorable application rates are, in general, 0.1 g to 2 kg of active substance (AS) per hectare (ha), for example, 1 g to 1 kg AS/ha or 2 g to 600 g AS/ha. For application of tubers or seed grain, dosages of 1 mg to 1 g active substance per kg of seed grain or tubers may be used.

The term "substantially pure" refers to a preparation comprising at least 50-60% by weight of a given material (e.g., small molecule, nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC-MS analysis, and the like).

The term "functional" as used herein implies that the ascaroside is functional for the recited assay or purpose, e.g., for modulation of immunity or disease resistance in plants.

Plants and plant cells to be treated using the compositions and methods described herein include, but are not limited to, tobacco, *Arabidopsis*, tomato, barley, potato, sweet potato, yam, cassava, cotton, soybean, strawberry, sugar beet, corn, rice, wheat, rye, oat, sorghum, millet, canola, bean, pea, apple, banana, pear, cherry, peach, plum, apricot, almond, grape, kiwi, mango, melon, *papaya*, walnut, hazelnut, pistachio, raspberry, blackberry, loganberry, blueberry, cranberry, orange, lemon, grapefruit, tangerine, lettuce, carrots, onions, broccoli, cabbage, avocado, and cocoa.

The ascarosides for use in the methods described herein can vary in structure. The term "alkyl" refers to an aliphatic hydrocarbon group which may be a linear, branched, or cyclic hydrocarbon structure or combination thereof. Representative alkyl groups are those having 24 or fewer carbon atoms, for instance, methyl, ethyl, n-propyl, ipropyl, n-butyl, s-butyl, t-butyl, n-pentyl, i-pentyl, n-hexyl, and the like. Lower alkyl refers to alkyl groups having about 1 to about 6 carbon atoms in the chain. Branched alkyl means that one or more lower alkyl groups such as methyl, ethyl, or propyl are attached to a linear alkyl chain.

The statement that alkyl is intended to include linear, branched, or cyclic hydrocarbon structures and combinations thereof means that an "alkyl" group also includes the following combination of linear and cyclic structural elements

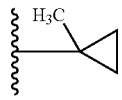

(and similar combinations).

"Alkenyl" means an alkyl, as defined above, containing at least one double bond between adjacent carbon atoms. Alkenyls include both cis and trans isomers. Branched alkenyl means that one or more lower alkyl groups such as methyl, ethyl, or propyl are attached to a linear alkenyl chain. Representative straight chain and branched alkenyls are those having about 2 to about 6 carbon atoms in the chain, for instance, ethylenyl, propylenyl, I-butenyl, 2-butenyl, isobutylenyl, I-pentenyl, 2-pentenyl, 3-methyl-1-butenyl, 2-methyl-2-butenyl, 2,3-dimethyl-2-butenyl, and the like.

The term "halogen" refers to fluoro, chloro, bromo, and iodo.

The term "halo alkyl" refers to a branched or straight-chain alkyl as described above, substituted with one or more halogens.

The term "haloalkenyl" refers to a branched or straight-chain alkenyl as described above, substituted with one or more halogens.

The term "aryl" means an aromatic monocyclic or multi-cyclic (polycyclic) ring system of 6 to about 19 carbon atoms, for instance, about 6 to about 10 carbon atoms, and includes arylalkyl groups. Representative aryl groups include, but are not limited to, groups such as phenyl, naphthyl, azulenyl, phenanthrenyl, anthracenyl, fluorenyl, pyrenyl, triphenylenyl, chrysenyl, and naphthacenyl.

The term "arylalkyl" means an alkyl residue attached to an aryl ring. Examples are benzyl, phenethyl, and the like.

The term "heteroaryl" means an aromatic monocyclic or multi-cyclic ring system of about 5 to about 19 ring atoms, for instance, about 5 to about 10 ring atoms, in which one or more of the atoms in the ring system is/are element(s) other than carbon, for example, nitrogen, oxygen, and/or sulfur.

As is well known to those skilled in the art, heteroaryl rings have less aromatic character than their all-carbon counter parts. Thus, for the purposes of the invention, a "heteroaryl" group need only have some degree of aromatic character. For instance, in the case of multi-cyclic ring systems, only one of the rings needs to be aromatic for the ring system to be defined as "heteroaryl". Exemplary heteroaryls contain about 5 to 6 ring atoms. The prefix aza, oxa, thia, or thio before heteroaryl means that at least a nitrogen, oxygen, or sulfur atom, respectively, is present as a ring atom. A nitrogen, carbon, or sulfur atom in the heteroaryl ring may be optionally oxidized; the nitrogen may optionally be quaternized. Representative heteroaryls include, but are not limited to, purinyl, pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, quinolinyl, isoquinolinyl, quinazolinyl, cinnolinyl, pthalazinyl, quinoxalinyl, and the like.

The terms "cycloalkyl" and "cycloalkenyl" refer to a non-aromatic, saturated (cycloalkyl) or unsaturated (cycloalkenyl), mono- or multi-cyclic ring system of about 3 to about 8 carbon atoms, for instance, about 5 to about 7 carbon atoms. Exemplary cycloalkyl and cycloalkenyl groups include, without limitation, cyclopropyl, cyclobutyl, cyclopentyl, cyclohexyl, cycloheptyl, norbomyl, cyclopropenyl, cyclobutenyl, cyclopentenyl, cyclohexenyl, cyclophenyl, anti-bicyclopropane, syn-tricyclopropane, and the like.

As used herein, "heterocycle" or "heterocyclyl" refers to a stable 3- to 18 membered ring (radical) which is saturated, unsaturated, or aromatic, and which consists of carbon atoms and from one to five heteroatoms selected from the group consisting of nitrogen, oxygen and sulfur. For purposes of this invention, the heterocycle may be a monocyclic, bicyclic, or a polycyclic ring system, which may include fused, bridged, or spiro ring systems, including bicyclic rings in which any of the above heterocycles are fused to a benzene ring. The nitrogen, carbon, or sulfur atoms in the heterocycle may be optionally oxidized; the nitrogen atom may be optionally quaternized; and the ring may be partially or fully saturated. The heterocycle may be attached via any heteroatom or carbon atom. Heterocycles include heteroaryls as defined below. Examples of such heterocycles include, without limitation, morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like. Further heterocycles and heteroaryls are described in Katritzky et al., eds., Comprehensive Heterocyclic Chemistry: The Structure, Reactions, Synthesis and Use of Heterocyclic Compounds, Vol. 1-8, Pergamon Press, N.Y. (1984), which is hereby incorporated by reference in its entirety.

The term "acyl" refers to groups of from 1 to 8 carbon atoms of a straight, branched, or cyclic configuration, saturated, unsaturated, or aromatic, and combinations thereof, attached to the parent structure through a carbonyl functionality. One or more carbons in the acyl residue may be replaced by nitrogen, oxygen, or sulfur as long as the point of attachment to the parent remains at the carbonyl. Examples include acetyl (Ac), benzoyl, propionyl, isobutyryl, t-butoxycarbonyl, benzyloxycarbonyl, and the like.

The term "amino acid" refers to the fragment of an amino acid that remains following amide bond formation via reaction of the amino acid carboxyl group with an amino group of another molecule. The amino acid can be in D- or L-configuration. Suitable amino acids include α-amino acids, β-amino acids, γ-amino acids, δ-amino acids, and ε-amino acids, and include not only natural amino acids (i.e., those found in biological systems, including the twenty amino acids found in natural proteins), but also naturally-occurring variants of such amino acids, as well as synthetic amino acids and their analogues known to those skilled in the art. Exemplary amino acids include the twenty natural amino acids, 4-hydroxyproline, hydroxyysine, demosine, isodemosine, 3-methylhistidine, norvalin, beta-alanine, gamma-aminobutyric acid, citrulline, homocysteine, homoserine, ornithine, and methionine sulfone.

The term "pyrimidine" refers to a heteroaromatic compound containing a benzene ring with two carbon atoms replaced by two nitrogen atoms (diazine). For instance, the following moiety having the carbon atoms at positions 1 and 3 replaced by nitrogen atoms is considered a pyrimidine

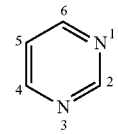

This term, as it is defined herein, also includes its isomeric forms of diazine, such as pyridazine, with the nitrogen atoms in positions 1 and 2; and pyrazine, with the nitrogen atoms in positions 1 and 4. The term "pyrimidine" also generally includes its analogues and derivatives. For instance, the natural nucleobases, cytosine (C), thymine (T), and uracil (D), are pyrimidine derivatives. The term "purine" refers to a heteroaromatic compound containing a pyrimidine ring fused to an imidazole ring. The term "purine" also generally includes its analogues and derivatives. For instance, the natural nucleobases, adenine (A) and guanine (G). Other examples of naturally occurring purine derivatives are hypoxanthine, xanthine, theobromine, caffeine, uric acid, and isoguanine. Exemplary purines and pyrimidines include those disclosed in U.S. Pat. No. 3,687,808; Concise Encyclopedia Of Polymer Science And Engineering, pages 858-859; 30 Kroschwitz, 1. 1., ed. John Wiley & Sons, 1990; and Englisch et al., Angewandte Chemie, International Edition, 1991, 30, 613, each of which is hereby incorporated by reference in its entirety.

The term "nucleobase" includes all natural and synthetic nucleobases as well as universal nucleobases. Typical natural nucleobases include adenine, guanine, cytosine, uracil, and thymine. Synthetic nucleobases typically include inosine, xanthine, hypoxanthine, nubularine, isoguanisine, or tubercidine. As used herein, a universal nucleobase is any modified, unmodified, naturally occurring or non-naturally occurring nucleobase that can substitute for more than one of the natural nucleobases. Universal bases typically contain an aromatic ring moiety that may, or may not contain nitrogen atoms and generally use aromatic ring stacking to stabilize an oligonucleotide duplex. Some universal bases can be covalently attached to the C-1' carbon of a pentose sugar to make a universal nucleotide. Some universal bases do not hydrogen bond specifically with another nucleobase.

Some universal bases base pair with all of the naturally occurring nucleobases. Some universal bases may interact with adjacent nucleotide bases on the same nucleic acid strand by hydrophobic stacking. Exemplary universal nucleobases include, but are not limited to, 2,4-difluorotoluene, nitropyrrolyl, nitroindolyl, 8-aza-7-deazaadenine, 4-fluoro6-methylbenzimidazle, 4-methylbenzimidazle, 3-methyl isocarbostyrilyl, 5-methyl isocarbostyrilyl, 3-methyl-7-propynyl isocarbostyrilyl, 7-azaindolyl, 6-methyl-7-azaindolyl, imidizopyridinyl, 9-methyl-imidizopyridinyl, pyrrolopyrizinyl, isocarbostyrilyl, 7-propynyl isocarbostyrilyl, propynyl-7-azaindolyl, 2,4,5-trimethylphenyl, 4-methylinolyl, 4,6dimethylindolyl, phenyl, napthalenyl, anthracenyl, phenanthracenyl, pyrenyl, stilbenzyl, tetracenyl, pentacenyl, and structural derivatives thereof.

Suitable nucleobases include, but are not limited to, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2aminopropyl) uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and 0-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, methoxycarbonylmethyluracil, 5-methyl-2-thiouracil, 5-methoxycarbonylmethyl-2thiouracil, 5-methylaminomethyl-2-thiouracil, 3-(3-amino-3-carboxypropyl)uracil, 3-methylcytosine, 5-methylcytosine, N4-acetyl cytosine, 2-thiocytosine, N6-methyladenine, N6-isopentyladenine, 2-methylthio-N-6-isopentenyladenine, N-methylguanines, and O-alkylated bases. Further purines and pyrimidines include those disclosed in U.S. Pat. No. 3,687,808; Concise Encyclopedia Of Polymer Science And Engineering, pages 858-859; Kroschwitz, 1. 1., ed. John Wiley & Sons, 1990; and Englisch et al., Angewandte Chemie, International Edition, 1991, 30, 613, each of which is hereby incorporated by reference in its entirety.

The term "nucleoside" refers to a compound comprising a nucleobase, as defined herein, linked to a pentose at the l'-position. When the nucleobase is a purine derivative or anologue, the pentose is typically attached to the nucleobase at the 9-position of the purine derivative or anologue. When the nucleobase is a pyrimidine derivative or anologue, the pentose is typically attached to the nucleobase at the I-position of the pyrimidine (e.g., Kornberg and Baker, DNA Replication, 2nd Ed., Freeman, San Francisco, 1992, which is hereby incorporated by reference in its entirety). When a nucleoside is present in $R^3$, $R^4$, or $R^5$ herein, the nucleoside may be connected to the neighboring atom(s) through any atom on the nucleobase or pentose.

The term "fatty acid" generally refers to a carboxylic acid with an aliphatic tail (chain). The aliphatic chain can be between about 2 and about 36 carbon atoms in length. Fatty acids can be saturated, unsaturated, or polyunsaturated. The aliphatic chain can be a linear or a branched chain. The term "fatty acid" may be used herein to refer to a "fatty acid derivative" which can include one or more different fatty acid derivatives, or mixtures of fatty acids derivatives. Exemplary fatty acids include unsaturated fatty acids, saturated fatty acids, and diacids; mono-, di-, and tri-glycerides of ascarosides that have a carboxylic acid functionality; hydroxy acids, co hydroxy acids, co-I hydroxy acids, dihydroxy fatty acids (e.g., dihydroxy fatty acids that are omega- or omega-1 hydroxylated, as well as alpha- or beta-hydroxylated fatty acids).

The term "sugar" refers to a compound which is either a carbohydrate per se made up of one or more monosaccharide units having at least 5 carbon atoms (which may be linear, branched, or cyclic) with an oxygen, nitrogen, or sulfur atom bonded to each carbon atom; or a compound having as a part thereof a carbohydrate moiety made up of one or more monosaccharide units each having at least 5 carbon atoms (which may be linear, branched or cyclic), with an oxygen, nitrogen or sulfur atom bonded to each carbon atom. Representative sugars include the mono-, di-, tri-, and oligosaccharides containing from about 4-9 monosaccharide units, and polysaccharides such as starches, glycogen, cellulose, and polysaccharide gums. Exemplary monosaccharides include C, and above (e.g., $C_5$-$C_8$ or $C_5$-$C_6$ sugars); di- and trisaccharides include sugars having two or three monosaccharide units.

The term "monosaccharide" means a sugar molecule having a chain of 3-10 carbon atoms in the form of an aldehyde (aldose) or ketone (ketose). Suitable monosaccharides include both naturally occurring and synthetic monosaccharides. Suitable monosaccharides include trioses, such as glycerose and dihydroxyacetone; textroses such as erythrose and erythrulose; pentoses, such as xylose, arabinose, ribose, xylulose ribulose; methyl pentoses (6-deoxyhexoses), such as rhamnose and fucose; hexoses, such as ascarylose, glucose, mannose, galactose, fructose, and sorbose; and heptoses, such as glucoheptose, galamannoheptose, sedoheptulose, and mannoheptulose. Exemplary monosaccharides embrace radicals of allose, altrose, arabinose, cladinose, erythrose, erythrulose, fructose, Dfucitol, L-fucitol, fucosamine, fucose, fuculose, galactosamine, D-galactosaminitol, N-acetyl-galactosamine, galactose, glucosamine, N-acetyl-glucosamine, glucosaminitol, glucose, glucose-6-phosphate, gulose glyceraldehyde, L-glycero-D-mannos-heptose, glycerol, glycerone, gulose, idose, lyxose, mannosamine, mannose, mannose-6-phosphate, psicose, quinovose, quinovosamine, rhamnitol, rhamnosamine, rhamnose, ribose, ribulose, sedoheptulose, sorbose, tagatose, talose, tartaric acid, threose, xylose, and xylulose. The monosaccharide can be in D- or L-configuration. A typical monosaccharide used herein is hexose.

The monosaccharide may further be a deoxy sugar (alcoholic hydroxy group replaced by hydrogen), amino sugar (alcoholic hydroxy group replaced by amino group), a thio sugar (alcoholic hydroxy group replaced by thiol, or CvO replaced by C=S, or a ring oxygen of cyclic form replaced by sulfur), a seleno sugar, a telluro sugar, an aza sugar (ring carbon replaced by nitrogen), an imino sugar (ring oxygen replaced by nitrogen), a phosphano sugar (ring oxygen replaced with phosphorus), a phospha sugar (ring carbon replaced with phosphorus), a C-substituted monosaccharide (hydrogen at a non-terminal carbon atom replaced with carbon), an unsaturated monosaccharide, an alditol (carbonyl group replaced with CHOH group), aldonic acid (aldehydic group replaced by carboxy group), a ketoaldonic acid, a uronic acid, an aldaric acid, and so forth. Amino sugars include amino monosaccharides, such as galactosamine, glucosamine, mannosamine, fucosamine, quinovasamine, neuraminic acid, muramic acid, lactosediamine, acosamine, bacillosamine, daunosamine, desosamine, forosamine, garosamine, kanosamine, kansosamine, mycaminose, mycosamine, perosamine, pneumosamine, purpurosamine, rhodosamine. It is understood that the monosaccharide and the like can be further substituted.

The terms "disaccharide", "trisaccharide", and "polysaccharide" embrace radicals of abequose, acrabose, amicetose, amylopectin, amylose, apiose, arcanose, ascarylose, ascorbic acid, boivinose, cellobiose, cellotriose, cellulose, chacotriose, chalcose, chitin, colitose, cyclodextrin, cymarose, dextrin, 2-deoxyribose, 2-deoxyglucose, diginose, digitalose, digitoxose, evalose, evemitrose, fructoologosachharide, galto-oligosaccharide, gentianose, gentiobiose, glucan, glucogen, glycogen, hamamelose, heparin, inulin, isolevoglucosenone, isomaltose, isomaltotriose, isopanose, kojibiose, lactose, lactosamine, lactosediamine, laminarabiose, levoglucosan, levoglucosenone, ~-maltose, maltriose, mannan-oligosaccharide, manninotriose, melezitose, melibiose, muramic acid, mycarose, 20 mycinose, neuraminic acid, nigerose, nojirimycin, moviose, oleandrose, panose, paratose, planteose, primeverose, raffinose, rhodinose, rutinose, sarmentose, sedoheptulose, solatriose, sophorose, stachyose, streptose, sucrose, a, a-trehalose, trehalosamine, turanose, tyvelose, xylobiose, umbelliferose, and the like. Further, it is understood that the "disaccharide", "trisaccharide", and "polysaccharide" and the like can be further substituted. Disaccharide also includes amino sugars and their derivatives, particularly, a mycaminose derivatized at the C-4' position or a 4 deoxy-3-amino-glucose derivatized at the C-6' position.

The term "polycyclic" or "multi-cyclic" used herein indicates a molecular structure having two or more rings, including, but not limited to, fused, bridged, or spiro rings.

The above "alkyl", "alkenyl", "cycloalkyl", and "cycloalkenyl" radicals, as well as the ring system of the above aryl, heterocyclyl, or heteroaryl groups, may be optionally substituted.

The term "substituted" or "optionally substituted" is used to indicate that a group may have a substituent at each substitutable atom of the group (including more than one substituent on a single atom), provided that the designated atom's normal valency is not exceeded and the identity of each substituent is independent of the others. In accordance with the present invention, up to three H atoms in each residue can be replaced with alkyl, halogen, haloalkyl, alkyenyl, haloalkenyl, cycloalkyl, cycloalkenyl, hydroxy, alkoxy, acyl, carboxy, carbalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, aryl, heteroaryl, heterocyclyl, aryloxy, heteroaryloxy, a purine or pyridimine or an analogue or derative thereof (as defined in "nucleobase"), or a sugar such as a monosaccharide having 5 or 6 carbon atoms (as defined in "monosaccharide"). "Unsubstituted" atoms bear all of the hydrogen atoms dictated by their valency. When a substituent is keto (i.e., =0), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious agent.

In the characterization of some of the substituents, certain substituents may combine to form rings. Unless stated otherwise, it is intended that such rings may exhibit various degrees of unsaturation (from fully saturated to fully unsaturated), may include heteroatoms, and may be substituted with other substituent groups as described above. The compounds described herein may contain one or more asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration; thus a carbon-carbon double bond depicted arbitrarily herein as trans may be Z, E, or a mixture of the two in any proportion.

The term "compounds of the invention," and equivalent expressions, are meant to embrace the prodrugs, the pharmaceutically acceptable salts, the oxides, the solvates, e.g. hydrates, and inclusion complexes of that compound, where the context so permits, as well as any stereoisomeric form, or a mixture of any such forms of that compound in any ratio, unless otherwise specified. Inclusion complexes are described in Remington, The Science and Practice of Pharmacy, 19th Ed. 1:176-177 (1995), which is hereby incorporated by reference in its entirety. The most commonly employed inclusion complexes are those with cyclodextrins, and all cyclodextrin complexes, natural and synthetic, are specifically encompassed within the claims. Thus, in accordance with some embodiments of the invention, a compound as described herein, including in the contexts of biologically compatible compositions, methods of treatment, and compounds per se, is provided as the salt form. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The "quaternization" of any basic nitrogen-containing groups of the compounds disclosed herein is also contemplated. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides 25 including benzyl and phenethyl bromides. Water or oil-soluble or dispersible products may be obtained by such quaternization.

As used herein, the term "ascaroside" may refer to a compound of Formula I:

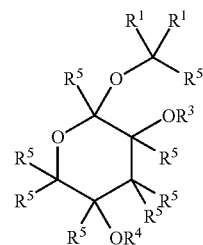

(Formula I)

or a pharmaceutical equivalent, derivative, analog, and/or salt thereof. As readily apparent to one of skill in the art, the compound may be further defined by various R groups.

Particular examples of ascarosides for use in the methods of the invention, include but are not limited to:

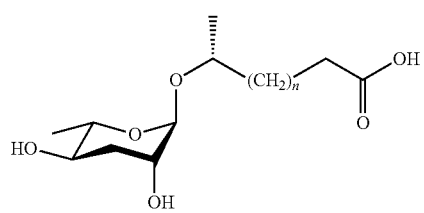

n = 6, ascr#16
n = 7, ascr#18
n = 8, ascr#20
n = 9, ascr#22
n = 10, ascr#24
n = 11, ascr#26

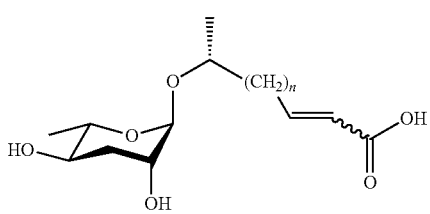

n = 5, ascr#15
n = 6, ascr#17
n = 7, ascr#19
n = 8, ascr#21
n = 9, ascr#23
n = 10, ascr#25

Figure 1:
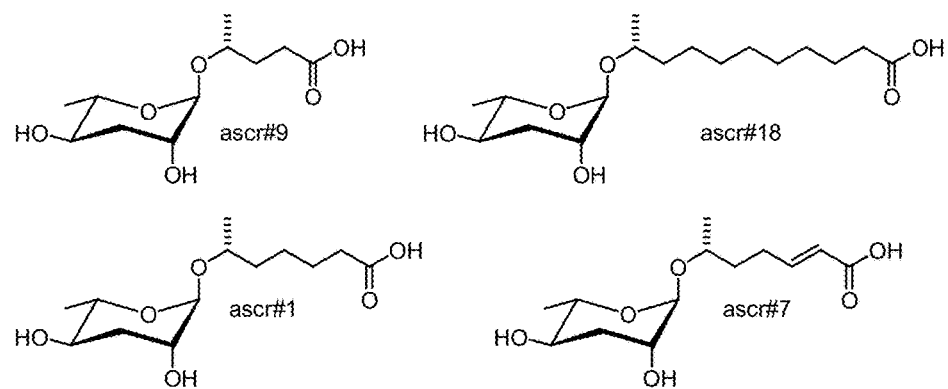
FIG. 1. NAs identified in entomopathogenic nematodes (e.g. ascr#9), plant-parasitic nematodes of the genus *Meloidogyne* (ascr#18), and the animal parasites *N. brasiliensis* and *A. ceylanicum* (ascr#1 and ascr#7).
Figure 7:
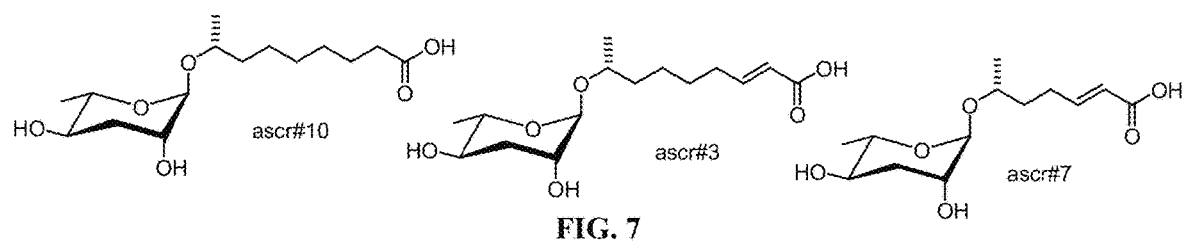
FIG. 7. Structures of ascr#10, ascr#3, and ascr#7. Nomenclature for the structures may be found at www.smid-db.org.
Figure 9:
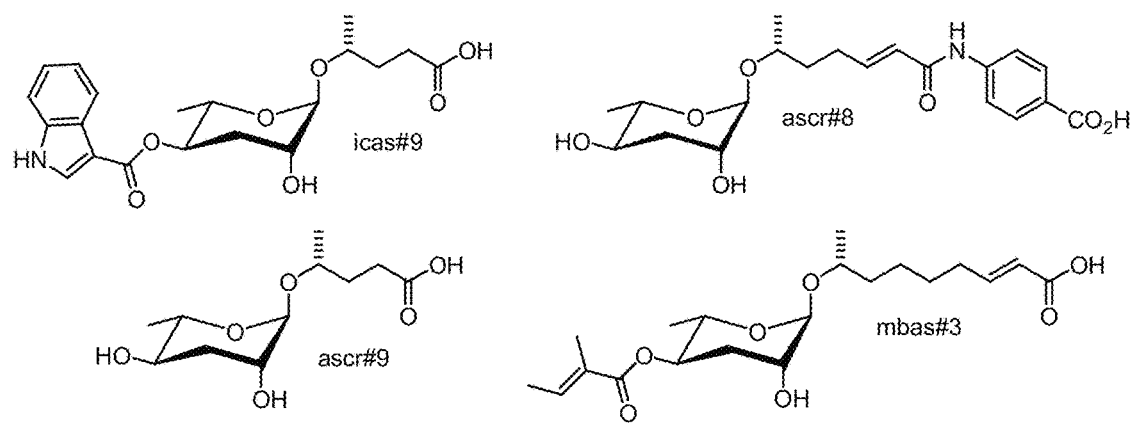
FIG. 9. Structures of ascr#9 and NA derivatives icas#9, mbas#3, and ascr#8.

Also contemplated for use in the invention are the compounds provided below (see also FIGS. 1, 7, and 9), as well as compounds that are structurally identical to the compounds provided below except for the number of carbon atoms in the fatty acid-like side chain (e.g., from between 3 and 24 carbons). Compounds with fatty acid-like side chains containing between 3 and 24 carbon atoms are contemplated for use in the invention.

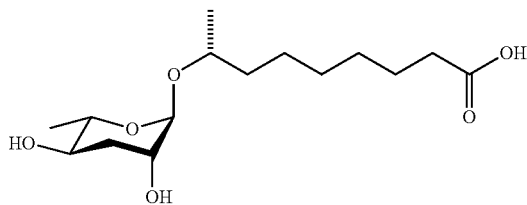

ascr#10

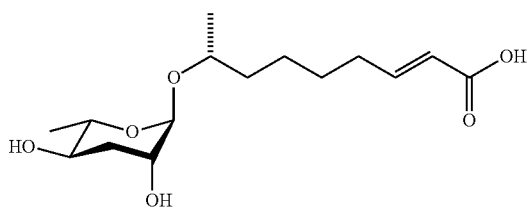

ascr#3

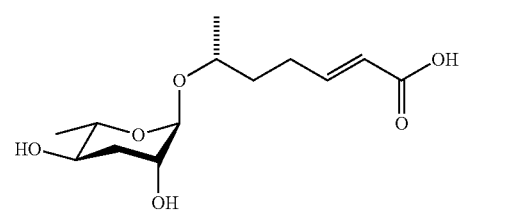

ascr#7 ascr#1

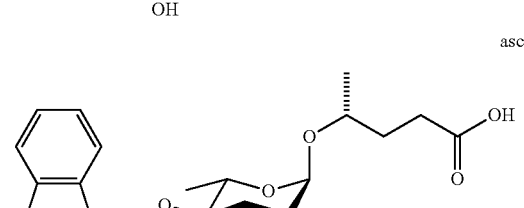

ascr#9

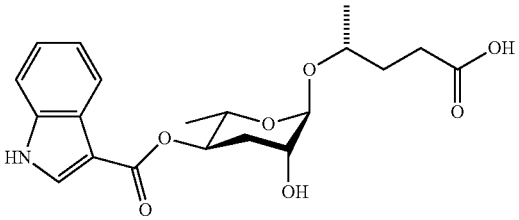

ascr#8

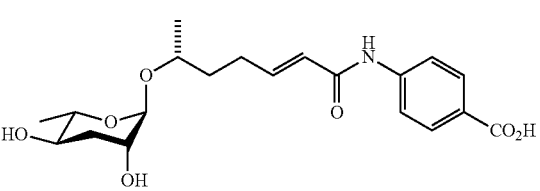

oscr#10

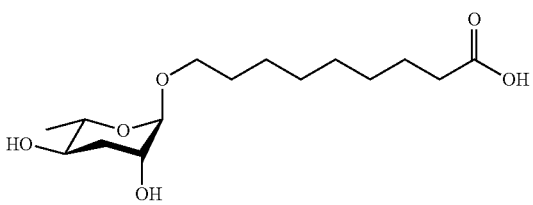

ascr#9
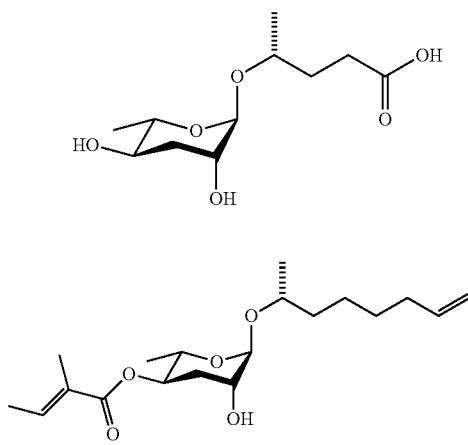
mbas#3 ascr#2
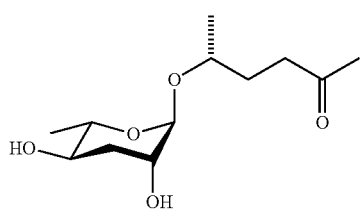

ascr#4
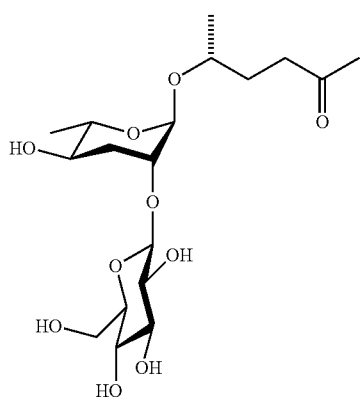

bhas#18
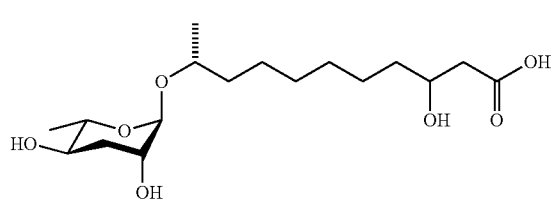

ascr#5
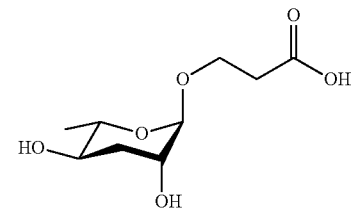

hbas#3
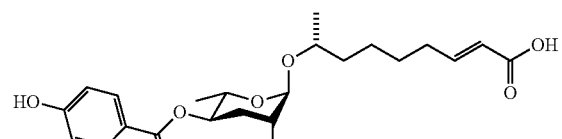

easc#18
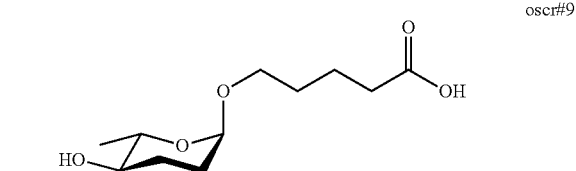

oscr#9
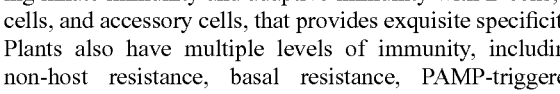

Discriminating non-self from self is a critical aspect of survival that is universal to essentially all living organisms from bacteria, which utilize a restriction-modification system to destroy invading foreign DNA, to vertebrates, which contain a sophisticated, multi-level immune system, including innate immunity and adaptive immunity with B cells, T cells, and accessory cells, that provides exquisite specificity. Plants also have multiple levels of immunity, including non-host resistance, basal resistance, PAMP-triggered immunity (PTI), resistance (R) gene-mediated resistance (also called effector-triggered immunity; ETI), and systemic acquired resistance (SAR). Recognition of foreign compounds by PRRs or R proteins results in significant (often dramatic) alterations in hormonal signaling networks leading to molecular and cellular changes, including callose deposition, reactive oxygen species production, $Ca^{2+'}$ activation of a subset of MAP kinases, and transcriptional reprogramming (Knepper and Day (2010) The *Arabidopsis* book/Amer Soc Plant Biologists 8:e012). These and other changes characterize the immune or defense response in plants.

In accordance with the instant inventions, methods of synthesizing ascr#18 are also provided. In a particular embodiment, the method comprises hydrogenating ascr#17 (e.g., by reacting ascr#17 in solution with Pd/C). The method may further comprise chemically synthesizing ascr#17. Ascr#17 may be synthesized by 1) reacting 7-bromoheptene with (R)-propylene oxide to yield (9R)-hydroxydec-1-ene; 2) reacting 2,4-di-O-benzoyl-ascarylose-1-(2,2,2-trichloroacetimide) with (9R)-hydroxydec-1-ene to yield (9R)-(3'R,5'R-dibenzoyloxy-6'S-methyl-(2H)-tetrahydropyran-2-yloxy)-dec-1-ene; 3) reacting (9R)-(3'R,5'R-dibenzoyloxy-6'S-methyl-(2H)-tetrahydropyran-2-yloxy)-dec-1-ene with an alkyl propenoate, particularly ethyl propenoate, to yield alkyl/ethyl (10R)-(3'R,5'R-dibenzoyloxy-6'S-methyl-(2H)-tetrahydropyran-2-yloxy)-undec-2-enoate; and 4) reacting alkyl/ethyl (10R)-(3'R,5'R-dibenzoyloxy-6'S-methyl-(2H)-tetrahydropyran-2-yloxy)-undec-2-enoate with a hydroxide (e.g., LiOH) to yield ascr#17. The instant invention also encompasses methods comprising only step 4), only steps 3) and 4), or only steps 2), 3), and 4) (i.e., the starting material for the step is already obtained).

The following description sets forth the general procedures involved in practicing the present invention. To the extent that specific materials are mentioned, it is merely for purposes of illustration and is not intended to limit the invention. Unless otherwise specified, general biochemical and molecular biological procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1997) (hereinafter "Ausubel et al.") are used.

The following examples are provided to illustrate certain embodiments of the invention. They are not intended to limit the invention in any way. Certain of the research reported herein was sponsored and financially supported by BASF SE.

Example I

Nematode-Derived Small Molecules can be Used as Defense-Inducing Agents to Increase Crop Plant Resistance to Pathogens Plants recognize foreign/non-self molecules through pattern-recognition receptors (Boller and Felix (2009) Annu Rev Plant Biol., 60:379-406; Knepper and Day (2010) The *Arabidopsis* book/Amer Soc Plant Biologists 8:e012). Several pathogen-associated molecular pattern-containing molecules (PAMPs—also termed MAMPs for microbe-associated molecular patterns) have been identified and shown to induce and/or prime immune responses upon recognition by their cognate receptors. A classic example is the perception of bacterial flagellin by *Arabidopsis* FLS2. The results indicate that plants recognize nematode ascarosides (NAs) as PAMPs. Thus the present invention provided the means for induction of defense responses using potent, naturally occurring small molecules which will dramatically improve agriculture by facilitating manipulation of disease resistance in crop plants.

Animals and Fungi Respond to NAs

Two recent studies have demonstrated that both animals and fungi perceive nanomolar concentrations of NAs. Nematophagous fungi, which are natural predators of soil-dwelling nematodes, use specialized trapping devices to catch and consume nematodes (Barron, 1977). Previous studies demonstrated that most fungal species do not produce traps constitutively, but rather initiate trap formation in response to their prey (Pramer and Stoll (1959) Science 129:966-967). Co-PD Schroeder, in collaboration with the Sternberg lab, showed that nanomolar concentrations of specific NAs trigger trap formation in nematophagous fungi and that NA-induced morphogenesis is conserved in several closely related species of nematophagous fungi (Hsueh et al. (2013) Curr Biol., 23:83-6). Specific NAs also have been shown to modulate immune responses in mammals. In collaboration with the Sternberg and Nakayama (Chiba Univ., Japan) groups, the Schroeder lab tested four NAs widely produced by animal-parasitic nematodes and found that NAs ascr#1 and ascr#7 strongly suppressed the development of asthma in a mouse model system.

NAs Modulate Plant Defense Signaling Pathways

Nematodes are ubiquitous in soil. Therefore, they are in contact with the roots of virtually all plants. Following plant root colonization, some nematode species cause serious diseases. Annual crop losses worldwide caused by nematodes are estimated to be $100 B (Blumenthal and Davis (2004) Nat Genet., 36:1246-1247). Other species of nematodes do not cause disease and may even be beneficial. Recent studies revealed that most, if not all, nematode species produce a class of small-molecule signals called ascarosides that elicit specific responses in mammals and fungi.

Previous studies have suggested that plants perceive the presence of nematodes and respond by enhancing their defenses. For example, using a tomato split-root assay, prior inoculation with host-incompatible (avirulent) *Meloidogyne incognita* reduced susceptibility to host-compatible (virulent) *M. hapla* (Ogallo and McClure (1995) J Nematol., 27:441-447). The antagonistic effect of entomopathogenic nematodes on plant-parasitic nematodes (Molina et al. (2007) J Nematol., 39:338-342) also may be due to induction of plant defenses, such as PR-1 gene expression and catalase and peroxidase activity, not only in the roots, but also in the leaves (Jagdale et al. (2009) J Nematology 41:341-341; Jagdale et al. (2009b) Biol Control 51:102-109). However, the nature of the nematode-derived signal(s), its perception by the host plant, and the subsequent signaling pathway(s) leading to defense responses has remained a mystery.

Given NAs' effects on animals and fungi, the present inventors initiated an effort to assess NAs' effects, if any, on plant immunity. For this study, the NA ascr#18, which is particularly prevalent in several species of the plant parasitic nematode genus *Meloidogyne*, was tested in two plants, tobacco and *Arabidopsis*.

Tobacco.

Figure 2:
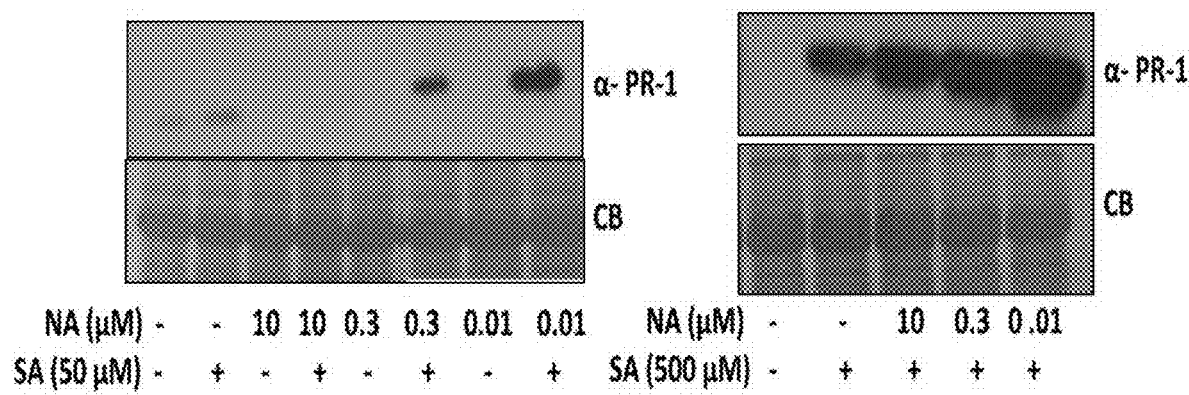
FIG. 2. Nematode ascaroside ascr#18 enhanced SA induction of PR-1 protein production in tobacco W38 plants. Four-weeks old tobacco plants were syringe-infiltrated with buffer, SA, or a mixture of SA (50 µM or 500 µM) and decreasing concentration of ascr#18 (10, 0.3, and 0.01 µM). PR-1 was assayed 48 hours after treatment by immunoblot using anti-PR-1 antibody. Coomassie Blue (CB) stained loading control indicated that all the samples were equally loaded.

To determine whether ascr#18 affects levels of the prototypic SA-responsive PR-1 gene/protein, tobacco plants were treated with varying concentrations of ascr#18 in the presence or absence of SA (FIG. 2). Application of 0.01, 0.3, or 10 µM ascr#18 alone to leaves did not induce PR-1 protein accumulation. However, in the presence of either high (500 µM) or suboptimal (50 µM) levels of SA, ascr#18 at 0.01 or 0.3 µM enhanced PR-1 accumulation to greater levels than those detected in plants treated only with SA. Interestingly, enhancement was strongest at the lowest concentration of ascr#18, indicating that plants are able to detect NAs at very low concentrations and suggesting that concentrations even lower than 10 nM may be active. By contrast, high levels of ascr#18 (10 µM), appeared to inhibit the ability of 50 µM SA to induce low-level PR-1 accumulation. Biphasic "contradictory" responses to NAs have previously been observed in several studies of nematode chemical communication (Pungaliya et al. (2009) Proc Natl Acad Sci., 106:7708-7713; Srinivasan et al. (2008) Nature 454:1115-1118; Srinivasan et al. (2012) PLoS Biol 10:e1001237). The higher induction of PR-1 expression/protein accumulation in SA and ascr#18 co-treated plants, as compared with SA-treated plants, could be due to a synergistic effect between these compounds or an NA-induced priming effect.

Application of ascr#18 to roots also was found to enhance SA-mediated induction of PR-1 expression/protein accumulation in tobacco leaves (FIG. 3). This result argues that ascr#18 acts systemically. In contrast to the SA-dependent effect of ascr#18 on PR-1 expression, ascr#18 alone was sufficient to enhance resistance to virulent *Pseudomonas syringae* pv. *tabaci* (P.t.) (FIG. 4). Leaves or roots treated with NA exhibited similarly reduced levels of virulent P.t. growth as leaves treated with 250 µM SA, and no greater reduction was observed when both compounds were provided simultaneously.

*Arabidopsis* and Other Plants.

Analyses of the effects of ascr#18 on *Arabidopsis* indicate that this species also perceives NA, although its responses differ from those of tobacco. Ascr#18 treatment of test leaves or roots induces PR-1 expression even in the absence of SA (FIG. 5). In addition, ascr#18 treatment induces expression of the prototypic JA-responsive PDF1.2 gene. Interestingly, ascr#18 suppresses SA-mediated PR-1 expression, and this effect was observed when NA and SA were co-applied to the test leaves or when ascr#18 was applied through the roots. As in tobacco, pretreatment of *Arabidopsis* leaves with ascr#18 enhanced resistance to a virulent bacterial pathogen, *P. syringae*. pv tomato DC3000 (Pst) (FIG. 6). Co-treatment with a suboptimal level of SA (50 µM) further enhanced resistance.

Figure 10A:
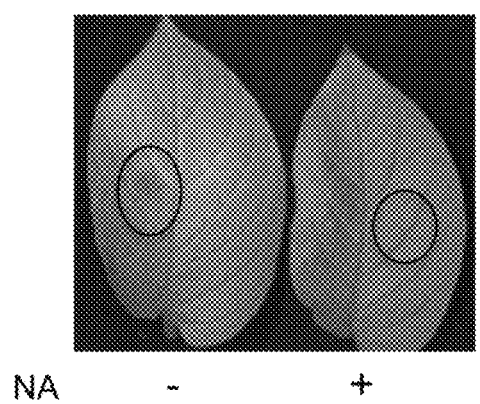
FIGS. 10A and 10B. NA (ascr#18) enhanced resistance in potato cv. Desiree to virulent US22 strain of *Phytophthera infestans*. Potato plants were treated via root immersion with water (control) or with NA (0.01 µM) 48 hours before inoculation with *P. infestans* using a detached leaflet assay.
Figure 10B:
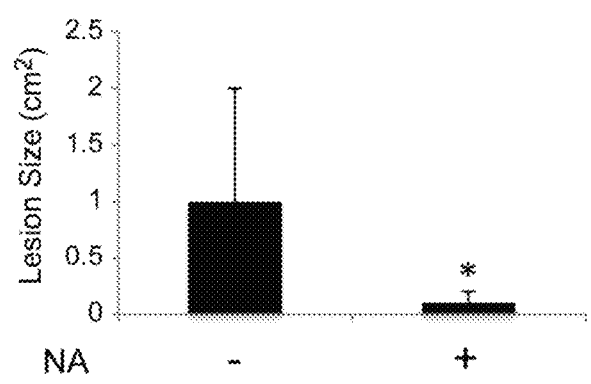
Figure 11A:
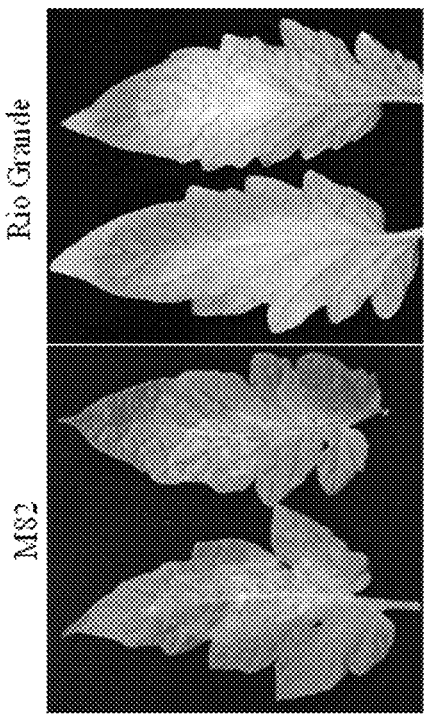
FIGS. 11A, 11B, and 11C. NA (ascr#18) enhanced resistance in tomato cv. M82 and Rio Grande to virulent US22 strain of *P. infestans*. Tomato plants were treated via root immersion with water (−) or with 0.01 µM NA (+) 48 hours before inoculation with *P. infestans* using a detached leaflet assay.
Figure 11B:
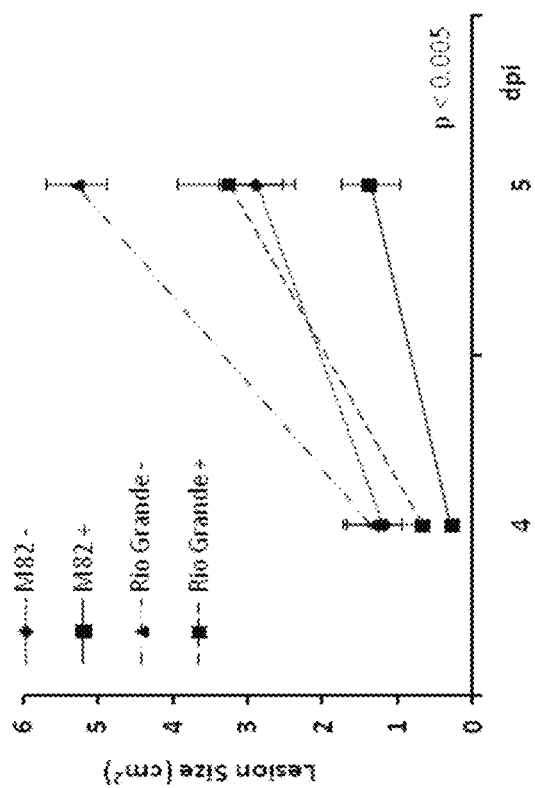
Figure 11C:
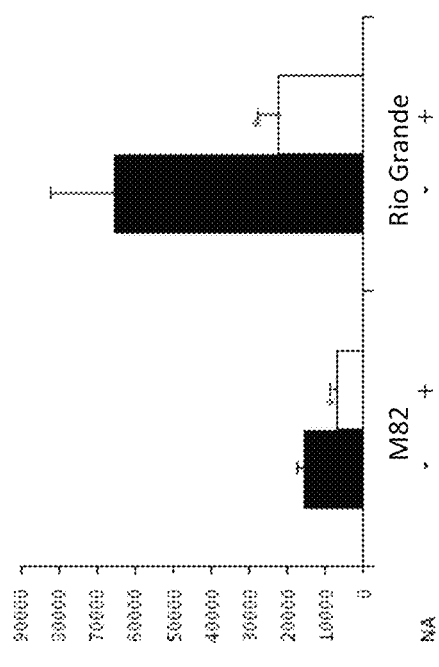

Further studies with potato and tomato, two important crop plants, demonstrated the pretreatment of their roots with ascr#18 enhanced resistance to the most devastating plant pathogen, *Phytophthora infestans*, causal agent of late blight and the Great Irish Potato Famine of the 1840s (see FIGS. 10 and 11).

The observation that NAs modulate plant immune responses provides both important insights into plant immunity and opportunities to enhance plant protection against nematodes and other disease agents. The use of NAs as plant protectants has great potential given that they i) are active at very low concentrations (nM range), ii) can be readily synthesized in large quantities, iii) are bio-degradable, and iv) will face lower regulatory hurdles for approval since they are natural products. Therefore, the present invention will significantly enhance food security worldwide and also reduce the use of chemical pesticides that may be harmful to humans and/or the environment. This novel approach of using small signaling molecules from potential pathogens to prime or activate the plants' immune system will also improve the economic and environmental sustainability of agriculture.

Example II

NA Variants Most Active in Modulating Plant Defense Responses

Bioassays using NAs and nematodes, fungi, or mammals have demonstrated that even minor variations in NA structure strongly affect biological activity (Hsueh et al. (2013) Curr Biol., 23:83-6; Ludewig and Schroeder (2013) WormBook, 1-22). For example, the seemingly minor difference in the structures of ascr#10 and its unsaturated derivative ascr#3 is associated with profound differences in biological responses of *C. elegans*: whereas the hermaphrodite-produced ascr#3 repels hermaphrodites, male-produced ascr#10 strongly attracts hermaphrodites (Izrayelit et al. (2012) ACS Chem Biol., 7:1321-1325). Similarly, the unsaturated ascaroside ascr#7 strongly suppresses ovalbumin-specific T-helper cell responses in mice, whereas ascr#3, which is distinguished from ascr#7 by a two-carbon longer side chain, has no significant effect. Based on these findings, it is likely that ascr#18 is not the only NA affecting plant defense responses and that NAs with more potent or different activity profiles exist. Therefore, a bioactivity screen of a chemically diverse set of NAs may be performed in several plant species that have been shown to respond to ascr#18, such as tobacco, potato, tomato, and *Arabidopsis*.

Selection of NAs for Bioactivity Screening

Initial studies were focused on NAs prevalent among plant-parasitic nematodes, as well as NAs very broadly produced by species from different branches of the nematode phylum (Choe et al. (2012) Proc Natl Acad Sci., 109:20949-20954; Choe et al. (2012) Curr Biol., 22: 772-780; Srinivasan et al. (2012) PLoS Biol 10:e1001237; Izrayelit et al. (2012) ACS Chem Biol., 8:314-9). Representatives of chemically different families of the 200 identified NAs identified to date can be selected and tested for the ability to induce or "prime" an immune or defense resistance response in plants as described herein.

Figure 8:
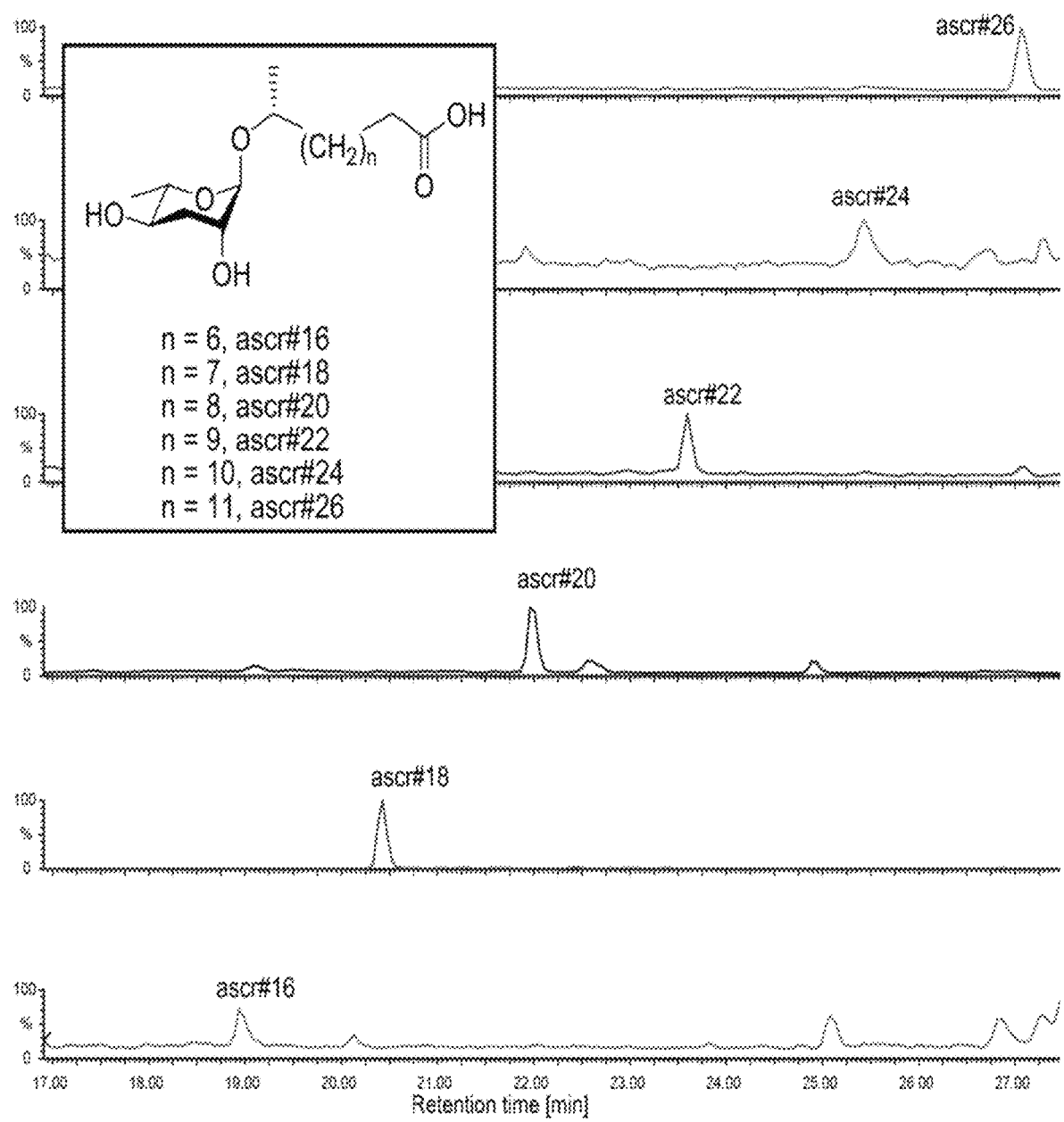
FIG. 8. NAs identified from *Meloidogyne hapla* infective juveniles. Nematodes were incubated in buffer for 24 hours and the supernatant collected for analysis by HPLC-MS. Shown are ion chromatograms for ions corresponding to [M-H]⁻ of NAs ascr#16 through ascr#26. In addition, *M. hapla* produces small amounts of the shorter-chained ascr#10.

The most abundant NAs produced by several species of plant-parasitic nematodes belonging to the genus *Meloidogyne* have been identified. HPLC-MS analysis of metabolite extracts obtained from infective juveniles of *M. incognita, M. javanica*, and two different *M. hapla* strains consistently revealed abundant production of ascr#16, ascr#18, ascr#20, ascr#22, and ascr#26 in all three species (FIG. 8). In addition to assessing the biological activity of these 5 NAs, ascr#10 and its unsaturated derivative ascr#3 may be tested as well as the short-chained ascr#9, all of which are very widely produced among parasitic and free-living nematodes (Choe et al. (2012) Curr Biol., 22:772-780). Furthermore, the NA derivative icas#9 may be tested as it is the most widespread representative of indole ascarosides, and mbas#3 and ascr#8, which are representatives of NA families that are produced abundantly in free-living nematodes including *Caenorhabditis* spp. (Pungaliya et al. (2009) Proc Natl Acad Sci., 106:7708-7713 Srinivasan et al. (2012) PLoS Biol 10:e1001237). Depending on the results from the activity screen of these 10 NAs, additional NAs may be selected for testing. For example, if the indole ascaroside icas#9 shows high biological activity, additional indole ascarosides may be tested, including icas#1, icas#3, and icas#10 (Srinivasan et al. (2012) PLoS Biol 10:e1001237). If short-chained ascarosides such as ascr#9 or ascr#3 show promising activity, additional NAs from this group may be tested, which is particularly diverse chemically (von Reuss et al. (2012) J Am Chem Soc., 134:1817-1824). Any of the ascarosides disclosed herein may be assessed for modulation of disease resistance in plants.

Synthesis of NAs for Bioactivity Screening

The chemical synthesis of large varieties of NAs has been worked out in detail and 1-2 g of these compounds can be prepared easily using established methods (Pungaliya et al. (2009) Proc Natl Acad Sci., 106:7708-7713; Srinivasan et al. (2012) PLoS Biol 10:e1001237; von Reuss et al. (2012) J Am Chem Soc., 134:1817-1824; Bose et al. (2012) Angew Chem Int Ed Engl 51:12438-12443). Physiological concentrations of NAs in *M. hapla* cultures have reached up to 100 nM, and many other NAs are found at concentrations up to 10 µM, roughly defining the upper limit of what can be considered a physiological range of concentrations. In soil, NA concentrations are generally much lower. Ascr#18 concentrations in the picomolar and low nanomolar range have been found to induce a response. Notably, activity was most frequently observed in exactly this concentration range in *C. elegans*, nematophagous fungi, and mice. Anticipating the need to provide up to several liters of solution containing NAs at picomolar to low micromolar concentrations for bioassays, a multi-gram sample of the NA parent compound, ascarylose, may be prepared and then further modified to produce the different compounds shown in FIGS. 7-9 using described methods (Pungaliya et al. (2009) Proc Natl Acad Sci., 106:7708-7713; Srinivasan et al. (2012) PLoS Biol 10:e1001237; von Reuss et al. (2012) J Am Chem Soc., 134:1817-1824).

Bioassays Using Tobacco and *Arabidopsis*

Our initial results indicate that ascr#18 induces expression of the SA-regulated PR-1 and JA-responsive PDF1.2 genes in *Arabidopsis* (FIG. 5), and enhances SA-induced PR-1 expression in tobacco (FIGS. 2 and 3). Thus, the biological activity of the various NAs will initially be assessed by monitoring their ability to (i) induce or enhance expression of PR-1 in the absence or presence of 50 µM SA in *Arabidopsis* and tobacco, and (ii) induce expression of PDF1.2 in *Arabidopsis* or a yet to be identified JA-responsive gene in tobacco, in which a PDF1.2 homolog has not been detected. These screens will be performed using 1 µM, 0.01 µM, or 0.0001 µM NA, which will be applied via syringe-infiltration to the leaves. Those NAs with the highest activity will be further tested for their ability to increase resistance to virulent *P. syringae* in both *Arabidopsis* and tobacco.

In certain cases, specific structural features of the tested NAs may be associated with particularly strong plant responses. In such cases, additional NA variants will be rationally designed, synthesized and tested for activity. In addition, if several structurally different NAs show significant activity, mixtures of these NAs may be tested to assess synergy, as has been documented in both fungi and nematodes (Pungaliya et al. (2009) Proc Natl Acad Sci., 106: 7708-7713; Srinivasan et al. (2008) Nature 454:1115-1118).

NAs exhibiting the greatest biological activity also can be used for more detailed dose-response analyses of direct or SA-induced PR-1 expression in *Arabidopsis* and tobacco. Similar analyses will be performed using PDF1.2 or an appropriate JA marker gene to assess NA's effect on JA-mediated signaling in *Arabidopsis* and tobacco, respectively. If one of these NAs is found to be highly active at low nanomolar concentrations, even lower (picomolar and femtomolar) concentrations will be assayed (some NAs have femtomolar activity in *C. elegans*, see e.g. (Srinivasan et al. (2012) PLoS Biol 10:e1001237; von Reuss et al. (2012) J Am Chem Soc., 134:1817-1824; Izrayelit et al. (2012) ACS Chem Biol., 7:1321-1325).

Example III

Characterization of Signaling Pathways Mediating NA Responses

The signaling pathways through which the most active NA compounds mediate their effects will be investigated in both tobacco and *Arabidopsis*. This analysis might be expanded to a second NA, provided it is not only highly active but also elicits a very different effect(s) from the first NA with regard to activation of SA-vs JA-responsive defense genes or enhancement of resistance in *Arabidopsis* vs tobacco. The selected NAs will be applied to leaves as well as roots to assess whether the results are similar to those obtained following leaf application. In addition, characterizing the NA-mediated systemic signal, as well as assessing NA's effect on plant resistance to nematodes, will involve monitoring plant responses following either leaf or root application.

Transcriptional Profiling of NA Responses

For a comprehensive analysis of NA's effect on global gene expression in tobacco and *Arabidopsis*, RNA-seq analyses (Wang et al. (2009) Nature reviews Genetics 10:57-63) will be employed. RNA-seq is now the method of choice for transcriptome analysis due to its i) low background noise, ii) dynamic range for quantifying gene expression, iii) ability to distinguish allelic expression and also paralogous expression, iv) low amount of RNA required, and v) relatively low cost. The design of RNA-seq experiments is based on the premise that different NAs will be more active in one plant species than another, and/or that different NAs will elicit distinct phenotypes in different plant species. This possibility is suggested by the finding that a high concentration of ascr#18 (10 µM) inhibited SA-induced PR-1 expression in tobacco, whereas a 1000-fold lower concentration of this NA (0.01 µM) suppressed SA-induced PR-1 expression in *Arabidopsis*. In addition, while low concentrations of ascr#18 (0.01 or 0.3 µM) induced PR-1 expression in *Arabidopsis*, they failed to induce PR-1 protein accumulation in tobacco unless SA was provided concurrently. These results suggest that *Arabidopsis* is more sensitive to ascr#18, with the biphasic dose-response curve shifted such that concentrations that enhance SA-activated PR-1 expression in tobacco are able to induce defense gene expression on their own in *Arabidopsis*.

In cases where there are one or two NAs (e.g. ascr#18) that are strongly active in both tobacco and *Arabidopsis*, those NAs may be used for transcriptional profiling via RNA-seq in both plant species. If it turns out that one of these NAs is more active in *Arabidopsis* than tobacco, and vice versa, RNA-seq analyses may be performed in both plant species using the corresponding NA with the highest activity in that species. Regardless of whether there are differences in NA activity or the resultant phenotypes in tobacco and *Arabidopsis*, the parallel transcriptional profiling of both plant species will provide significant advantages. If one or both NAs elicit a similar phenotype in *Arabidopsis* and tobacco, it is likely that same pathway(s) mediates this response in both species, which may aid with the identification of one or more regulatory hubs affected by NA. Conversely, if one or both NAs have a very different activity level or elicit divergent phenotypes in *Arabidopsis* and tobacco, combined analysis of the RNA-seq data obtained from both plants will facilitate correlating gene expression changes with the observed differences in response. For all conditions, a minimum of biological triplicates will be used.

For additional transcriptome analyses, NA treatment will be combined with SA or JA treatment. For example, if the most potent NA in *Arabidopsis* at very low concentrations acts synergistically with SA to induce PR-1 expression, transcriptional profiling may be performed after concomitant application of NA and SA at concentrations that result in maximal synergy. To measure NA-modulated changes in pathogen responses, transcriptome analysis also will be performed on NA-treated *Arabidopsis* before and after infection with Pst. *Arabidopsis* offers several advantages over tobacco because of the very extensive transcriptome databases, particularly those obtained after pathogen infection and/or involving mutants affecting plant immunity. However, as emphasized above, the availability of transcriptomic data in two different species will greatly aid in the interpretation of the RNA-seq results thereby elucidating the general and species-specific effects of NA which will be essential to long-term practical (commercial) application in the field.

Detailed Characterization of Pathways Involved in NA-Induced Responses

Results from the transcriptome analyses outlined above should identify the signaling pathways involved in NA responses. Based on preliminary results, both the SA and JA pathways will be implicated. To confirm their involvement, a two-pronged approach will be use including (i) measuring NA-induced changes in basal pathogen resistance, and (ii) monitoring NA's ability to induce the expression of marker genes, such as PR-1 and PDF1.2, in various defense signaling mutants. Initial experiments with *P. syringae* suggest that treatment with ascr#18 enhances basal resistance to this biotrophic pathogen in both tobacco and *Arabidopsis* (FIGS. 4 and 6). These results are consistent with ascr#18's effect on SA-mediated signaling (i.e. induction/enhancement of PR-1 expression), since resistance to biotrophic pathogens is SA dependent. Induction of PDF1.2 by ascr#18 in *Arabidopsis* argues that JA-mediated defense signaling is also affected. Since resistance to necrotrophic pathogens is JA dependent, the effect of NA(s) on basal resistance to necrotrophs, such as *Botrytis cinerea* (or *Alternaria brassicicola*), in *Arabidopsis* will be tested. The ability of NA(s) to enhance resistance to additional pathogens and/or activate other levels of resistance, including R gene-mediated immunity also will be assessed. For the latter analysis, avirulent Pst AvrRPS2 or Pst AvrRPM1 may be used with *Arabidopsis*, and Tobacco Mosaic Virus (TMV) with the Xanthine cultivar of tobacco, which carries the N gene and therefore is TMV resistant.

To further investigate the signaling pathways through which NA(s) exerts its effect, NA-mediated induction of PR-1 and PDF1.2 and enhanced resistance to Pst and *B. cinerea* will be assessed in *Arabidopsis* mutants compromised for SA-mediated defense signaling (e.g. isc1-SA synthesis; npr1-SA response) or JA-mediated defense signaling (e.g. jar1 or jin1-JA response). Ethylene (ET) is another important defense signaling hormone that often acts in concert with JA to activate defense genes, such as PDF1.2, and resistance against necrotrophs (Ronald and Beutler (2010) Science 330:1061-1064). To assess whether NA(s) also utilizes the ET signaling network, NA's ability to induce PDF1.2 expression and resistance to *B. cinerea* will be monitored in ET mutants (e.g. etr1 and ein2-ET response).

Assessment of NAs' Effects on Plant Hormone Levels

To assess whether the most active NA directly (or indirectly) affects the levels of SA or JA, the levels of these hormones will be quantified before and after Pst infection. SA and its glucoside (SAG) will be determined via HPLC (Liu et al. (2010) Mol Plant Microbe Interact 23:82-90), while JA levels will be determined by mass spectroscopy (Creelman and Mullet (1995) Proc Natl Acad Sci 92:4114-4119). Should RNA-seq analysis strongly suggest up or down regulation of genes involved in metabolite production, for example glucosinolate biosynthesis in *Arabidopsis* or alkaloid (nicotin) biosynthesis in tobacco further metabolome studies can be performed.

Characterization of the Systemic Signal in Plant NA Responses

Our results indicate that NAs can act systemically, since ascr#18 treatment of *Arabidopsis* or tobacco roots enhanced defense gene expression and resistance to *P. syringae* in the leaves (FIGS. 3-5). Similarly, treating a subset of *Arabidopsis* leaves with ascr#18 induced PDF1.2 expression in untreated, as well as treated, leaves. These results suggest that a signal, perhaps the NA itself, moves from the treated roots or leaves to systemic, untreated leaves. Radiolabeled NAs, which can be readily produced via base-catalyzed proton-to-tritium exchange in the side chain, can be used to test whether the NA itself is mobile or instead acts through an unidentified mobile signal to elicit systemic defense responses. Radiolabeled NA will be applied to roots; 24 or 48 hours post treatment, roots and leaves from treated and untreated (control) plants will be homogenized/solubilized and analyzed via scintillation counting. If the results suggest that the NA is mobile, further analyses will be required to determine whether the NA itself or a radiolabeled derivative is translocated to the leaves. For this purpose, stable-isotope labeling may be used in combination with comparative HPLC-MS. Doubly-deuterium labeled ($d_2$) NA (produced using the same basic protocol as for tritium labeling) and unlabeled NA will be infused into the plant; 24 or 48 hours post treatment, roots and leaves from NA-treated and NA-$d_2$-treated plants will be harvested, extracted with methanol, and analyzed by HPLC-MS/MS using conditions optimized for the detection of ascarosides (von Reuss et al. (2012) J Am Chem Soc., 134:1817-1824). HPLC-MS-based comparison of the samples derived from NA-treated and NA-$d_2$-treated plants will reveal any NA derivatives as peaks whose mass increases by 2 mass units in the sample derived from NA-$d_2$-treated plants. If such species are detected, they will be further characterized by high-resolution MS and isolated via preparative HPLC for identification by 2D NMR spectroscopy, as described for example by (Pungaliya et al. (2009) Proc Natl Acad Sci., 106:7708-7713).

Effect of NA Application on Pathogen Resistance in Multiple Crop Species

Figure 13A:
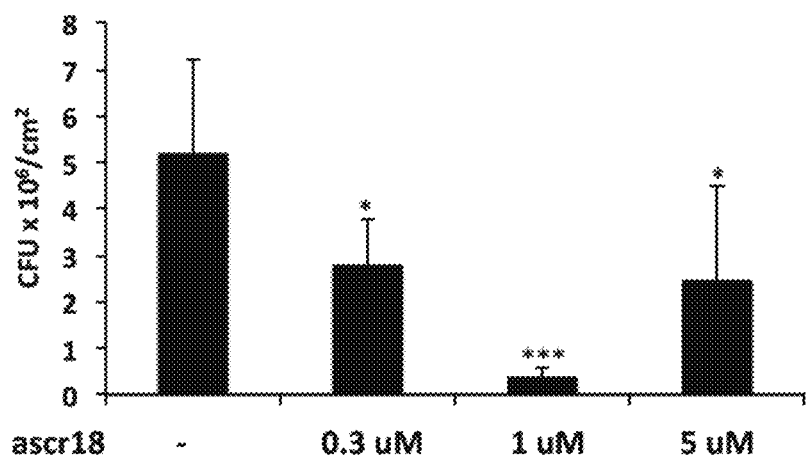
FIGS. 13A, 13B, 13C, 13D, 13E, 13F, 13G, 13H, and 13I.

To test applicability to other crop species, NA-treated tomato, potato, and barley will be analyzed for altered expression of PR-1 and an appropriate JA-responsive marker gene and enhanced resistance to pathogens. NA's ability to enhance resistance in tomato (both basal and R gene-mediated) will be assessed in a Pto-carrying cultivar following inoculation with Pst DC3000+/−AvrPto. Whether NAs enhance resistance in potato and tomato to *Phytophthora infestans*, the causative agent of late blight and the Great Irish Potato Famine of the 1840s, also will be assessed. As part of a large USDA-NIFA funded project on potato and tomato late blight, the Klessig group is currently assessing the role of CRT1 (Kang et al. (2012) Nat Commun 3:1297; Kang et al. (2008) Cell Host Microbe 3:48-57; Kang et al. (2010) Plant Cell 22:918-936) in basal and R gene-mediated resistance to this devastating oomycete pathogen. As a result, all of the cultivars of tomato (+/− the R genes Ph2 and Ph3) and potato (+/−RB) and isolates of *P. infestans* (US11, 22, and 23) that are necessary for investigating NA's effectiveness against this pathogen are available. Early experiments indicate that NA treatment of potato and tomato can dramatically reduce susceptibility to *P. infestans* (FIGS. 10 and 11A-11C). NA's ability to enhance resistance in barley to Blumeria *graminis* pv. *hordei*, the causative agent of powdery mildew, will also be determined. Ascr#18 enhanced resistance to *B. graminis* in barley (FIGS. 15B-15C). Assessment of NA's ability to enhance resistance to nematodes will be extended to tomato, potato, and soybean using root-knot nematode (RKN, *Meloidogyne* spp.) and to sugar beet using beet cyst nematode (BCN, *Heterodera schachtii*). Results indicate that ascr#18 enhanced resistance in *Arabidopsis* to *H. schachtii* (FIG. 13C).

Effects of NAs on Plant Resistance to Nematodes

Previous investigations have shown that prior inoculation with host-incompatible (avirulent) *M. incognita* reduced susceptibility to host-compatible (virulent) *M. hapla* (Ogallo and McClure (1995) J Nematol., 27:441-447). To test whether NAs are responsible for this effect, two or three NAs identified as strong inducers of defense signaling in the initial screen will be assayed in *Arabidopsis*. Seeds will be germinated on vertical plates with either regular medium or medium containing a selected NA (at nM to µM concentrations); 7-day-old seedlings will be inoculated with surface-sterilized juveniles of BCN (*H. schachtii*) or RKN (*M. incognita*) (Wang et al. (2007) Molecular Plant Pathol., 8:423-436). Three-four weeks after nematode inoculation, nematode cyst (for *H. schachtii*) or egg (for *M. incognita*) numbers will be counted and compared with those recovered from control plants to determine if treatment with NAs reduced plant susceptibility to nematode infection.

In addition, nematode infection assays will be conducted on potted plants in the greenhouse. It may also be tested whether NA treatment alters susceptibility to RKN infection in crop plants such as soybean, tomato, and potato, and to cyst nematode infection in potato. Plants will be grown in 2-inch pots and approximately one week after plant emergence, NAs (at 1 nM to 10 µM concentrations) will be applied to the seedling roots through daily watering for one week. These NA-treated and untreated plants will then be inoculated with RKN or cyst nematode eggs (Chronis et al. (2013) Plant J., 74:185-96; Wang et al. (2007) Molecular Plant Pathol., 8:423-436). Four-five weeks after RKN inoculation and 10-12 weeks after cyst nematode inoculation, RKN eggs and cysts will be extracted from plant roots or soil and compared with those recovered from control plants to determine plant susceptibility.

Example IV

Tobacco

Figure 12A:
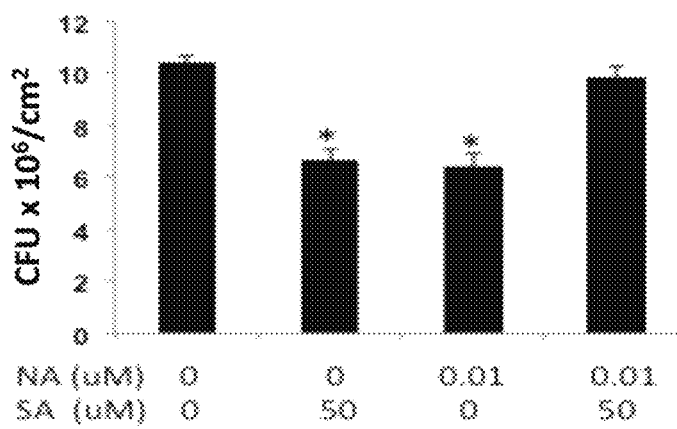
FIGS. 12A, 12B, and 12C.

Ascr#18 enhances resistance in tobacco against the bacterial pathogen *P. syringae* pv *tobaci* when administered alone (FIG. 12A). There was no further enhancement of resistance when salicyclic acid (SA) was added after pretreatment with ascr#18. Tobacco leaves were treated by syringe infiltration with ascr#18 (0.01 µM). SA (50 µM) was syringe infiltrated in leaves 24 hours after treatment with NA. Bacterial inoculations were done 48 hours after nematode ascaroside (NA) treatment and bacterial growth was assayed at 2 dpi.

Figure 12B:
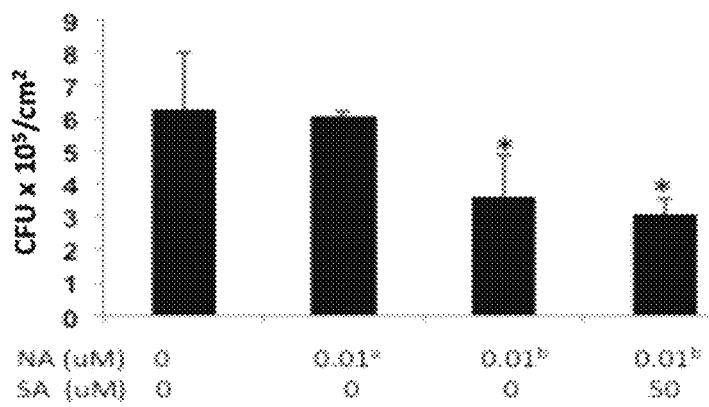

Spray application of ascr#18 enhances resistance against the bacterial pathogen *P. syringae* pv *tabaci* (Pt) when applied 48 hours but not 24 hours before inoculation (FIG. 12B). Spray of a combination of ascr#18 and SA did not further increase resistance. Specifically, tobacco plants were sprayed with ascr#18 (0.01 µM) 24, 48 hours before inoculation with Pt. SA (50 µM) was syringe infiltrated in leaves 48 hours before inoculation at the time of ascr#18 spray. Bacterial growth was assayed at 2 dpi.

Figure 12C:
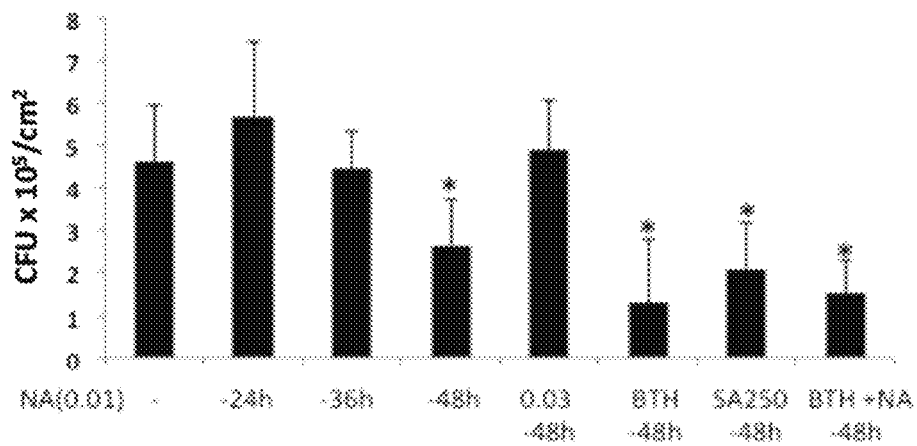

Treatment by root immersion with ascr#18 enhances resistance against the bacterial pathogen *P. syringae* pv *tabaci* (Pt) (FIG. 12C). This protection is as efficient as the protection given by root immersion of BTH (Actigard). Roots of tobacco plants were immersed in a solution of the ascr#18 at 0.01 µM or 0.03 µM, 250 µM SA, 0.075 g/L BTH actigard, or a combination of BTH and ascr#18 (0.01 µM) at various times prior to inoculation with Pt. Bacterial growth was assayed at 2 dpi.

Arabidopsis

To assess whether plants recognize and respond to ascarosides, the effect of ascr#18, the most abundant ascaroside in the analyzed plant-parasitic nematodes, was measured on defense responses of *Arabidopsis* ecotype Col-0 to a bacterial pathogen. Since plants naturally encounter nematodes via their roots, *Arabidopsis* roots were immersed in water containing different concentrations of ascr#18 for 24 hours before leaves were inoculated with the pathogens. Bacterial growth was assayed 3 dpi. Pretreatment with 1 µM ascr#18 provided strong protection against the virulent bacterial pathogen *Pseudomonas syringae* pv tomato DC3000 (Pst), whereas 0.3 µM and 5 µM ascr#18 were less effective (FIG. 13A).

Figure 13B:
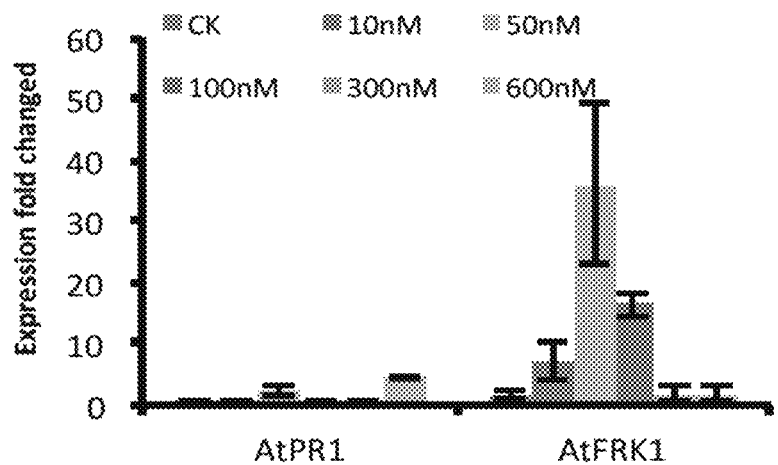
Figure 13C:
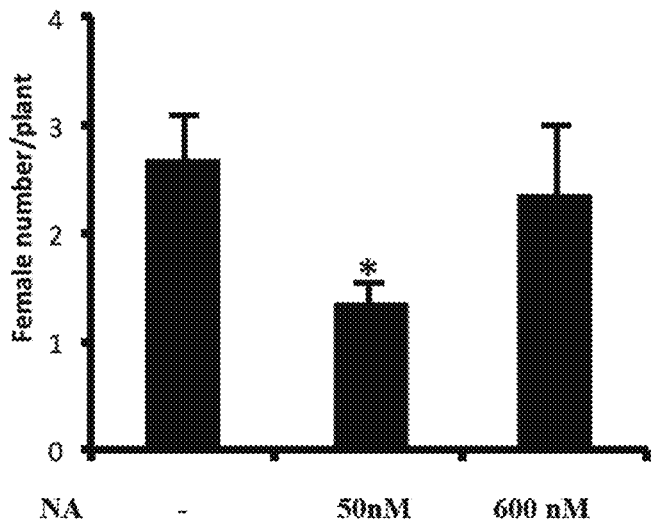

Root treatment with ascr#18 of *Arabidopsis* induces PR-1 and the PTI marker gene FRK1 in roots (FIG. 13B). Roots of *Arabidopsis* seedlings were treated with water (CK) or with various ascr#18 concentrations for 48 hours. Roots were then collected and used to extract RNA for qRT-PCR analysis.

Ascr#18 enhances resistance to cyst nematode *Heterodera schachtii* in *Arabidopsis* (FIG. 13C). *Arabidopsis* plants growing in media without ascr#18 or in media containing 50 nM or 600 nM of ascr#18 were inoculated with *H. schachtii* J2s and nematode females were counted at 19 dpi.

Figure 13D:
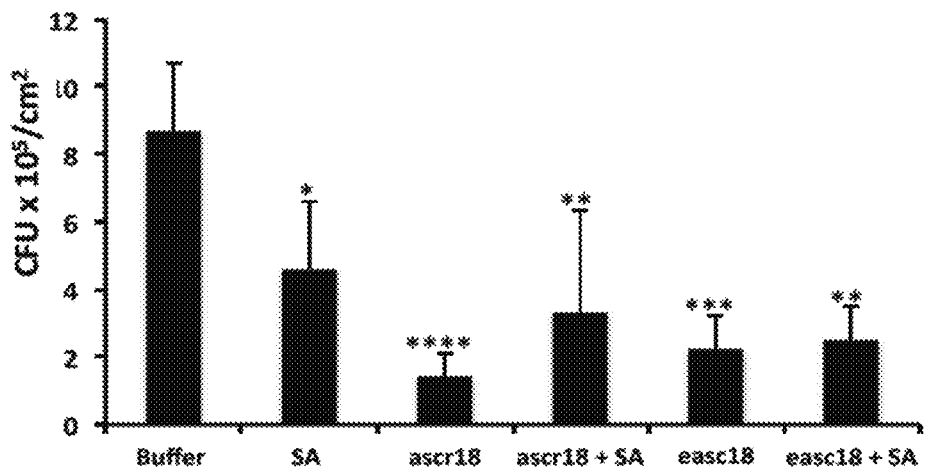
Figure 13E:
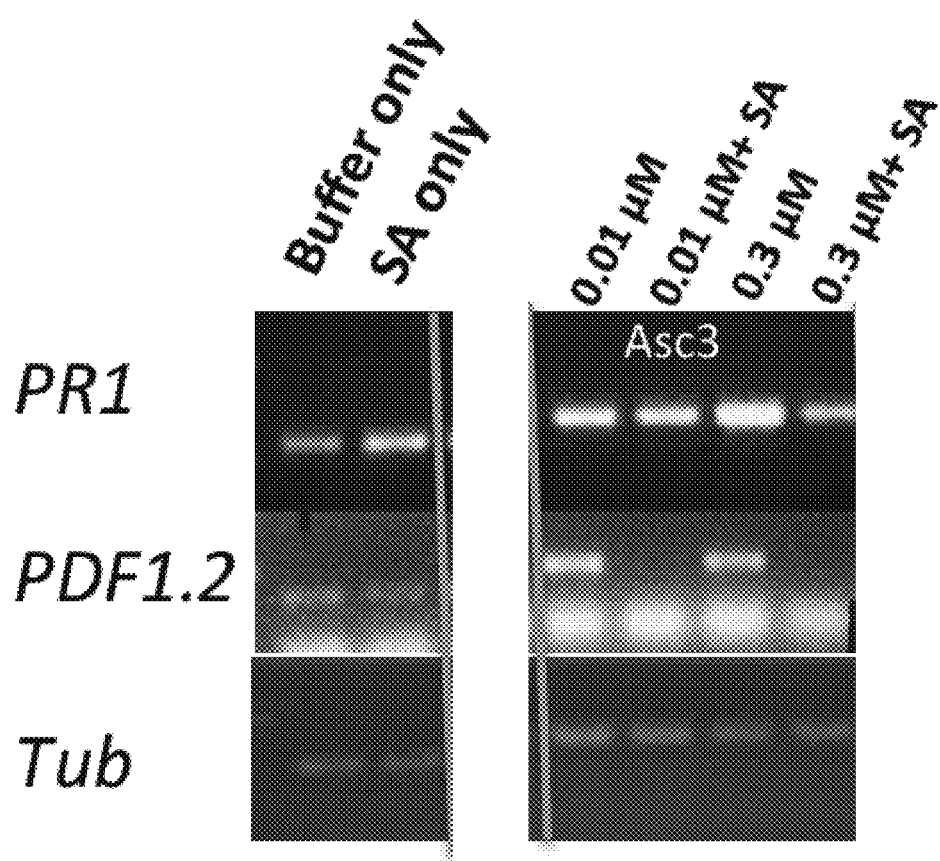
Figure 13F:
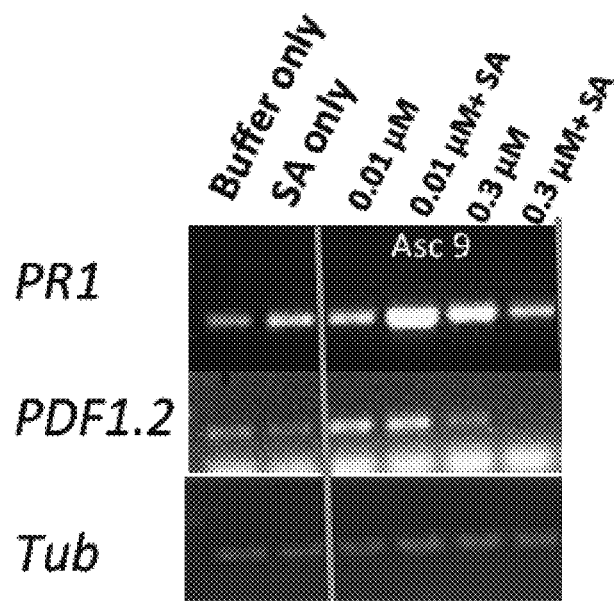

Easc#18 enhances resistance against virulent *Pseudomonas syringae* pv. tomato (Pst) DC3000 (FIG. 13D). *Arabidopsis* ecotype Col-0 leaves were treated by syringe infiltration with ascr#18 (0.3 µM), easc#18 (0.3 µM) and/or SA (50 µM) 24 hours prior to inoculation with Pst. Bacterial growth was assayed 3 dpi.

Ascr#3, ascr#9, oscr#9, or ascr#10 alone induces PR-1 expression in *Arabidopsis* (FIGS. 13E, 13F, 13H, and 13I). Ascr#3, ascr#9, oscr#9, or ascr#10 applied at low concentrations in combination with SA enhances PR-1 expression induced by SA. However, application of higher concentration of ascr#3 or ascr#9 reduces the SA-induced PR-1 expression (similar results were obtained in tobacco with ascr#3, ascr#9, and ascr#10, although low concentrations did not significantly increase PR-1 expression tobacco cv. W38). Ascr#3, ascr#9, or ascr#10 alone also induces PDF1.2 expression. Briefly, leaves of four-weeks old plants were syringe infiltrated with buffer, SA (50 µM), ascr#3 or ascr#9 (0.01 or 0.3 µM) or a mixture of SA (50 µM) and ascr#3 or ascr#9. PR-1 and PDF1.2 expression were detected by semi-quantitative PCR. β-tubulin was used as an internal control.

Figure 13G:
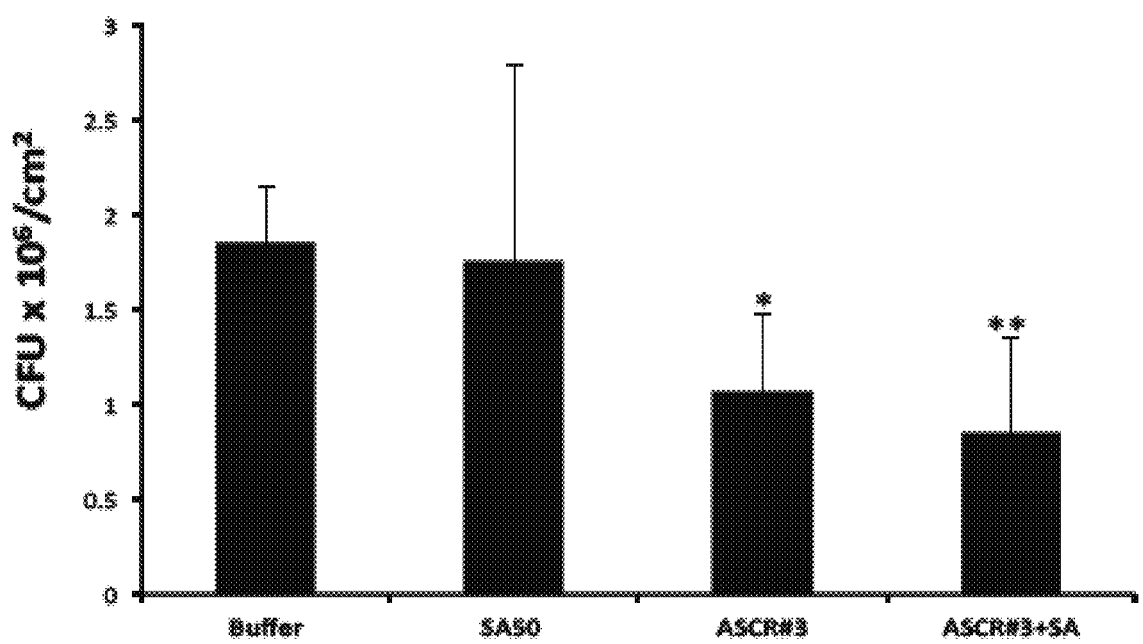
Figure 13H:
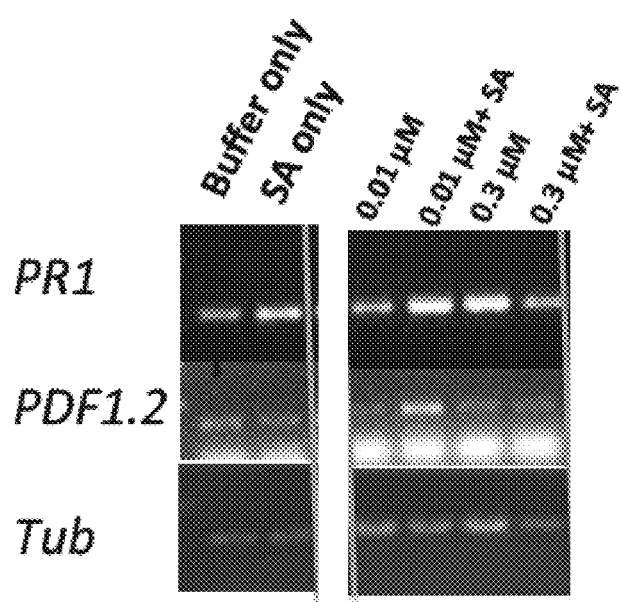
Figure 13I:
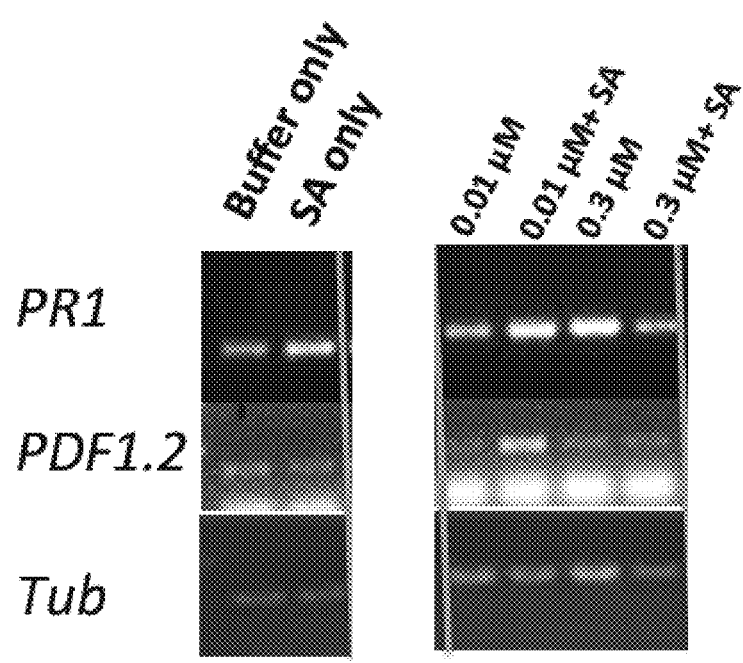

Ascr#3 enhances resistance against virulent *Pseudomonas syringae* pv. tomato (Pst) DC3000 in *Arabidopsis* (FIG. 13G). Ascr#9, oscr#9, and ascr#10 did not significantly enhance resistance against virulent *Pseudomonas syringae* pv. tomato (Pst) DC3000 in *Arabidopsis* at the concentration tested. *Arabidopsis* ecotype Col-0 leaves were treated by syringe infiltration with ascr#3 (0.3 µM) and/or SA (50 µM) 24 hours prior to inoculation with Pst. Bacterial growth was assayed 3 dpi.

Tomato

Figure 14A:
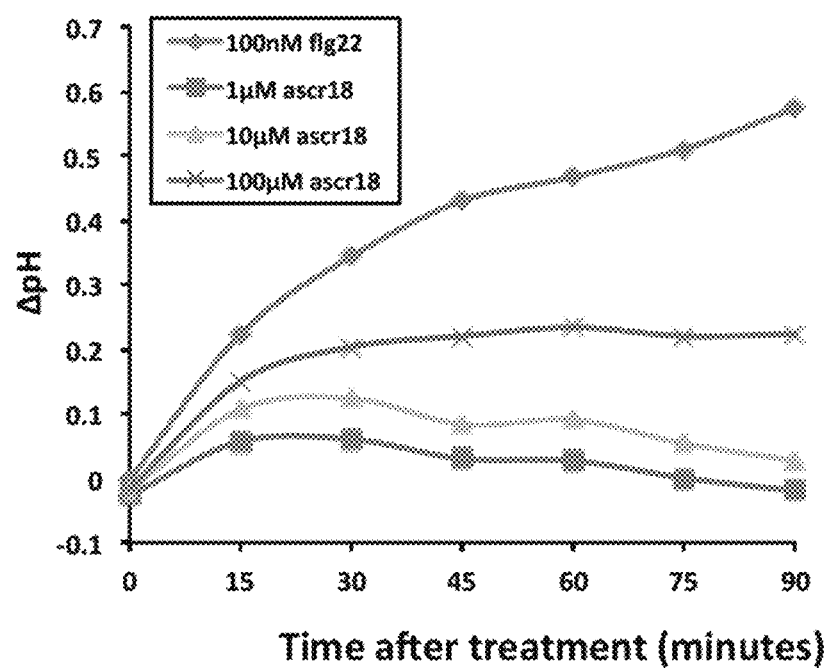
FIGS. 14A, 14B, 14C, 14D, 14E, 14F, and 14G.

One of the first cellular responses after the perception of foreign elicitors is a change in apoplastic pH (Huffaker et al. (2006) PNAS 103:10098-10103). This was mimicked in vitro using tomato suspension cells and monitoring the pH of the culture medium for 90 minutes after addition of the elicitor. Flg22, the active epitope of the prototypic MAMP flagellin, was used as a positive control for the assay. Treatment of tomato suspension cells with ascr#18 (or flg22) induced media alkalinization in a dose-dependent manner (FIG. 14A). Accordingly, media alkalinization can be used as a measurement of the NA's bioactivity in tomato. While ascr#18 enhances resistance in tomato cv. M82 and Rio Grande to virulent US22 strain of the oomycete pathogen *Phytophthora infestans*, ascr#18 did not have a significant effect on resistance against the necrotrophic fungal pathogen *Botrytis cinerea* in tomato cv. M82 at the low concentration of 0.01 µM tested. Higher concentrations may prove effective. Notably, ascr#3 did not have a significant effect on the resistance of M82 against *Phytophthora infestans* at the low concentration of 0.01 µM tested. Higher concentrations may prove effective.

Easc#18 enhances resistance against the virulent necrotrophic fungal pathogen *Botrytis cinerea* in tomato cv. M82

Figure 14B:
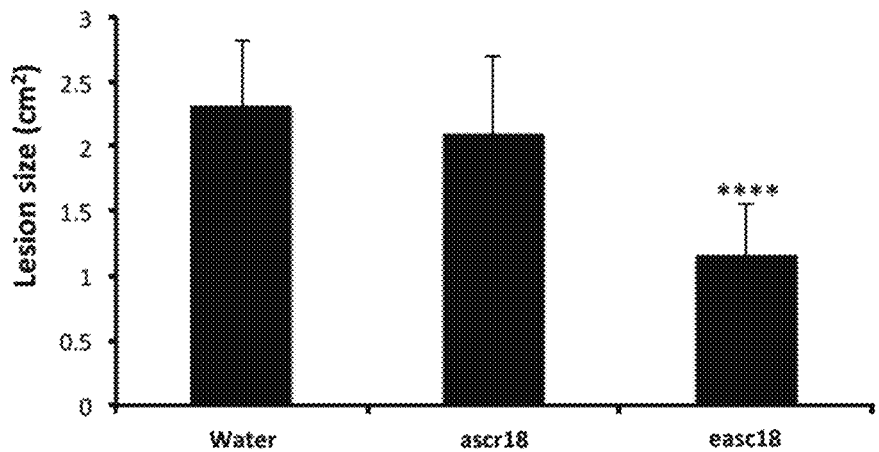
Figure 14C:
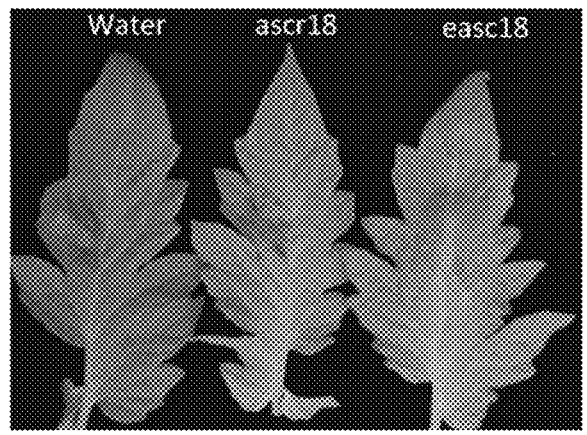

(FIG. 14B and FIG. 14C). Tomato plants were treated via root immersion with water (−) or with 0.01 µM ascr#18 or 0.01 µM easc#18 48 hours before inoculation with the virulent B05.01 strain of *B. cinerea* using a detached leaflet assay.

Figure 14D:
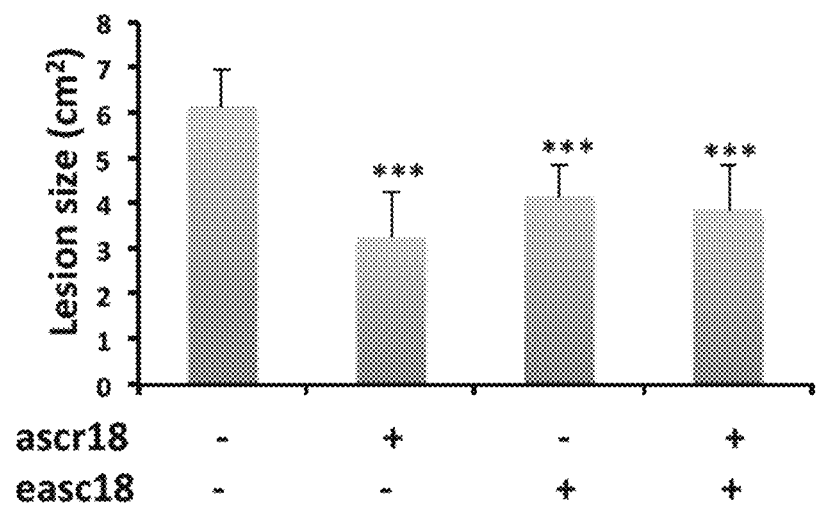
Figure 14E:
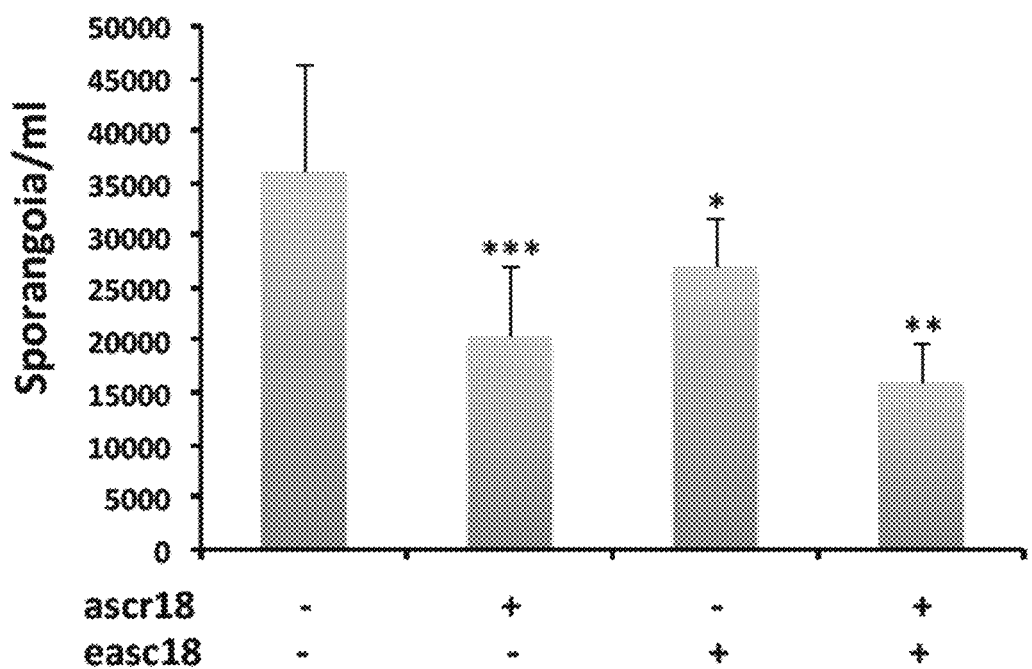

Easc#18 enhances resistance in tomato cv. Rio Grande to virulent US22 strain of the oomycete *P. infestans*, which is comparable with the resistance enhancement by treatment with ascr#18 (FIG. 14D and FIG. 14E). Combination of ascr#18 and easc#18 did not significantly further enhance resistance to *P. infestans*. Tomato plants were treated via root immersion with water (−) or with 0.01 µM of ascr#18, or easc#18, or a combination of both NAs (+) 48 hours before inoculation with *P. infestans* using a detached leaflet assay.

Figure 14F:
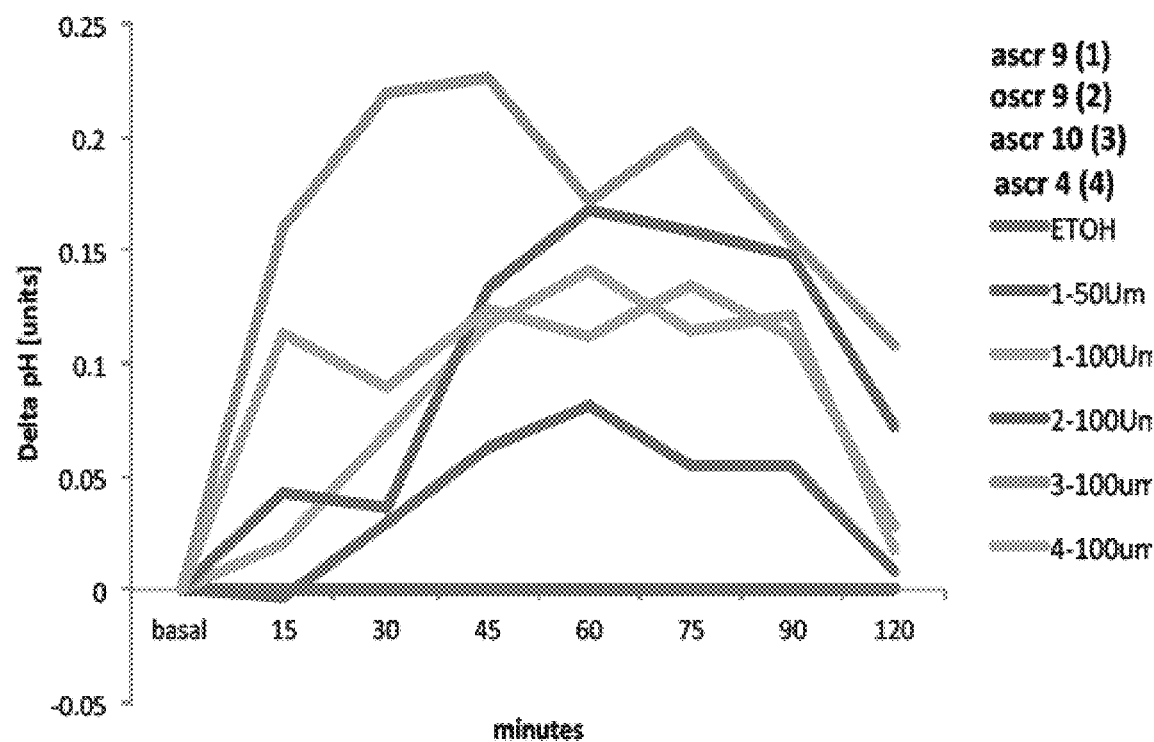

Treatment of tomato suspension cells with four new ascarosides induced media alkalinization (FIG. 14F). As explained above, media alkalinization may be used as a measurement of ascaroside bioactivity in plants.

Figure 14G:
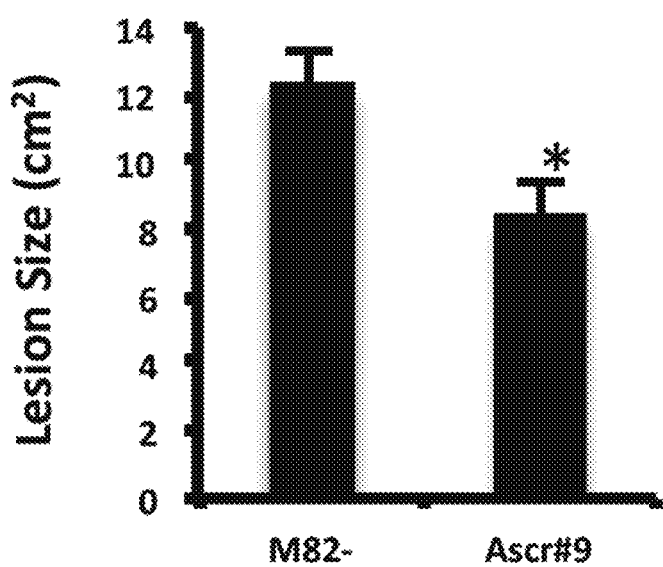

Ascr#9, though not oscr#9 or ascr#10 at the concentration tested, enhances resistance against virulent US22 strain of *P. infestans* in tomato cv. M82 as measured by lesion size (FIG. 14G) and sporangia number. Tomato plants were treated via root immersion with water (−) or with 1 µM ascr#9 48 hours before inoculation with *P. infestans* using a detached leaflet assay. Size of lesion caused by *P. infestans* was determined at 7 dpi.

Barley

Ascr#18 induces PR-1 gene expression in barley at 1 µM concentration. Induction is further enhanced by combination of 1 µM ascr#18 and inoculation with the fungal pathogen Blumeria *graminis* f. sp. *hordei* (Bgh) in barley cv. Golden promise (FIGS. 15A and 15D). Leaves of barley plants were sprayed with various concentrations of ascr#18 or water (mock) for 48 hours. 48 hours post treatment plants were inoculated with Bgh. Leaves were collected at 16 hpi and used to extract RNA for qRT-PCR analysis.

Ascr#18 enhances basal resistance to the fungal pathogen Blumeria *graminis* f. sp. *hordei* (Bgh) in barley cv. Golden promise (FIGS. 15B and 15C). Briefly, barley leaves were sprayed with the indicated concentrations of ascr#18 48 hours before inoculation with Bgh.

Example V

Materials and Methods
Worm Sample Preparation.

Nematode eggs (*M. hapla* strain VW9, *M. incognita* VW6, or *M. javanica* VW4) were extracted from greenhouse-grown tomato plants, and surface-sterile juveniles were prepared as described in (Branch et al. (2004) Mol. Plant Microbe Interact., 17:351-356). *H. glycines* was raised on greenhouse-grown soybean. Batches of approximately 30,000-100,000 freshly hatched juveniles were incubated for 24 hours in 8 ml sterile water with rotation. After brief centrifugation, the supernatant was collected and filtered through a 22 µm filter and then frozen. Filtered supernatants and worm pellets were lyophilized, extracted with 2×5 mL methanol, and filtered over cotton wool. Extracts were concentrated in vacuum and resulting residues were resuspended in 150 µL methanol and filtered prior to mass spectrometric analysis. Analyses of high-resolution mass spectrometry data identified several ascaroside signaling molecules from root knot nematodes.

Mass Spectrometric Analysis.

Low-resolution HPLC-MS and HPLC-MS/MS was performed using an Agilent 1100 Series HPLC system equipped with an Agilent Eclipse XDB-C18 column (9.4×250 mm, 5 µm particle diameter) and connected via a diode array detector to a Quattro II mass spectrometer (Micromass/Waters) using a 10:1 split. A 0.1% acetic acid—acetonitrile solvent gradient was used at a flow rate of 3.6 ml/min, starting with an acetonitrile content of 5% for 5 min which was increased to 100% over a period of 40 minutes. Nematode metabolite extracts (prepared as described above) and synthetic samples (von Reuss et al. (2012) J. Am. Chem. Soc., 134:1817-1824) were analyzed by HPLC-ESI-MS in negative and positive ion modes using a capillary voltage of 3.5 kV and a cone voltage of −40 V and +20 V respectively. HPLC-MS/MS screening for precursor ions of m/z=73.0 (negative mode) and neutral loss of 130.0 (positive mode) was performed using argon as collision gas at 2.1 mtorr and 30 eV. To confirm elemental composition of the identified compounds, samples were additionally analyzed by high-resolution mass spectrometry, using a Waters nanoACQUITY UPLC System equipped with a Waters Acquity UPLC HSS C-18 column (2.1×100 mm, 1.8 µm particle diameter) connected to a Xevo G2 QTof Mass Spectrometer. MassLynx software was used for MS data acquisition and processing.

Plant Material and Growth Conditions.

Unless otherwise stated, *Arabidopsis thaliana* ecotype Col-0, tomato (*Solanum lycopersicum*) cultivar M82, and potato (*S. tuberosum*) cultivars Desiree, Eva, and Yukon Gold plants were grown in a growth chamber under 16-h light/8-h dark (22° C.) regime and 70% relative humidity. *Solanum lycopersicum* and *S. tuberosum* plants were grown in growth chambers for three weeks and then transferred to greenhouse conditions until they were used.

Ascaroside Treatments.

The ascarosides compounds were dissolved in ethanol to made millimolar stock solutions. Final aqueous ascaroside dilutions were made fresh on the day of the experiment. Control solutions contained equal amounts of ethanol (less than 0.1% for most experiments). For leaf treatment, three leaves of 3.5-weeks old *Arabidopsis* plants were syringe infiltrated with buffer (Bis-Tris pH 6.5) supplemented with an ethanolic solution of SA or synthetic ascr#18 or buffer containing an equivalent amount of ethanol. For root treatment, plant pots were placed in a tray containing only water (control) or water supplemented with ascr#18. For spray treatment, leaves were sprayed with an aqueous 0.02% tween-20 solution to which either an ethanol solution of ascr#18 or ethanol (control) had been added.

MAPK Activation/Phosphorylation.

Leaf discs were collected from treated and mock-treated plants at different time points. Leaf tissue was frozen and ground to fine powder before adding 50 µl 4×SDS protein sample buffer. Total cellular proteins were separated by electrophoresis in 8% SDS-PAGE. MAPK activation was detected by immunoblot analyses using polyclonal primary antibodies against phosphor-p44/42 MAPK (Cell Signaling Technology), which detects phosphorylation of the pTE-pY motif responsible for activation.

Plant Infection Assays.

For bacterial growth assays, 3 leaves of 3.5-weeks old treated and untreated *Arabidopsis* were infiltrated with a suspension of virulent Pst. DC3000 in 10 mM $MgCl_2$ at a density of $1 \times 10^5$ colony-forming units (cfu)/ml. 10 mM $MgCl_2$ was infiltrated as a control. Bacterial count was done 3 days post inoculation (dpi) in *Arabidopsis*. Bacterial count was done 3 days post inoculation (dpi) in *Arabidopsis* as described in (Tian et al. (2009) Plant Physiol., 150:815-824). Four-week-old plants were inoculated (Kang et al. (2012) Nat. Commun., 3:1297). TCV in vitro transcripts of a cDNA clone were used at a final concentration of 35 ng/µl and 2 µl were applied per each of three *Arabidopsis* leaves. Quantification of TCV coat protein (CP) was done using immunoblot analyses. For tomato and potato, 6-week old plants were treated with ascr#18 or control solution 48 hours before inoculations. Plants were infected with a virulent strain of *Phytopthora infestans* (US22) using a detached leaflet assay (Manosalva et al. (2010) Mol. Plant Microbe Interact., 23:1151-1163). For Pst bacterial growth assays in tomato, treated and mock-treated plants were vacuum infiltrated with a suspension of virulent Pst DC3000 in 10 mM $MgCl_2$ containing 0.02% Silwet L-77 at a density of $1 \times 10^5$ colony-forming units (cfu)/ml. Plants were dipped upside down in 4 liters of bacterial suspension and a vacuum was applied for 1 or 2 minutes followed by a slow release to infiltrate the leaves uniformly. Plants were then incubated in a growth chamber with 16-h illumination and 60% humidity at 22° C. Bacterial count was done 4 days post inoculation (dpi).

For barley cv. Golden Promise, 7-days old seedlings were pretreated by spraying with different concentrations of ascr#18. Inoculation with Bgh was done 48 hours post treatment using a detached leaflet assay. Briefly 10 leaves from 5 different plants per treatment were cut and transferred to Petri dishes containing 1% water agar. Leaves were then inoculated with Bgh. Water was used as mock control. Pustules were counted 7 dpi.

For *Arabidopsis* cyst nematode infection, *H. schachtii* and *M. incognita* were propagated and hatched (Hamamouch et al. (2012) J. Exp. Bot., 63:3683-3695). *Arabidopsis thaliana* ecotype Col-0 seeds were surface sterilized and planted in 6-well plates with Knop medium contained 2% sucrose (Sijmons et al. (1991) Plant J., 1:245-254). Plants were grown at 24° C. under 16-h-light/8-h-dark conditions. 2 mL of various concentrations of ascr#18 or control solution were added to each well containing 10-day-old seedlings. After 48 hours of pretreatment, the solution was removed and approximately 200 freshly hatched and surface-sterilized juveniles (J2) of *H. schachtii* or approximately 300 freshly hatched and surface-sterilized J2 of *M. incognita* were inoculated on each seedling as described (Hamamouch et al. (2012) J. Exp. Bot., 63:3683-3695). Twenty-four seedlings were included for each treatment. Nematode females for *H. schachtii* were counted under microscope four weeks after inoculation. Galls for *M. incognita* were counted under microscope six weeks after inoculation.

RNA Analyses.

Unless stated otherwise, three biological replications were performed. For each biological replication, total RNA from *Arabidopsis* was isolated from a pool of one leaf from each of three plants. For tomato, RNA was isolated from six leaf discs per leaf per plant. Total RNA was isolated using Qiagene RNeasy Plant Mini Kit (Qiagen) according to manufacturer's instructions. DNAse treatment was done using DNA-Free™ Kit (Ambion) following the manufacturer's instructions. First-strand cDNA was synthesized from 1 µg of RNA using SuperScript II (Life Technologies) and amplified using gene-specific primers (Table 1). Control reactions to normalize RT-PCR amplifications were run with the primers for constitutively expressed *Arabidopsis* β-tubulin and from tomato translation elongation factor 1α (EF1α) gene. For quantitative real-time PCR (qRT-PCR), transcripts were amplified using IQ SYBR Green Supermix (Bio-Rad) from 5 µl of 10×-diluted cDNA in a total 20 µl reaction using 1 µl of 10 mM gene-specific primers. Reactions were done using CFX96 Touch Biorad Real-Time PCR System (Biorad). The PCR conditions were 95° C. for 3 min (initial denaturation) followed by 40 cycles of amplification (95° C. for 15 sec, 60° C. for 60 sec), followed by generation of a dissociation curve. Three technical replicates were performed for each biological replicate. The transcript level of defense response genes in *Arabidopsis* and tomato are shown as fold change relative to mock-treated plants. The relative fold change was calculated according to the $2^{-\Delta\Delta Ct}$ method (Livak et al. (2001) Methods 25:402-408). *Ubiquitin* (*Arabidopsis*) and *actin* (tomato) were used as endogenous reference genes. The paired t-test with an a level of 0.05 was used to compare transcript level in the ascr#18-treated versus the mock-treated samples.

TABLE 1

Primers. Sequences are SEQ ID NOs: 1-56, from top to bottom.

| Primer Name | Sequence |
|---|---|
| AtPR-1 F | TCGTCTTTGTAGCTCTTGTAGGTG |
| AtPR-1 R | TAGATTCTCGTAATCTCAGCTCT |
| AtPDF1.2-F | TCATGGCTAAGTTTGCTTCC |
| AtPDF1.2-R | AATACACACGATTAGCACC |
| AtTubulin-S | GTCCAGTGTCTGTGATATTGCACC |
| AtTubulin-R | TTACGAATCCGAGGGAGCCATTG |
| HvPR1b-F | GGACTACGACTACGGCTCCA |
| HvPR1b-R | GGCTCGTAGTTGCAGGTGAT |
| HvUbiquitin-F | ACCCTCGCCGACTACAACAT |
| HvUbiquitin-F | CAGTAGTGGCGGTCGAAGTG |
| AtFRK1-fw | TGCAGCGCAAGGACTAGAG |
| AtFRK1-rv | ATCTTCGCTTGGAGCTTCTC |
| AtPHI-fw | TTGGTTTAGACGGGATGGTG |
| AtPHI-rv | ACTCCAGTACAAGCCGATCC |
| qAtUBQ-fw | GGCCTTGTATAATCCCTGATGAATAAG |
| qAtUBQ-rv | AAAGAGATAACAGGAACGGAAACATAG |
| AtPR4-F | CTGGACCGCCTTCTGCGGG |
| AtPR4-R | AGCCTCCGTTGCTGCATTGGT |
| AtAOS-F | TCTTCTCTTCGCCACGTGC |
| AtAOS-R | GGTTATGAACTTGATGACCCGC |
| AtLOX2-F | TTGCTCGCCAGACACTTGC |
| AtLOX2-R | GGGATCACCATAAACGGCC |
| AtGSTF6-F | GGCAGGAATCAAAGTTTTCG |
| ATGSTF6-R | CGACCAAAGTGAAGTGGTCA |
| LeGST-F | GCCCTTCCATCTTGCCTAAAG |
| LeGST-R | GTCACCAAAACAACTCCAGATGC |
| Leβ-1,3-glucanase-F | TGCTACATACTCGGCCCTTGAA |
| Leβ-1,3-glucanase-R | TTTGGCTGCCTGTTTGGTGT |
| LeGRAS4 | CCGTCCTGATTTATTCATCCAT |
| LeGRAS4 | TCGTGTGACGAAAAATGGAGT |

TABLE 1-continued

Primers. Sequences are SEQ ID NOs: 1-56, from top to bottom.

| Primer Name | Sequence |
|---|---|
| LeActin | GAGCGTGGTTACTCGTTCA |
| LeActin | GAGCGTGGTTACTCGTTCA |
| LeAOS2-F | GCAACGAAGGATCCGAAAAT |
| LeAOS2-R | ACTGGCCGATAGTGACAGTG |
| qEBF1-F | CAGATCTTTAGTTTTGCCGGTGA |
| qEBF1-R | AGCATCCTTTGGGTTTGGGT |
| qERS1-F | CTGATTCTGTCTGCAGA |
| qERS1-R | TGTGTGAATTCCACACCCTGTG |
| qERS2-F | GCCAAAACATTGTAAAGTATATGCA |
| qERS2-F | CTTCCTGACGTCAATGATCAGT |
| qERF1-F | TTTCTCGATGAGAGGGTC |
| qERF1-R | AAGCTCCTCAAGGTACTG |
| qACO1-F | AGGAACTCAGCAAGACGATGG |
| qACO1-R | GACGTGGGCATTCTGGGTAT |
| qSAUR34-F | CGACAGTTCCAAGAGGGCAT |
| qSAUR34-R | GTTCAAACCCGTAAACCCGC |
| qDRM2-F | CCCTTGACATCAAAGGTGTAGGA |
| qDRM2-R | GGGTGAGAAGGCTTGTCGAA |
| qAUX1-F | GATGAGATAAGCAGTCCAGCTTCC |
| qAUX1-R | CAGCTGCGCATCTAACCAAGTG |
| qIAA6-F | TTCGATTGGGTCTTCCAGGAGATA |
| qIAA6-R | ATCTTGCTGGAGACCAAAACCA |
| qARF19-F | CCTCCTGTGGGAAGTCTTGTGGTTTAC |
| qARF19-R | GCTCCAACCTGTGGTAAGCAAGTG |
| qWRKY53-F | TCACTTTTTCTGACCACTTTGG |
| qWRKY53-R | AAGGAAGAGATATGTTAAGTTGGG |

For barley analyses, RNA extraction from infected barley leaves was performed with TRIzol (Invitrogen) following the manufacturer's instructions. Freshly extracted mRNA was used for cDNA synthesis using QuantiTect Reverse-Transcription kit (Qiagen). cDNA was stored at −20° C. For qRT-PCR, 50 ng of cDNA was used as template in the Applied Biosystems 7500 FAST real time PCR system. Amplifications were performed in 7.5 µL of SYBER green JumpStart Taq ReadyMix (Sigma-Aldrich) with 0.5 pmol oligonucleotides. Relative quantification of the transcript abundance for barley genes were done using the $2^{\Delta Ct}$ method as described (Floss et al. (2013) Proc. Natl. Acad. Sci., 10: E5025-5034). In barley, Ubiquitin was used as an endogenous reference gene.

For the RNA analyses in roots, Arabidopsis roots were collected from 20-30 seedlings from each treatment and mRNA was isolated using the Dynabeads mRNA DIRECT Kit (Life Technologies). DNA contamination was removed by treatment with DNase I (Life Technologies). First-strand cDNA was synthesized from 50 ng of mRNA using Proto-Script II Reverse Transcriptase (NEB). The qRT-PCR assay was carried out in an iCycler iQ Real-Time PCR Detection System (Bio-Rad) and transcripts were amplified using iTaq™ Universal SYBR Green Supermix (Bio-Rad) from 1 µL of 20×-diluted cDNA in a total 20 µL reaction using 1 µL of each 10 µM gene-specific primer (Table 1). All assays consisted of three technical replicates for each RNA sample. Data was analyzed using the iCycler iQ Real-Time PCR Detection System Software version 3.0a (Bio-Rad). The Arabidopsis UFP gene (AT4G01000) was used as an endogenous reference gene. PCR was started with an activation and DNA denaturation step (95° C. for 3 minutes), then followed by 40 cycles of 95° C. for 20 seconds and 60° C. for 40 seconds. The relative fold change was calculated according to the $2^{-\Delta\Delta Ct}$ method (Livak et al. (2001) Methods 25:402-408).

Results

Plant-Parasitic Nematodes Produce Ascarosides

The exo-metabolome produced by infective juveniles of three species of root-knot nematodes, Meloidogyne incognita, M. javanica, and M. hapla, as well as cyst (Heterodera glycines) and lesion (Pratylenchus brachyurus) nematodes, was analyzed using a recently developed mass spectrometric screening protocol that enables detection of femtomolar concentrations of ascarosides. This HPLC-MS-based technique relies on monitoring a mass spectrometric fragmentation pathway that is high specific for ascarosides (the formation of a fragment ion corresponding to $C_3O_2H_5$ in negative-ion electrospray ionization mode) and subsequent confirmation of the structures of the detected ascarosides using authentic synthetic standards (von Reuss et al. (2012) J. Am. Chem. Soc., 134:1817-1824). HPLC-MS analysis of exo-metabolome samples obtained from overnight incubation of infective juveniles consistently revealed excretion of a series of ascarosides with simple saturated side chains in all analyzed species (Table 2). In all three Meloidogyne species, ascr#18, a compound featuring an 11-carbon side chain, was most abundant, followed by compounds with 12, 13, and 15 carbon side chains (ascr#20, ascr#22 and ascr#26, respectively) (FIGS. 16H and 16I and Table 2). Concentrations of ascr#18 in the analyzed Meloidogyne spp. culture media samples were variable and ranged from 5 nM to 100 nM. All Meloidogyne species additionally produce trace amounts of ascr#24 and the shorter-chained ascarosides ascr#10 and ascr#16. Ascr#18 was the by far most abundantly produced ascaroside, accounting for more than 70% of total ascaroside content in the exo-metabolome samples of infective juveniles from all three species. Analysis of H. glycines, and P. penetrans infective juveniles also revealed ascr#18, albeit in much smaller amounts than in Meloidogyne spp. infective juvenile. No other ascarosides were detected in these two species. Exo-metabolome samples of adult M. hapla, H. glycines, and P. brachyurus contained trace amounts of ascr#18, whereas the other ascarosides found in infective juveniles could not be detected in adults.

TABLE 2

Chemical structures and high-resolution mass spectroscopic data, acquired in negative-ion electrospray ionization mode, of ascarosides detected in plant-parasitic nematodes.

| SMID | n[a] | m/z [M − H]⁻, calculated | m/z [M − H]⁻, observed | M. hapla | M. incognita | M. javanica | H. glycines | P. brachyurus |
|---|---|---|---|---|---|---|---|---|
| ascr#10 | 6 | 303.1808 | 303.1813 | x | x | x | o | o |
| ascr#16 | 7 | 317.1964 | 317.1959 | x | x | x | o | o |
| ascr#18 | 8 | 331.2121 | 331.2129 | x | x | x | x | x |
| ascr#20 | 9 | 345.2277 | 345.2267 | x | x | x | o | o |
| ascr#22 | 10 | 359.2434 | 359.2429 | x | x | x | o | o |
| ascr#24 | 11 | 373.2596 | 373.2653 | x | x | x | o | o |
| ascr#26 | 12 | 387.2752 | 287.2727 | x | x | x | o | o | x: present;
o: not detected.
SMID: Small Molecule IDentifier, see www.smid-db.org for details on nomenclature.
[a]n: number of $CH_2$ groups in the side chains of the ascarosides:

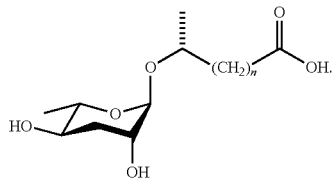

These results show that plant-parasitic nematodes, like most other previously analyzed nematode species (Choe et al. (2012) Curr. Biol., 22:772-780), produce ascarosides. Notably, the analyzed species from the three main genera of plant-parasitic nematodes all produce the same ascaroside, ascr#18, most abundantly. Ascr#18 had previously been identified as a minor component of the ascaroside profile produced by the model organism C. elegans (von Reuss et al. (2012) J. Am. Chem. Soc., 134:1817-1824) and also occurs in entomopathogenic nematodes, e.g. Heterorhabditis bacteriophora (Choe et al. (2012) Curr. Biol., 22:772-780; Noguez et al. (2012) ACS Chem. Biol., 7:961-966).

Ascr#18 Induces Defense Responses and Enhances Resistance in Arabidopsis.

The effect of ascr#18 on the defense responses of Arabidopsis to a bacterial and a viral pathogen were tested (FIG. 16). Since plants would naturally encounter nematodes via their roots, Arabidopsis roots were partially immersed in water containing different concentrations of ascr#18 for 24 hours before leaves were inoculated with the pathogens. Root treatment with 1 μM ascr#18 resulted in reduced growth of the virulent bacterial pathogen Pseudomonas syringae pv tomato (Pst) DC3000, whereas a higher ascr#18 concentration (5 μM) appeared to be less effective (FIG. 13A).

Pretreatment of Arabidopsis roots with 1 μM ascr#18 at 1 μM also dramatically enhanced resistance to virulent Turnip Crinkle Virus (TCV). Viral replication, as measured by the amount of viral coat protein using an immune blot assay (FIG. 16A), was greatly reduced in both inoculated and distal leaves of ascr#18-pretreated plants. Moreover, systemic spread of the virus was largely abolished with only a trace of coat protein present in distal leaves of ascr#18 pretreated plants. Consistent with the molecular data, disease symptoms, including development of chlorosis and lesions on the inoculated leaves (FIG. 16B) and suppression of inflorescent development (FIG. 16C), were greatly reduced in ascr#18 pretreated plants.

To further characterize Arabidopsis' response to ascr#18, the expression of defense-related genes in leaves were monitored after root treatment with 1 μM ascr#18 at several different time points. Mitogen-Activated Protein Kinase (MAPK) and calcium-dependent protein kinase (CDPK) are key components of signaling pathways that regulate recognition of MAMPs/DAMPs/HAMPs by plants (Boudsocq et al. (2010) Nature 464:418-422; Asai et al. (2002) Nature 415:977-983; Bonaventure et al. (2011) Trends Plant Sci., 16:294-299). Therefore, induction of the MAPK-related Flg22-induced receptor kinase1 (FRK1) and the CDPK-related phosphate-induced1 (PHI1) marker genes (Boudsocq et al. (2010) Nature 464:418-422) were measured after ascr#18 treatment. It was found that ascr#18 treatment induced FRK1 and PHI1 in the leaves at 6 and 24 hours post treatment (hpt), respectively (FIG. 16D). In addition, expression of representative biosynthetic or responsive genes for the two major hormones mediating plant immunity, salicylic acid (SA) and jasmonic acid (JA), were measured in leaves. It was found that ascr#18 root treatment increased expression of the SA-responsive genes pathogenesis-related 4 (PR-4), which encodes chitinase type II, and glutathione-S-transferase F6 (GSTF6), and the JA-biosynthetic genes lipoxygenase2 (LOX2) and allene oxide synthase (AOS) in leaves (FIG. 16D) (Robert-Seilaniantz et al. (2011) Annu. Rev. Phytopathol., 49:317-343).

Because JA and SA signaling interact with the ethylene (ET) and auxin signaling pathways (Robert-Seilaniantz et al. (2011) Annu. Rev. Phytopathol., 49:317-343), changes in the expression of five genes associated with ET signaling as well as five genes associated with auxin signaling were monitored in response to root treatment with 1 μM ascr#18 at 24 hpt. Of the 10 tested genes, only expression of SAUR-LIKE AUXIN RESPONSE PROTEIN34 (SAUR34) was enhanced (FIG. 16G), indicating that ascr#18 treatment does not strongly affect auxin or ET-regulated defense signaling.

As explained above, it was tested whether plants respond to ascr#18 via their leaves. Pretreating leaves with 0.3 μM ascr#18 via leaf infiltration provided a low level of protection against Pst, similar to that obtained with 50 μM SA. However, co-treatment with ascr#18 and SA strongly enhanced resistance (FIG. 6). It was then tested whether ascr#18 leaf treatment induced activation of the MAPKs, MPK3 and MPK6, as early markers for the development of pattern-triggered immunity (PTI) (Asai et al. (2002) Nature 415:977-983). MAPK activation following leaf infiltration with a range of ascr#18 concentrations was monitored via immunoblot analysis using an antibody that detects phosphorylation of the pTE-pY motif (Flury et al. (2013) Plant Physiol., 161:2023-2035). A transient increase in the phosphorylation of both MAPKs 10 minutes after leaf infiltration with 1 µM ascr#18 was observed (FIG. 16E). In addition, transcripts for the prototypic SA-responsive marker PR-1 and prototypic JA-responsive PDF1.2 genes (Robert-Seilaniantz et al. (2011) Annu. Rev. Phytopathol., 49:317-343) were elevated at 24 hpt after infiltration with 0.01 µM or 0.3 µM ascr#18 (FIG. 16F). Induction of PR-1 expression by 0.3 µM ascr#18 was similar to that induced by a suboptimal concentration of SA (50 µM). Taken together the results indicate that in Arabidopsis, local and systemic defenses are activated in response to ascr#18 over a wide range of concentrations applied to either roots or leaves, triggering both, early defense responses including activation of MAPKs and induction of PTI-responsive marker genes as well as late responses such as induction of PRs and PDF1.2 gene expression.

Asrc#18 Enhances Resistance in Both Dicot and Monocot Crop Plants Against Diverse Pathogens.

To test whether ascaroside perception is conserved across the plant kingdom and to investigate responses to eukaryote pathogens, defense gene expression and/or pathogen resistance was measured following ascr#18 treatment of the dicots tomato (Solanum lycopersicum) and potato (Solanum tuberosum), as well as the monocot barley (Hordeum vulgare). Ascr#18 was found to induce defenses in both Solanum species. Roots of tomato cv. M82 were pretreated for 48 hours with ascr#18 concentrations ranging from 0.01 nM to 100 nM. Very low concentrations of 1 nM and 10 nM provided strong protection against the virulent US22 strain of the oomycete pathogen Phytophthora infestans, as indicated by the reduction in sporangia number and lesion size (FIGS. 17A-17C). Similar to the effect of ascr#18 on resistance of Arabidopsis to Pst, protection against P. infestans in tomato decreased at higher concentrations of ascr#18. However, maximal protection was observed at ascr#18 concentrations (1-10 nM), much lower than in the case of Arabidopsis (1 µM). Root treatment with 10 nM ascr#18 also significantly reduced the growth of the virulent bacterial pathogen, Pst strain DC3000, in tomato leaves (FIG. 17D), whereas higher concentrations were less effective. As in Arabidopsis, root treatment of tomato cv. M82 with ascr#18 (10 nM) induced the accumulation of transcripts for (i) the transcription factor GRAS4, a known marker of MAMP-triggered immunity linked to abiotic and biotic responses in tomato (Taylor et al. (2012) PLoS Pathog 8:e1002768), (ii) the SA-responsive genes GST and β-1,3-glucanase, and (iii) the JA-biosynthesis gene AOS2 in the leaves (Robert-Seilaniantz et al. (2011) Annu. Rev. Phytopathol., 49:317-343) (FIG. 17E). Transcript levels for all four genes were significantly elevated at 48 hpt, with β-1,3-glucanase also exhibiting enhanced levels at 24 hpt. Pretreatment with 10 nM ascr#18 either by root immersion or foliar spray 48 hours prior to inoculation also provided protection against virulent P. infestans in potato cv. Desire, Eva or Yukon Gold (FIG. 10, 17F).

To determine whether ascr#18 also activates defense responses in monocots, leaves of barley (Hordeum vulgare) cv. Golden Promise were sprayed with ascr#18 48 hours prior to inoculation with the virulent fungal pathogen Blumeria graminis f. sp. hordei (Bgh). As described above, pretreatment with 0.01 µM to 1 µM ascr#18 increased resistance to Bgh, based on the reduced numbers of pustules formed on the leaves (FIG. 15C). Spraying barley leaves with ascr#18 also induced PR-1 transcript accumulation; even higher levels of PR-1 expression were observed in ascr#18-pretreated leaves that also were inoculated with Bgh, indicating a priming effect of ascr#18 in barley (FIG. 15D). Lastly, the possibility that the observed increases in pathogen-resistance are the result of anti-bacterial or anti-fungal activity of ascr#18 was considered. However, disk-diffusion assays using E. coli, B. subtilis, and Aspergillus fumigatus showed no growth inhibition up 10 mM of ascr#18. Taken together, these results show that ascr#18 is perceived by monocots and dicots and induces defense responses that enhance resistance against all four major classes of pathogens.

Plant Responses to Other Ascarosides

In order to assess whether plants respond to ascarosides as a compound class and whether specific structural features of ascr#18 are required for plant responses, several additional ascarosides were tested for their ability to induce defense responses. For this, the following were selected: ascr#3, an ascaroside that includes a conjugated double bond in the side chain, ascr#9, whose side chain (5 carbon) is much shorter than that of ascr#18 (11 carbons), and oscr#9, which features a terminally (w) oxygenated side chain, in contrast to all other tested ascarosides, which are w-1 oxygenated. Similar to ascr#18, leaf treatment with either ascr#3 or ascr#9 induced expression of the prototypic SA-responsive PR-1 and JA-responsive PDF1.2 genes, whereas oscr#9 showed little or no effect (Table 3). Moreover, root treatment of tomato cv. M82 with ascr#9, like ascr#18, enhanced resistance to P. infestans, while neither ascr#3 nor oscr#9 affected resistance to this pathogen at the concentrations tested. These results argue that plant responses to ascarosides vary in a structure-dependent manner. Notably, oscr#9, whose structures differs from that of ascr#9 only in the position of the attachment of the side chain to ascarylose, was inactive in all assays whereas ascr#9 was active. The possibility that the observed increases in pathogen resistance were due to anti-bacterial or anti-fungal activity of ascarosides is unlikely since ascaroside concentrations up to 10 mM did not inhibit the growth of E. coli, Bacillus subtilis, or Aspergillus fumigatus in disk-diffusion assays, consistent with previous study showing that ascaroside-containing C. elegans metabolome samples have no antimicrobial activity (Kaplan et al. (2009) J. Chem. Ecol., 35:878-892).

TABLE 3

Induction of plant immune responses with various ascarosides. Leaf pretreatment by syringe infiltration of different ascarosideconcentrations (0.01, 0.3, and 10 µM) were used for PR-1/PDF1.2expression studies in Arabidopsis. Resistance to P. infestans in tomato (M82) was performed using root pretreatment with 0.01 or 1 µM ascaroside. (+) indicates enhanced expression or resistance while (−) indicates no effect.

| | ascr#18 | ascr#3 | ascr#9 | oscr#9 |
|---|---|---|---|---|
| PR-1 expression in Arabidopsis | + | + | + | ± |
| PDF1.2 expression in Arabidopsis | + | + | + | − |
| P. infestans resistance in tomato | + | − | + | − |

Ascr#18 Affects Plant-Nematode Interactions

As explained above, it was determined whether ascr#18 affects infection of Arabidopsis with plant-parasitic nematodes. Testing a range of ascr#18 concentrations, it was found that pretreatment of roots with 10 nM ascr#18 significantly reduced infection of Arabidopsis with cyst (*H. schachtii*) and root knot (*M. incognita*) nematodes (FIGS. 18A and 18B), whereas higher concentrations of asctr#18 were less effective. Next, it was determined whether treatment of Arabidopsis with nanomolar concentrations of ascr#18 affected root expression of the defense-related genes PHI1, FRK1, and WRKY53, which encodes an immune-modulating transcription factor. It was found that all three genes were induced within 6 hours of exposure to 10 or 50 nM ascr#18, whereas exposure to a higher concentration (300 nM) had no effect or reduced expression (FIG. 18C).

Notably, the ascr#18 concentration providing best protection against root infection with *H. schachtii* in *Arabidopsis* was substantially lower than the concentration needed for best protection against leaf infection with Pst (1 µM). This may reflect differences in distance between the sites of infection from the site of ascr#18 application; however, it is also possible that the observed reduction in *H. schachtii* infection levels was due to a direct effect of ascr#18 on this nematode.

Ascarosides are small molecules of diverse structure that have been shown to play critical signaling functions for many aspects of nematode life history, including development, phenotypic plasticity, aging, reproduction, and social behaviors (Artyukhin et al. (2013) J Biol Chem., 288:18778-18783; Bose et al. (2012) Angew Chem Int Ed Engl., 51:12438-12443; Choe et al. (2012) Proc Natl Acad Sci., 109:20949-20954; Choe et al. (2012) Curr Biol., 22:772-780; Ludewig and Schroeder (2013) WormBook, 1-22; Noguez et al. (2012) ACS Chem Biol., 7:961-966). The work herein shows that these conserved nematode signaling molecules function as general elicitors of leaf and root defense responses and enhance resistance to a broad-spectrum of pathogen and pests in plants. Together, these results show that ascarosides, which have been identified only in nematodes, are recognized by plants as a unique, foreign molecular signature that activates conserved plant immune responses. Therefore, ascarosides may be designated as Nematode-Associated Molecular Patterns (NAMPs), in keeping with immunity-associated terminology such as MAMPs, DAMPs, HAMPs (Bianchi, M. E. (2007) J Leukocyte Biol., 81:1-5; Mithofer and Boland (2008) Plant Physiol., 146: 825-831). Similar to MAMPs, plants appear to have evolved a yet unidentified receptor(s) that detects very low concentrations of NAMPs.

Similarly, ascarosides are perceived at nanomolar and even picomolar concentrations in animals. For example, the male-produced sex pheromone in *Caenorhabditis elegans* is a mixture of three ascarosides, ascr#2, ascr#3, and ascr#8, which are active at low nanomolar concentrations (Pungaliya et al. (2009) Proc Natl Acad Sci., 106:7708-7713). The most potent ascaroside identified so far, a compound named hbas#3 that promotes aggregation behaviors in *C. elegans*, is active at femtomolar concentrations (von Reuss et al. (2012) J Am Chem Soc., 134:1817-1824). The results herein indicate that plants respond to nanomolar ascr#18 concentrations; for example, in tomato as little as 0.01 nM ascr#18 enhanced resistance against the virulent US22 strain of the oomycete pathogen *Phytophthora infestans*. Comparable concentrations of well-characterized bacterial MAMPs, e.g. the flagellin-derived flg22 or elf18, a MAMP derived from the prokaryotic elongation factor EF-Tu, induce defense responses in plants. However, these peptide MAMPs represent much larger molecules than ascr#18. Similar to bacterial MAMPs, sensitivity to ascarosides varied between plant species: in tomato, potato, and barley 10 nM ascr#18 strongly induced defense gene expression and enhanced resistance, whereas *Arabidopsis* required higher concentrations. Notably, in both *Arabidopsis* and tomato, efficacy decreased at the highest tested ascr#18 concentrations. For example, in tomato ascr#18 concentrations of 1-10 nM provided maximal resistance against virulent US22 strain of the oomycete pathogen *Phytophthora infestans*, whereas enhancement of resistance was reduced or lost at 100 nM. A similar decrease of activity at higher concentrations has been observed for ascaroside-mediated phenotypes in nematodes. For example, attraction of male *C. elegans* to hermaphrodite-produced ascarosides as well as aggregation of *C. elegans* hermaphrodites in response to indole ascarosides is maximal at picomolar concentrations, but decreases markedly at higher concentrations (Srinivasan et al. (2008) Nature 454:1115-1118; Srinivasan et al. (2012) PLoS Biol., 10:e1001237). The cause of the observed decrease in activity at higher ascaroside concentrations in not known. However, it has been suggested that high concentrations of small-molecule ligands can result in unproductive engagement of receptors, for example, by interfering with formation of receptor dimmers (Qureshi et al. (1999) PNAS 96:12156-12161), which have been shown to be required for ascaroside perception in *C. elegans* (Park et al. (2012) PNAS 109:9917-9922).

Herein, root treatment with ascr#18 leads to the activation of both local and systemic defenses. The induction of defense genes and pathogen resistance in leaves following root immersion suggests that ascr#18 itself (or a metabolite of ascr#18) moves from the roots to the leaves and/or that ascr#18 induces synthesis of a mobile signal in the roots that then travels to the leaves to activate immune responses. Although plants naturally encounter ascarosides via their roots, leaf infiltration and foliar spraying with low ascr#18 concentrations were also effective at inducing defense responses. This finding indicates that ascaroside receptors may also be present in leaf tissue. The ascr#18 concentration providing best protection against root infection with the root knot and cyst nematodes (10 nM) in *Arabidopsis* was much lower than the concentration needed for best protection against leaf infection with bacterial and viral pathogens tested (1 µM). This may reflect higher expression of ascaroside receptors in the roots or differences in the distances between the sites of infection from the site of ascr#18 application or perception. In addition, the observed reduction of nematode infection levels may be due to direct effects of ascr#18 on these nematode species, which remain to be investigated. However, the induction of defense-associated genes in the roots at the effective ascr#18 concentration indicate that the increased resistance is, at least in part, mediated by enhanced immunity. Nanomolar concentrations of ascr#18 are representative of those found in culture media samples of the analyzed plant parasitic nematode species, supporting the biological significance of ascr#18 in plant-nematode interactions.

MAMPs have been shown to trigger defense responses via the activation of MAPKs and CDPKs. Similarly, it was found that ascr#18 induced the activation of two MAPKs, MPK3 and MPK6, and their downstream target gene FRK1. The MAMP marker gene, PHIL which is specifically induced by CDPKs, is also induced by ascr#18, suggesting the activation of the CDPK pathway. MAMP perception is functionally connected to the SA- and JA-pathways. Consistent with this, it was found that low concentration of ascr#18 activated both SA- and JA-mediated defense signaling and increases resistance to viral, bacterial, fungal, and oomycete pathogens. It is well know that JA-dependent Induced Systemic Resistance (ISR) is triggered by root colonization with symbiotic microorganisms as well as nematodes. It was shown that treatment of roots with ascr#18 induced the expression of JA-biosynthetic genes in *Arabidopsis* and tomato leaves, indicating that ISR may partly underlie ascr#18-induced systemic protection to foliar pathogens.

Thus, it has been demonstrated that ascarosides are an animal-derived conserved molecular pattern that activates defense responses in plants at very low concentrations and induces both local and systemic resistance to a broad range of pathogens. Using ascarosides or their derivatives to prime or activate plant immune systems could improve the economic and environmental sustainability of agriculture.

Example VI

Synthesis of ascr#18

Starting materials were synthesized as described in cited references or purchased from Sigma-Aldrich or Acros Organics and used without further purification. Anhydrous solvents were prepared with 4 Å molecular sieves. NMR spectra were recorded on a Varian INOVA-600 (600 MHz for ¹H, 151 MHz for ¹³C), INOVA-500 (500 MHz for ¹H and 125 MHz for ¹³C), and INOVA-400 (400 MHz for ¹H, 100 MHz for ¹³C) instruments. Flash chromatography was performed using a Teledyne ISCO CombiFlash system.

Step 1. (9R)-hydroxydec-1-ene

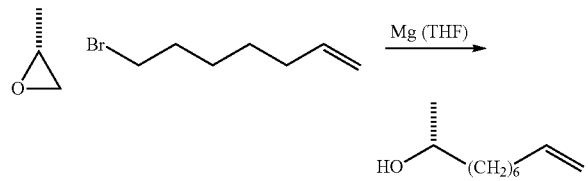

A solution of 7-bromoheptene (300 µg, 2 mmol) in dry THF (1 mL) was added drop wise to magnesium (240 mg, activated with iodine) in THF (500 µL). After stirring at RT for 1 hour the Grignard solution was transferred, cooled to −40° C. and treated with CuI (30 mg, 158 mol). After stirring for 1 min (R)-propylene oxide (100 µL, 2 mmol) in THF (500 µL) was added and the solution stirred for 1.5 h. The reaction was quenched with NH₄Cl (1 mL), extracted with diethyl ether, dried over Na₂SO₄, and concentrated in vacuum. Flash column chromatography on silica gel using an ethyl acetate-hexane gradient (0 to 20%) afforded (8R)-hydroxydec-1-ene (56 mg, 359 mol, 18% yield) as a colorless liquid. ¹H NMR (600 MHz, chloroform-d): δ 1.18 (3H, d, J=6.2 Hz), 1.25-1.50 (10H, m), 2.01-2.07 (2H, m), 3.76-3.82 (1H, m), 4.91-4.95 (1H, m), 4.97-5.01 (1H, m), 5.81 (1H, ddt, J=17.1 Hz, 10.4 Hz, 6.7 Hz).

Step 2. (9R)-(3'R,5'R-dibenzoyloxy-6'S-methyl-(2H)-tetrahydropyran-2-yloxy)-dec-1-ene

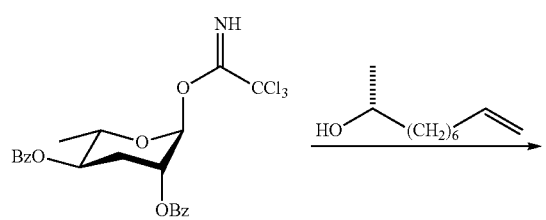

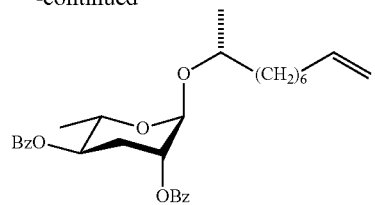

A solution of 2,4-di-O-benzoyl-ascarylose (Jeong et al. (2005) Nature 433:541-545) (139 mg, 390 µmol) in dry DCM (3 mL) was treated with trichloroacetonitrile (84 µL) and DBU (5 µL). After stirring at RT for 30 min the solution was concentrated in vacuum. Flash column chromatography on silica gel using a mixture of ethyl acetate in hexane (20%) afforded (3'R,5'R-dibenzoyloxy-6'S-methyl-(2H)-tetrahydropyran-2-yloxy)-1-(2,2,2-trichloroacetimide) (152 mg, 302 mol, 78%) as a colorless oil. A solution of 2,4-di-O-benzoyl-ascarylose-1-(2,2,2-trichloroacetimide) (152 mg, 302 µmol) in dry DCM (3 mL) at 0° C. was treated with (9R)-hydroxydec-1-ene (55 mg, 350 µmol) and trimethylsilyloxytriflate (5 µL). After 3 hours the solution was washed with saturated aqueous NaHCO₃ solution (0.5 mL), dried over Na₂SO₄ and concentrated in vacuum. Flash column chromatography on silica gel using a ethyl acetate-hexane gradient (5 to 20%) afforded (9R)-(3'R,5'R-dibenzoyloxy-6'S-methyl-(2H)-tetrahydropyran-2-yloxy)-dec-1-ene (91.1 mg, 184 mol, 61%) as a colorless oil. ¹H NMR (400 MHz, chloroform-d): δ 1.20 (3H, d, J=6.1 Hz), 1.30 (3H, d, J=6.1 Hz), 1.33-1.72 (10H, m), 2.09 (2H, m), 2.23 (1H, ddd, J=13.5 Hz, J=11.4 Hz, J=2.9 Hz), 2.44 (1H, m), 3.87 (1H, m), 4.15 (1H, dq, J=9.8 Hz, J=6.1 Hz), 4.95 (1H, ddt, J=10.2 Hz, J=2.2 Hz, J=1.3 Hz), 4.98 (1H, s.br), 5.02 (1H, ddt, J=17.1, Hz. J=2.2 Hz, J=1.6 Hz), 5.17 (1H, s.br), 5.21 (1H, ddd, J=10.3 Hz, J=4.6 Hz), 5.83 (1H, ddt, J=17.1 Hz, J=10.3 Hz, J=6.8 Hz), 7.45-7.51 (4H, m), 7.57-7.62 (2H, m), 8.06 (2H, m), 8.13 (2H, m); ¹³C NMR (100 MHz, chloroform-d): δ 17.84, 19.14, 25.65, 28.84, 29.08, 29.38, 29.68, 33.76, 37.08, 66.89, 70.62, 71.21, 72.53, 93.72, 114.20, 128.38, 129.55, 129.80, 129.82, 129.96, 133.12, 133.17, 139.01, 165.59, 165.72.

Step 3. Ethyl (10R)-(3'R,5'R-dibenzoyloxy-6'S-methyl-(2H)-tetrahydropyran-2-yloxy)-undec-2-enoate

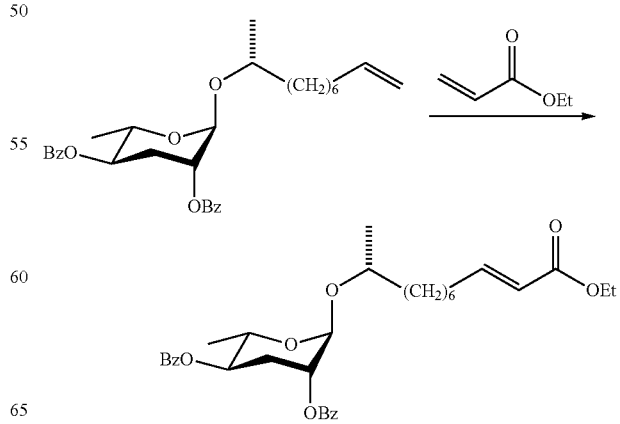

A solution of (9R)-(3'R,5'R-dibenzoyloxy-6'S-methyl-(2H)-tetrahydropyran-2-yloxy)-dec-1-ene (62 mg, 125 μmol) and ethyl propenoate (66 mg, 626 μmol) in DCM (5 mL) was treated with 1.4-benzoquinone (1.4 mg, 13 μmol) and Grubbs-II catalyst (5.3 mg, 6.3 μmol). After stirring at 40° C. for 15 h, the reaction was filtered through a pad of silica using DCM: ethyl acetate (3:1). Flash column chromatography on silica gel using a ethyl acetate-hexanes gradient (10 to 50%) afforded ethyl (10R)-(3'R,5'R-dibenzoyloxy-6'S-methyl-(2H)-tetrahydropyran-2-yloxy)-undec-2-enoate (55 mg, 97 mol, 78%) as a colorless oil. ¹H NMR (400 MHz, chloroform-d): δ 1.19 (3H, d, J=6.1 Hz), 1.27 (3H, t, J=7.1 Hz), 1.28 (3H, d, J=6.3 Hz), 1.33-1.70 (10H, m), 2.16-2.26 (3H, m), 2.38-2.46, (1H, m), 3.84 (1H, m), 4.07-4.15 (1H, m), 4.17 (2H, q, J=7.1 Hz), 4.95 (1H, s.br), 5.12-5.23 (2H, m), 5.78-5.85 (1H. m), 6.97 (1H, dt, J=15.6 Hz, 7.0 Hz), 7.42-7.50 (4H, m), 7.55-7.62 (2H, m), 8.01-8.06 (2H, m), 8.09-8.14 (2H, m). ¹³C NMR (100 MHz, chloroform-d): δ 14.42, 18.03, 19.30, 25.78, 28.16, 29.28, 29.53, 29.87, 32.32, 37.23, 60.29, 67.09, 70.80, 71.38, 72.78, 93.93, 117.65, 121.44, 128.58, 129.73, 129.98, 129.99, 130.13, 133.32, 133.38, 149.44, 165.80, 165.93, 166.89.

Step 4. (10R)-(3'R,5'R-dihydroxy-6'S-methyl-(2H)-tetrahydropyran-2-yloxy)-undec-2-enoic Acid
(ascr#17)

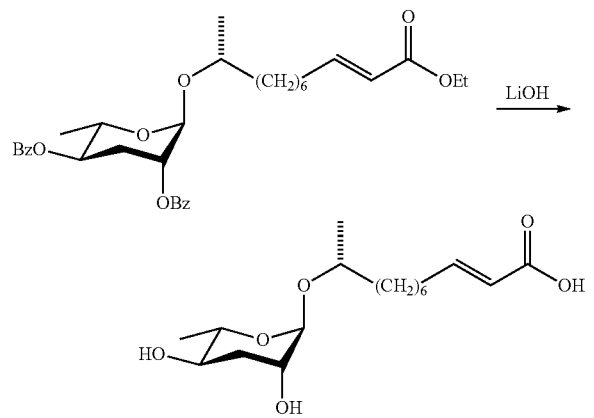

A solution of ethyl (10R)-(3'R,5'R-dibenzoyloxy-6'S-methyl-(2H)-tetrahydropyran-2-yloxy)-undec-2-enoate (55 mg, 97 μmol) in THF (1 mL) was added to a solution of lithium hydroxide (48 mg, 2 mmol) in water (380 μL) and 1,4-dioxane (2 mL). After stirring at 67° C. for 3 hours the mixture was neutralized with acetic acid and concentrated in vacuum. Flash column chromatography on silica gel using a methanol-dichloromethane gradient (0 to 30%) afforded (10R)-(3'R,5'R-dihydroxy-6'S-methyl-(2H)-tetrahydropyran-2-yloxy)-undec-2-enoic acid(ascr#17)(25.2 mg, 76.4 mol, 79%) as a colorless oil. ¹H NMR (500 MHz, methanol-d4): δ 1.12 (3H, d, J=6.1 Hz), 1.21 (3H, d, J=6.3 Hz), 1.33-1.60 (10H, m), 1.76 (1H, ddd, J=13.3 Hz, J=11.4 Hz, J=3.1 Hz), 1.95 (1H, dt.br, J=13.1 Hz, J=4.1 Hz), 2.23 (2H, ddt, J=7.3 Hz, J=1.7 Hz, J=7.6 Hz), 3.52 (1H, ddd, J=11.3 Hz, J=9.5 Hz, J=4.6 Hz), 3.63 (1H, dq, J=9.3 Hz, J=6.4 Hz), 3.71 (1H, m), 3.78 (1H, m), 4.64 (1H, s.br), 5.80 (1H, dt, J=15.7 Hz, J=1.4 Hz), 6.95 (1H, dt, J=15.6 Hz, J=7.0 Hz); ¹³C NMR (100 MHz, methanol-d4): δ 18.27, 19.53, 26.95, 29.40, 30.40, 30.61, 33.29, 36.09, 38.51, 68.45, 70.10, 71.30, 72.62, 97.67, 122.75, 151.25, 170.37.

Step 5. (10R)-(3'R,5'R-dihydroxy-6'S-methyl-(2H)-tetrahydropyran-2-yloxy)-undecanoic Acid
(ascr#18)

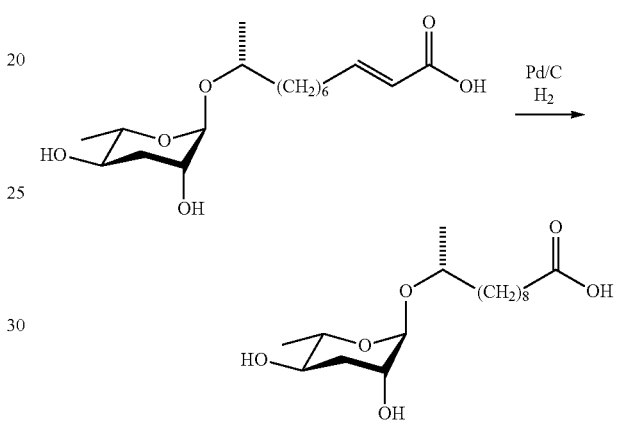

A solution of (10R)-(3'R,5' R-dihydroxy-6'S-methyl-(2H)-tetrahydropyran-2-yloxy)-undec-2-enoic acid (5 mg, 104 μmol) in methanol (1 mL) was treated with Pd/C (10% w/w) and hydrogenated for 14 h. The solution was filtered and concentrated in vacuum to afford (10R)-(3'R,5'R-dihydroxy-6'S-methyl-(2H)-tetrahydropyran-2-yloxy)-undecanoic acid(4.4 mg, 76.4 mol, 73%) as a colorless oil. ¹H NMR (500 MHz, methanol-d4): δ 1.12 (H, d, J=6.1 Hz), 1.21 (3H, d, J=6.3 Hz), 1.33-1.60 (14H, m), 1.76 (1H, ddd, J=13.3 Hz, J=11.4 Hz, J=3.1 Hz), 1.95 (1H, dt.br, J=13.1 Hz, J=4.1 Hz), 2.27 (2H, t, J=7.6 Hz), 3.52 (1H, ddd, J=11.3 Hz, J=9.5 Hz, J=4.6 Hz), 3.63 (1H, dq, J=9.3 Hz, J=6.4 Hz), 3.71 (1H, m), 3.78 (1H, m), 4.64 (1H, s.br); ¹³C NMR (100 MHz, methanol-d4): δ 18.11, 19.37, 26.40, 26.88, 30.37, 30.48, 30.61, 30.67, 35.97, 38.42, 68.34, 69.99, 71.17, 72.51, 97.56, 178.6.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for increasing disease resistance in plants, said method comprising contacting said plant or part of said plant with a composition comprising an effective amount of an isolated ascaroside, wherein said effective amount of the ascaroside increases plant resistance to one or more pathogens and primes or induces an immune response in said plant, wherein said ascaroside is selected from the group consisting of

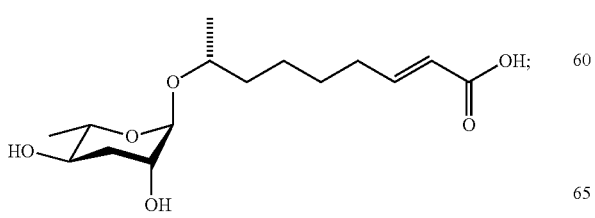

wherein n=1, 3, 5, 6, 7, 8, 9, 10, or 11;

ascr#3

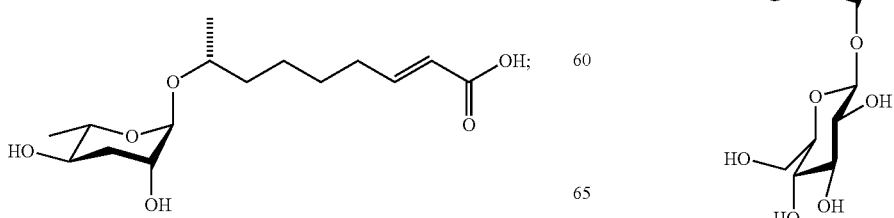

ascr#7

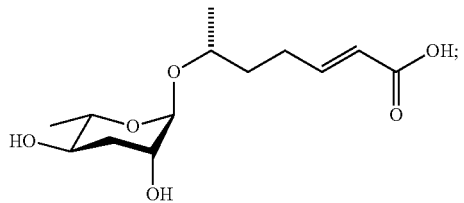

ascr#2

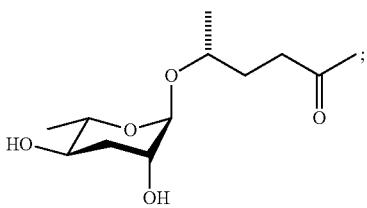

ascr#4

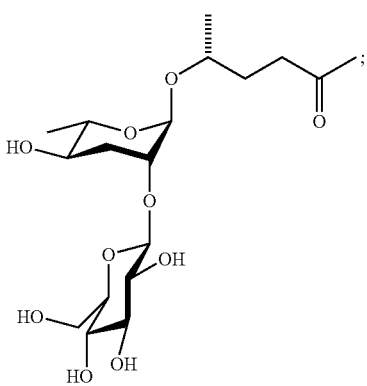

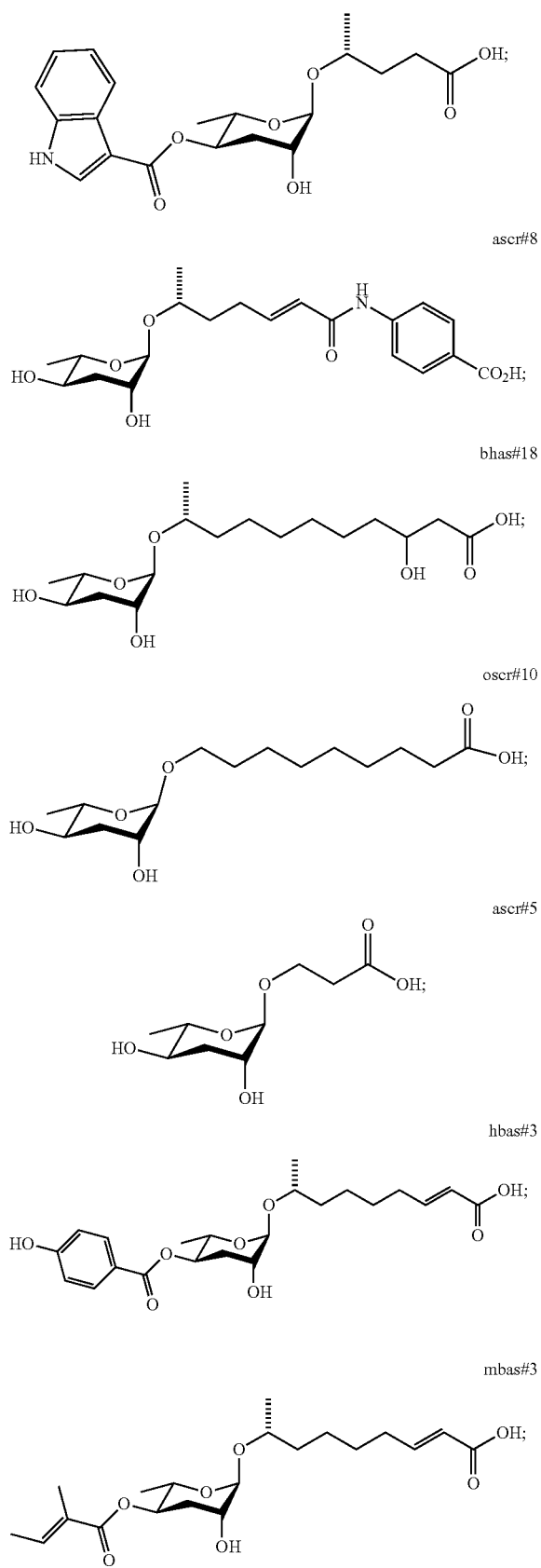

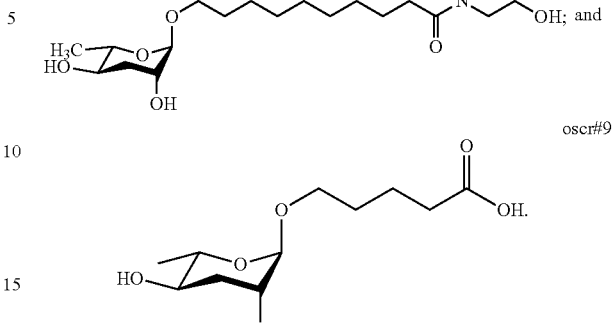

2. The method of claim 1, said method further comprising measuring at least one plant disease response parameter.

3. The method of claim 1, wherein said immune response is a basal or innate immune response in the plant.

4. The method of claim 3, wherein said response is selected from the group consisting of at least one of activation of the systemic acquired resistance, salicylic acid, jasmonate, ethylene, and nitric oxide disease response pathways.

5. The method of claim 2, wherein said plant disease response parameter is selected from the group consisting of alteration of expression of defense-related genes, callose deposition, reactive oxygen species production, $Ca^{2+}$ influx, and activation of a MAP kinase.

6. The method of claim 5, wherein said plant defense-related genes are selected from the group consisting of PR-1, PDF1.2 and FRK1; and said MAP kinase is MPK3, MPK4, or MPK6 or their orthologs.

7. The method of claim 1, wherein said part of said plant is selected from the group consisting of root, stem, leaf, seed and flower.

8. The method of claim 1, wherein said plant is selected from the group consisting of tobacco, Arabidopsis, tomato, barley, potato, sweet potato, yam, cotton, soybean, strawberry, sugar beet, corn, rice, wheat, rye, oat, sorghum, millet, bean, pea, apple, banana, pear, cherry, peach, plum, apricot, almond, grape, kiwi, mango, melon, papaya, walnut, hazelnut, pistachio, raspberry, blackberry, loganberry, blueberry, cranberry, orange, lemon, grapefruit, tangerine, lettuce, carrots, onions, broccoli, cabbage, avocado, cocoa, cassava, cotton, and flax.

9. The method of claim 1, wherein said contacting results in systemic disease resistance throughout said plant.

10. The method of claim 1, wherein said contacting results in localized resistance in said plant.

11. The method of claim 1, wherein said pathogen is a fungus.

12. The method of claim 1, wherein said pathogen is an oomycete.

13. The method of claim 1, wherein said pathogen is a bacterium.

14. The method of claim 1, wherein said pathogen is a nematode.

15. The method of claim 1, wherein said pathogen is a virus.

16. The method of claim 1, wherein said pathogen is an insect.

17. The method of claim 1, wherein said at least one ascaroside is selected from the group consisting of ascr#16, ascr#18, ascr#20, ascr#22, ascr#24, ascr#26, ascr#10, ascr#3, ascr#7, ascr#1 ascr#8, ascr#9, ascr#2, ascr#4, ascr#5, icas#9, oscr#10, mbas#3, bhas#18, and hbas#3.

18. The method of claim 1, wherein said plant is contacted with two or more ascarosides which act additively or synergistically to increase plant pathogen resistance and/or inhibit pathogen growth.

19. The method of claim 1, wherein said ascaroside is

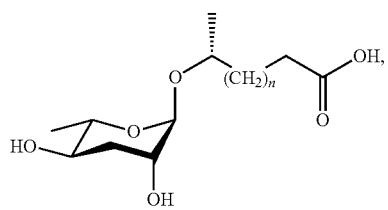

wherein n=1, 3, 5, 6, 7, 8, 9, 10, or 11.

20. The method of claim 1, wherein said ascaroside is selected from the group consisting of ascr#10, ascr#3, ascr#9, oscr#9, and easc#18.

21. A method for increasing disease resistance in plants, said method comprising contacting said plant or part of said plant with a composition comprising an effective amount of an isolated ascaroside, wherein said effective amount of the ascaroside increases plant resistance to one or more pathogens, wherein said contacting results in systemic disease resistance throughout said plant, and wherein said ascaroside is selected from the group consisting of

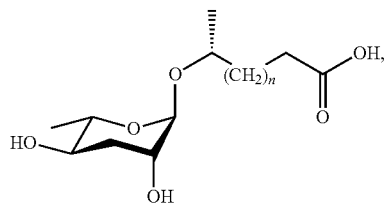

wherein n=1, 3, 5, 6, 7, 8, 9, 10, or 11;

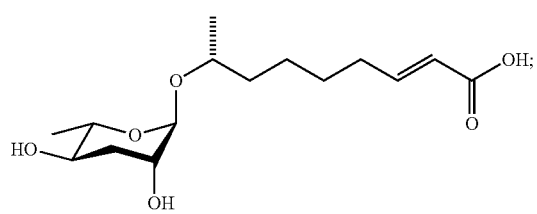

ascr#3

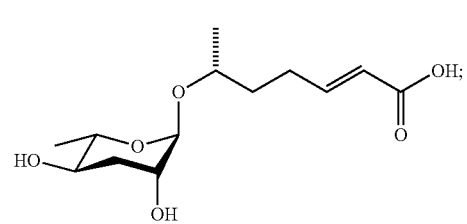

ascr#7

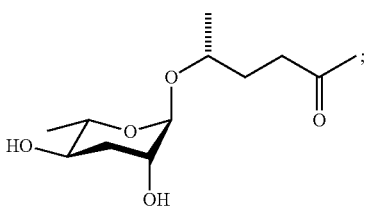

ascr#2

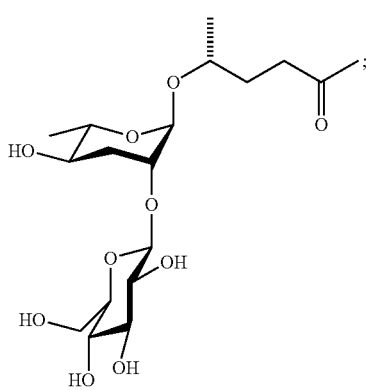

ascr#4

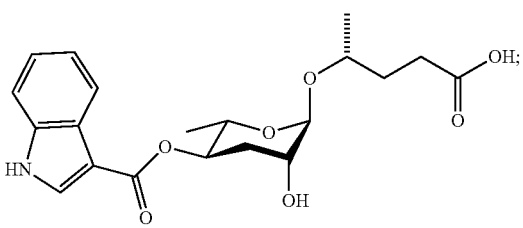

icas#9

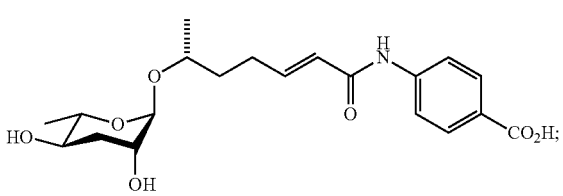

ascr#8

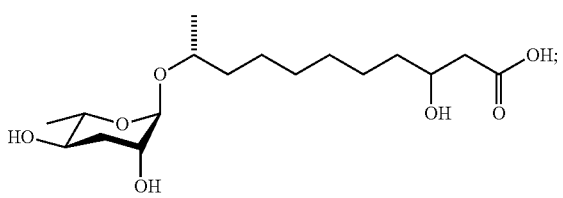

bhas#18

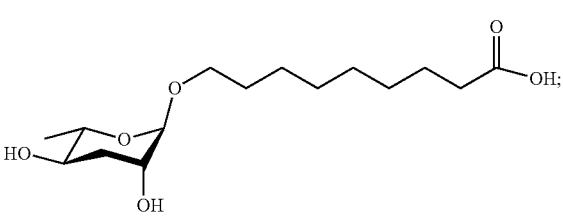

oscr#10

-continued

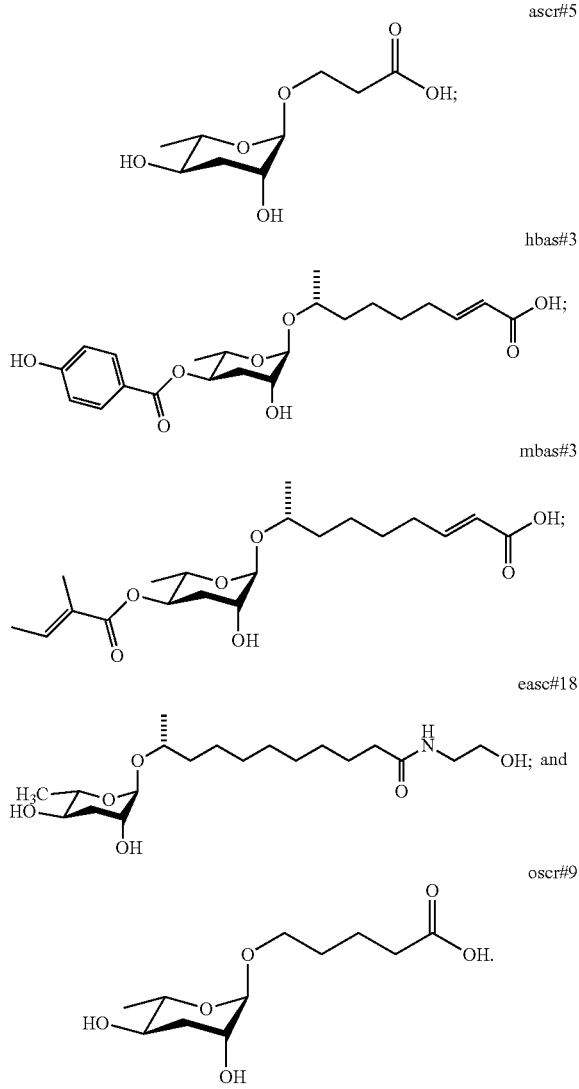

22. The method of claim 21, said method further comprising measuring at least one plant disease response parameter.

23. The method of claim 21, wherein said systemic disease resistance is due to a basal or innate immune response in the plant.

24. The method of claim 23, wherein said response is selected from the group consisting of at least one of activation of the systemic acquired resistance, salicylic acid, jasmonate, ethylene, and nitric oxide disease response pathways.

25. The method of claim 22, wherein said plant disease response parameter is selected from the group consisting of alteration of expression of defense-related genes, callose deposition, reactive oxygen species production, $Ca^{2+}$ influx, and activation of a MAP kinase.

26. The method of claim 25, wherein said plant defense-related genes are selected from the group consisting of PR-1, PDF1.2 and FRK1; and said MAP kinase is MPK3, MPK4, or MPK6 or their orthologs.

27. The method of claim 21, wherein said part of said plant is selected from the group consisting of root, stem, leaf, seed and flower.

28. The method of claim 21, wherein said plant is selected from the group consisting of tobacco, Arabidopsis, tomato, barley, potato, sweet potato, yam, cotton, soybean, strawberry, sugar beet, corn, rice, wheat, rye, oat, sorghum, millet, bean, pea, apple, banana, pear, cherry, peach, plum, apricot, almond, grape, kiwi, mango, melon, papaya, walnut, hazelnut, pistachio, raspberry, blackberry, loganberry, blueberry, cranberry, orange, lemon, grapefruit, tangerine, lettuce, carrots, onions, broccoli, cabbage, avocado, cocoa, cassava, cotton, and flax.

29. The method of claim 21, wherein said pathogen is a fungus, an oomycete, a bacterium, a nematode, a virus, or an insect.

30. The method of claim 21, wherein said at least one ascaroside is selected from the group consisting of ascr#16, ascr#18, ascr#20, ascr#22, ascr#24, ascr#26, ascr#10, ascr#3, ascr#7, ascr#1 ascr#8, ascr#9, ascr#2, ascr#4, ascr#5, icas#9, oscr#10, mbas#3, bhas#18, and hbas#3.

31. The method of claim 21, wherein said ascaroside is ascr#18.

32. The method of claim 21, wherein said plant is contacted with two or more ascarosides which act additively or synergistically to increase plant pathogen resistance and/or inhibit pathogen growth.

33. The method of claim 32, wherein said two ascarosides are ascr#18 and ascr#9.

34. The method of claim 21, wherein said ascaroside is ascr#18, wherein said pathogen is *Pseudomonas syringae* pv. *tabaci*, and wherein said plant is tobacco.

35. The method of claim 21, wherein said ascaroside is ascr#18, wherein said pathogen is *Pseudomonas syringae* pv. tomato , and wherein said plant is Arabidopsis.

36. The method of claim 21, wherein said ascaroside is ascr#18, wherein said pathogen is *Phytophthora infestans*, and wherein said plant is potato.

37. The method of claim 21, wherein said ascaroside is ascr#18, wherein said pathogen is *Phytophthora infestans*, and wherein said plant is tomato.

38. The method of claim 21, wherein said ascaroside is

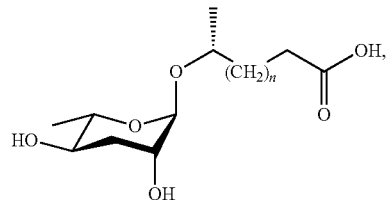

wherein n=1, 3, 5, 6, 7, 8, 9, 10, or 11.

39. The method of claim 21, wherein said at least one ascaroside is selected from the group consisting of ascr#10, ascr#3, ascr#9, oscr#9, and easc#18.

* * * * *

SEQUENCE LISTING

<160> NUMBER OF SEQ ID NOS: 56

<210> SEQ ID NO 1
<211> LENGTH: 24
<212> TYPE: DNA
<213> ORGANISM: Artificial Sequence -continued

```
<220> FEATURE:
<223> OTHER INFORMATION: Primer

<400> SEQUENCE: 1
tcgtctttgt agctcttgta ggtg                                              24

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
tagattctcg taatctcagc tct                                               23

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
tcatggctaa gtttgcttcc                                                   20

<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
aatacacacg attagcacc                                                    19

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
gtccagtgtc tgtgatattg cacc                                              24

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
ttacgaatcc gagggagcca ttg                                               23

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ggactacgac tacggctcca                                                   20
```

```
<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ggctcgtagt tgcaggtgat                                                    20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
accctcgccg actacaacat                                                    20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cagtagtggc ggtcgaagtg                                                    20

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
tgcagcgcaa ggactagag                                                     19

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
atcttcgctt ggagcttctc                                                    20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ttggtttaga cgggatggtg                                                    20

<210> SEQ ID NO 14
<211> LENGTH: 20
<212> TYPE: DNA
<213> ORGANISM: Artificial Sequence
<220> FEATURE:
<223> OTHER INFORMATION: Primer
```

<400> SEQUENCE: 14
actccagtac aagccgatcc                                                    20

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
ggccttgtat aatccctgat gaataag                                            27

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
aaagagataa caggaacgga aacatag                                            27

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
ctggaccgcc ttctgcggg                                                     19

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
agcctccgtt gctgcattgg t                                                  21

<210> SEQ ID NO 19
<211> LENGTH: 19
<212> TYPE: DNA
<213> ORGANISM: Artificial Sequence
<220> FEATURE:
<223> OTHER INFORMATION: Primer

<400> SEQUENCE: 19
tcttctcttc gccacgtgc                                                     19

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
ggttatgaac ttgatgaccc gc                                                 22

<210> SEQ ID NO 21

```
<211> LENGTH: 19
<212> TYPE: DNA
<213> ORGANISM: Artificial Sequence
<220> FEATURE:
<223> OTHER INFORMATION: Primer

<400> SEQUENCE: 21
ttgctcgcca gacacttgc                                                    19

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
gggatcacca taaacggcc                                                    19

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ggcaggaatc aaagttttcg                                                   20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cgaccaaagt gaagtggtca                                                   20

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
gcccttccat cttgcctaaa g                                                 21

<210> SEQ ID NO 26
<211> LENGTH: 23
<212> TYPE: DNA
<213> ORGANISM: Artificial Sequence
<220> FEATURE:
<223> OTHER INFORMATION: Primer

<400> SEQUENCE: 26
gtcaccaaaa caactccaga tgc                                               23

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
```
tgctacatac tcggcccttg aa                                            22

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tttggctgcc tgtttggtgt                                               20

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
ccgtcctgat ttattcatcc at                                            22

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
tcgtgtgacg aaaaatggag t                                             21

<210> SEQ ID NO 31
<211> LENGTH: 19
<212> TYPE: DNA
<213> ORGANISM: Artificial Sequence
<220> FEATURE:
<223> OTHER INFORMATION: Primer

<400> SEQUENCE: 31
gagcgtggtt actcgttca                                                19

<210> SEQ ID NO 32
<211> LENGTH: 19
<212> TYPE: DNA
<213> ORGANISM: Artificial Sequence
<220> FEATURE:
<223> OTHER INFORMATION: Primer

<400> SEQUENCE: 32
gagcgtggtt actcgttca                                                19

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
gcaacgaagg atccgaaaat                                               20

<210> SEQ ID NO 34
<211> LENGTH: 20
<212> TYPE: DNA

```
<213> ORGANISM: Artificial Sequence
<220> FEATURE:
<223> OTHER INFORMATION: Primer

<400> SEQUENCE: 34
actggccgat agtgacagtg                                                  20

<210> SEQ ID NO 35
<211> LENGTH: 23
<212> TYPE: DNA
<213> ORGANISM: Artificial Sequence
<220> FEATURE:
<223> OTHER INFORMATION: Primer

<400> SEQUENCE: 35
cagatcttta gttttgccgg tga                                              23

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
agcatccttt gggtttgggt                                                  20

<210> SEQ ID NO 37
<211> LENGTH: 17
<212> TYPE: DNA
<213> ORGANISM: Artificial Sequence
<220> FEATURE:
<223> OTHER INFORMATION: Primer

<400> SEQUENCE: 37
ctgattctgt ctgcaga                                                     17

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
tgtgtgaatt ccacccctg tg                                                22

<210> SEQ ID NO 39
<211> LENGTH: 25
<212> TYPE: DNA
<213> ORGANISM: Artificial Sequence
<220> FEATURE:
<223> OTHER INFORMATION: Primer

<400> SEQUENCE: 39
gccaaaacat tgtaaagtat atgca                                            25

<210> SEQ ID NO 40
<211> LENGTH: 22
<212> TYPE: DNA
<213> ORGANISM: Artificial Sequence
<220> FEATURE:
<223> OTHER INFORMATION: Primer

<400> SEQUENCE: 40
cttcctgacg tcaatgatca gt                                               22
```

<210> SEQ ID NO 41
<211> LENGTH: 18
<212> TYPE: DNA
<213> ORGANISM: Artificial Sequence
<220> FEATURE:
<223> OTHER INFORMATION: Primer

<400> SEQUENCE: 41
tttctcgatg agagggtc                                                   18

<210> SEQ ID NO 42
<211> LENGTH: 18
<212> TYPE: DNA
<213> ORGANISM: Artificial Sequence
<220> FEATURE:
<223> OTHER INFORMATION: Primer

<400> SEQUENCE: 42
aagctcctca aggtactg                                                   18

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
aggaactcag caagacgatg g                                               21

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
gacgtgggca ttctgggtat                                                 20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
cgacagttcc aagagggcat                                                 20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
gttcaaaccc gtaaacccgc                                                 20

<210> SEQ ID NO 47
<211> LENGTH: 23
<212> TYPE: DNA
<213> ORGANISM: Artificial Sequence
<220> FEATURE:

<223> OTHER INFORMATION: Primer

<400> SEQUENCE: 47
cccttgacat caaaggtgta gga                                          23

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
gggtgagaag gcttgtcgaa                                              20

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
gatgagataa gcagtccagc ttcc                                         24

<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
cagctgcgca tctaaccaag tg                                           22

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
ttcgattggg tcttccagga gata                                         24

<210> SEQ ID NO 52
<211> LENGTH: 22
<212> TYPE: DNA
<213> ORGANISM: Artificial Sequence
<220> FEATURE:
<223> OTHER INFORMATION: Primer

<400> SEQUENCE: 52
atcttgctgg agaccaaaac ca                                           22

<210> SEQ ID NO 53
<211> LENGTH: 27
<212> TYPE: DNA
<213> ORGANISM: Artificial Sequence
<220> FEATURE:
<223> OTHER INFORMATION: Primer

<400> SEQUENCE: 53
cctcctgtgg gaagtcttgt ggtttac                                      27

```
<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
gctccaacct gtggtaagca agtg                                          24

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
tcactttttc tgaccacttt gg                                            22

<210> SEQ ID NO 56
<211> LENGTH: 24
<212> TYPE: DNA
<213> ORGANISM: Artificial Sequence
<220> FEATURE:
<223> OTHER INFORMATION: Primer

<400> SEQUENCE: 56
aaggaagaga tatgttaagt tggg                                          24
```